United States Patent
Bashir et al.

(10) Patent No.: US 11,667,970 B2
(45) Date of Patent: Jun. 6, 2023

(54) SPATIAL MOLECULAR ANALYSIS OF TISSUE

(71) Applicants: The Board of Trustees of the University of Illinois, Urbana, IL (US); Mayo Foundation for Medical Education and Research, Rochester, MN (US)

(72) Inventors: Rashid Bashir, Champaign, IL (US); Anurup Ganguli, Champaign, IL (US); Farhad Kosari, Rochester, MN (US)

(73) Assignees: The Board of Trustees of the University of Illinois, Urbana, IL (US); Mayo Foundation for Medical Education and Research, Rochester, MN (US)

( * ) Notice: Subject to any disclaimer, the term of this patent is extended or adjusted under 35 U.S.C. 154(b) by 366 days.

(21) Appl. No.: 16/939,665

(22) Filed: Jul. 27, 2020

(65) Prior Publication Data

US 2021/0010079 A1    Jan. 14, 2021

Related U.S. Application Data

(62) Division of application No. 15/727,026, filed on Oct. 6, 2017, now Pat. No. 10,724,089.

(60) Provisional application No. 62/404,825, filed on Oct. 6, 2016.

(51) Int. Cl.
| | |
|---|---|
| C12Q 1/68 | (2018.01) |
| C12Q 1/6874 | (2018.01) |
| C12N 15/10 | (2006.01) |
| B01L 3/00 | (2006.01) |
| C12Q 1/686 | (2018.01) |
| G16B 25/00 | (2019.01) |
| G01N 1/28 | (2006.01) |
| G16B 25/10 | (2019.01) |
| G16B 30/00 | (2019.01) |
| C12Q 1/6827 | (2018.01) |

(52) U.S. Cl.
CPC .......... *C12Q 1/6874* (2013.01); *B01L 3/5027* (2013.01); *B01L 3/5085* (2013.01); *C12N 15/1003* (2013.01); *C12N 15/1096* (2013.01); *C12Q 1/686* (2013.01); *G01N 1/286* (2013.01); *G16B 25/00* (2019.02); *G16B 25/10* (2019.02); *B01L 3/50851* (2013.01); *B01L 2200/0642* (2013.01); *B01L 2300/0819* (2013.01); *B01L 2300/0858* (2013.01); *B01L 2300/0893* (2013.01); *C12Q 1/6827* (2013.01); *G01N 2001/282* (2013.01); *G01N 2001/2873* (2013.01); *G16B 30/00* (2019.02)

(58) Field of Classification Search
CPC .... C12Q 1/6874; B01L 3/5027; B01L 3/5085
See application file for complete search history.

(56) References Cited

U.S. PATENT DOCUMENTS

| | | |
|---|---|---|
| 6,101,946 A | 8/2000 | Martinsky |
| 6,410,278 B1 | 6/2002 | Notomi et al. |
| 8,945,912 B2 | 2/2015 | Bashir et al. |
| 9,376,713 B2 | 6/2016 | Bashir et al. |
| 9,433,943 B2 | 9/2016 | Bashir et al. |
| 2006/0134704 A1 | 6/2006 | Muraguchi et al. |
| 2011/0287951 A1 | 11/2011 | Emmert-Buck et al. |
| 2012/0028264 A1 | 2/2012 | Shak et al. |
| 2017/0204448 A1 | 7/2017 | Feng et al. |
| 2018/0112261 A1 | 4/2018 | Van Driel et al. |

FOREIGN PATENT DOCUMENTS

| | | |
|---|---|---|
| WO | WO 2009/158006 A2 | 12/2009 |
| WO | WO 2016/003809 A1 | 1/2016 |

OTHER PUBLICATIONS

Achim et al. (Apr. 13, 2015) "High-throughput spatial mapping of single-cell RNA-seq data to tissue of origin," Nat. Biotechnol. 33(5):503-509.
Akhmetov et al. (Sep. 30, 2015) "Assessing value of innovative molecular diagnostic tests in the concept of predictive, preventive, and personalized medicine," The EPMA Journal. 6:19. pp. 1-12.
Armani et al. (2011) "Quantifying mRNA levels across tissue sections with 2D-RT-qPCR," Analytical and Bioanalytical Chemistry. 400(10):3383-3393. doi:10.1007/S00216-011-5062-8.
Arrayit Corporation (Archived Web Page from Apr. 3, 2012) "Products—Microarray Printing," Accessible on the Internet at URL: <https://web.archive.org/web/20120403022241/http://www.arrayit.com/Products/Microarray_Printing/microarray_printing.html, 3 pgs. [Last Accessed Jan. 16, 2018].
Bagasra (2007) "Protocols for the in situ PCR-amplification and detection of mRNA and DNA sequences," Nat. Protoc. 2(11):2782-2795.

(Continued)

*Primary Examiner* — Kenneth R Horlick
(74) *Attorney, Agent, or Firm* — Leydig, Voit & Mayer, Ltd.

(57) ABSTRACT

Various methods and devices for spatial molecular analysis from tissue is provided. For example, a method of spatially mapping a tissue sample is provided with a microarray having a plurality of wells, wherein adjacent wells are separated by a shearing surface; overlaying said microarray with a tissue sample; applying a deformable substrate to an upper surface of said tissue sample; applying a force to the deformable substrate, thereby forcing underlying tissue sample into the plurality of wells; shearing the tissue sample along the shearing surface into a plurality of tissue sample islands, with each unique tissue sample island positioned in a unique well; and imaging or quantifying said plurality of tissue sample islands, thereby generating a spatial map of said tissue sample. The imaging and/or quantifying may use a nucleic acid amplification technique.

16 Claims, 43 Drawing Sheets

Specification includes a Sequence Listing.

(56) References Cited

OTHER PUBLICATIONS

Bain (2005) "Diagnosis from the blood smear," New England Journal of Medicine. 353(5):498-507.
Barker Jr. et al. (1992) "A simple method to detect Plasmodium falciparum directly from blood samples using the polymerase chain reaction," The American Journal of Tropical Medicine and Hygiene. 46(4):416-426.
Bhargava (2007) "Towards a practical Fourier transform infrared chemical imaging protocol for cancer histopathology," Anal. Bioanal. Chem. 389(4):1155-1169.
Bhargava et al. (2006) "High throughput assessment of cells and tissues: Bayesian classification of spectral metrics from infrared vibrational spectroscopic imaging data," Biochim. Biophys. Acta. 1758(7):830-845.
Biotek Instruments, Inc. (Jan. 16, 2006) "NanoQuot™ Microplate Dispenser," Accessible on the Internet at URL: http://www.biotek.com/about/news.html?id=8672, 2 pgs. [Last Accessed Jan. 16, 2018].
Brambilla et al. (2003) "Multicenter evaluation of use of dried blood and plasma spot specimens in quantitative assays for human immunodeficiency virus RNA: measurement, precision, and RNA stability," Journal of Clinical Microbiology. 41(5):1888-1893.
Brittain-Long et al. (2008) "Multiplex real-time PCR for detection of respiratory tract infections," Journal of Clinical Virology. 41(1):53-56.
Cepheid (Archived Web Page from Jan. 13, 2015) "GeneXpert® IV," Accessible on the Internet at URL: https://web.archive.org/web/20150113054642/http://www.cepheid.com/us/cepheid-solutions/systems/genexpert-systems/genexpert-iv, 2 pgs. [Last Accessed Jan. 16, 2018].
Chen et al. (Apr. 2009) "Rapid pre-clinical detection of classical swine fever by reverse transcription loop-mediated isothermal amplification," Molecular and Cellular Probes. 23(2):71-74.
Cheville et al. (2008) "Gene Panel Model Predictive of Outcome in Men at High-Risk of Systemic Progression and Death From Prostate Cancer After Radical Retropubic Prostatectomy," Journal of Clinical Oncology. 26(24):3930-3936.
Collins et al. (2005) "Prospective Identification of Tumorigenic Prostate Cancer Stem Cells," Cancer Research. 65(23):10946-10952. doi:10.1158/0008-5472.CAN-05-2018.
Curtis et al. (2012) "Isothermal amplification using a chemical heating device for point-of-care detection of HIV-1," PLoS one. 7(2):1-9.
Damhorst et al. (Oct. 16, 2015) "Smartphone-imaged HIV-1 reverse transcription loopmediated isothermal amplification (RT-LAMP) on a chip from whole blood," Engineering (Beijing). 1(3):324-335.
De Bruin et al. (Aug. 26, 2016) "A method for assessing efficiency of bacterial cell disruption and DNA release," BMC microbiology. 16(197):1-10.
Duarte-Guevara et al. (Oct. 19, 2016) "On-chip electrical detection of parallel loop-mediated isothermal amplification with DG-BioFETs for the detection of foodborne bacterial pathogens," RSC Advances. 6(106):103872-103887.
Espina et al. (2006) "Laser-capture microdissection," Nature Protocols. 1(2):586-603.
Fauci et al. (2012) "The perpetual challenge of infectious diseases," New England Journal of Medicine. 366(5):454-461.
Feldman et al. (2001) "The development of androgen-independent prostate cancer," Nat. Rev. Cancer. 1(1):34-45.
Femino et al. (1998) "Visualization of Single RNA Transcripts in Situ," Science. 280(5363):585-590.
Fend et al. (1999) "Immuno-LCM: Laser Capture Microdissection of Immunostained Frozen Sections for mRNA Analysis," Am. J. Pathol. 154(1):61-66.
Fernandez et al. (2005) "Infrared spectroscopic imaging for histopathologic recognition," Nat. Biotechnol. 23(4):469-474.
Fink et al. (2000) "Immunostaining and laser-assisted cell picking for mRNA analysis," Laboratory Investigation. 80(3):327-333.
Ganguli et al. (Aug. 22, 2017) "Hands-free smartphone-based diagnostics for simultaneous detection of Zika, Chikungunya, and Dengue at point-of-care," Biomedical Microdevices. 19(4):1-13.
Genbank Database [Online] (Nov. 30, 2017) "*Homo sapiens* DNA topoisomerase II alpha (TOP2A), mRNA," Accession No. NM_001067.3. National Center for Biotechnology Information. Accessible on the Internet at URL: https://www.ncbi.nlm.nih.gov/nuccore/NM_001067.3, 14 pgs. [Last Accessed Jan. 16, 2018].
Goldsworthy et al. (1999) "Effects of fixation on RNA extraction and amplification from laser capture microdissected tissue," Mol. Carcinog. 25(2):86-91.
Gunson et al. (2005) "Real-time RT-PCR detection of 12 respiratory viral infections in four triplex reactions," Journal of Clinical Virology. 33(4):341-344.
Islam et al. (Mar. 8, 2017) "A Review on Macroscale and Microscale Cell Lysis Methods," Micromachines. 8(3):1-27.
Itonaga et al. (Mar. 21, 2016) "Novel Methodology for Rapid Detection of KRAS Mutation Using PNA-LNA Mediated Loop-Mediated Isothermal Amplification," PLoS One. 11(3):e0151654.
Itzkovitz et al. (2012) "Single-molecule transcript counting of stem-cell markers in the mouse intestine," Nature Cell Biology. 14(1):106-114.
Karnes et al. (2010) "The ability of biomarkers to predict systemic progression in men with high-risk prostate cancer treated surgically is dependent on ERG status," Cancer Res. 70:8994-9002.
Koivisto et al. (1997) "Androgen Receptor Gene Amplification: A Possible Molecular Mechanism for Androgen Deprivation Therapy Failure in Prostate Cancer," Cancer Res. 57(2):314-319.
Larsson et al. (1990) "Optimization of non-radioactive in situ hybridization: image analysis of varying pretreatment, hybridization and probe labelling conditions," Histochemistry and Cell Biology. 93(4):347-354.
Lawn et al. (Mar. 24, 2013) "Advances in tuberculosis diagnostics: the Xpert MTB/RIF assay and future prospects for a point-of-care test," The Lancet Infectious Diseases. 13(4):349-361.
Loonen et al. (Aug. 15, 2013) "Comparison of pathogen DNA isolation methods from large volumes of whole blood to improve molecular diagnosis of bloodstream infections," PLoS one. 8(8):1-7.
Lowe (Mar. 30, 3015) "Flash Storage Technical and Economic Primer," Accessible on the Internet at URL: http://www.flashstorage.com/flash-storage-technical-economic-primer, 18 pgs. [Last Accessed Jan. 16, 2018].
Lundborg et al. (2002) "Antibiotic prescribing in outpatients: a 1-week diagnosis-prescribing study in 5 counties in Sweden," Scandinavian Journal of Infectious Diseases. 34(6):442-448.
Lyubimova et al. (Aug. 15, 2013) "Single-molecule mRNA detection and counting in mammalian tissue," Nat. Protoc. 8(9):1743-1758.
Mabey et al. (2004) "Tropical infectious diseases: diagnostics for the developing world," Nature Reviews Microbiology. 2(3):231-240.
Mancini et al. (2010) "The era of molecular and other non-culture-based methods in diagnosis of sepsis," Clinical Microbiology Reviews. 23(1):235-251.
Martin et al. (Dec. 2, 2015) "National health spending in 2014: faster growth driven by coverage expansion and prescription drug spending," Health Affairs. 35(1):150-160.
McNerney et al. (2011) "Towards a point-of-care test for active tuberculosis: obstacles and opportunities," Nature Reviews Microbiology. 9(3):204-213.
Micron Technology, Inc. (Archived Web Page from Mar. 18, 2017) "3D XPoint™ Technology," Accessible on the Internet at URL: https://web.archive.org/web/20170318225432/https://www.micron.com/about/our-innovation/3d-xpoint-technology, 3 pgs. [Last Accessed Jan. 16, 2018].
Moffitt et al. (Nov. 22, 2016) "High-performance multiplexed fluorescence in situ hybridization in culture and tissue with matrix imprinting and clearing," Proc. Natl. Acad. Sci. 113(50):14456-14461.
Morton et al. (Mar. 29, 2014) "Identification of mRNAs and lincRNAs associated with lung cancer progression using next-

(56) References Cited

OTHER PUBLICATIONS generation RNA sequencing from laser micro-dissected archival FFPE tissue specimens," Lung Cancer. 85(1):31-39.
Musashi Engineering Inc. (Archived Web Page from Mar. 29, 2015) "Super small amount fixed-quantity dispenser: Nano Master SMP-III," Accessible on the Internet at URL: http://web.archive.org/web/20150329061256/http://www.musashi-engineering.co.jp.e.cn.hp.transer.com/products/100_3-1-2-2.html, 2 pgs. [Last Accessed Jan. 16, 2018].
Notomi et al. (2000) "Loop-mediated isothermal amplification of DNA," Nucl. Acids Res. 28(12):E63. pp. 1-7.
Owano (Dec. 2, 2012) "Taiwan engineers defeat limits of flash memory," Accessible on the Internet at URL: https://phys.org/news/2012-12-taiwan-defeat-limits-memory.html, 8 pgs. [Last Accessed Jan. 16, 2018].
Packard et al. (Jan. 17, 2013) "Performance evaluation of fast microfluidic thermal lysis of bacteria for diagnostic sample preparation," Diagnostics. 3(1):105-116.
Perner et al. (Oct. 1, 2016) "Sepsis: frontiers in diagnosis, resuscitation and antibiotic therapy," Intensive Care Medicine. 42(12):1958-1969.
Peters et al. (2004) "New developments in the diagnosis of bloodstream infections," The Lancet Infectious Diseases. 4(12):751-760.
Pham et al. (Apr. 2005) "Loop-mediated isothermal amplification for rapid detection of Newcastle disease virus," Journal of Clinical Microbiology. 43(4):1646-1650.
Pienta et al. (2006) "Mechanisms underlying the development of androgen-independent prostate cancer," Clinical Cancer Research. 12(6):1665-1671.
Priye et al. (Mar. 20, 2017) "A smartphone-based diagnostic platform for rapid detection of Zika, chikungunya, and dengue viruses," Scientific Reports. 7(44778):1-11.
Raj et al. (2008) "Imaging individual mRNA molecules using multiple singly labeled probes," Nature Methods. 5(10):877-879.
Satija et al. (Apr. 13, 2015) "Spatial reconstruction of single-cell gene expression data," Nat. Biotechnol. 33(5):495-502.
Seok et al. (Jun. 1, 2017) "A Paper-Based Device for Performing Loop-Mediated Isothermal Amplification with Real-Time Simultaneous Detection of Multiple DNA Targets," Theranostics. 7(8):2220.
Siegel et al. (Jan. 5, 2015) "Cancer Statistics, 2015" CA: A Cancer Journal for Clinicians. 65(1):5-29.
Song et al. (Jun. 29, 2016) "Instrument-free point-of-care molecular detection of Zika virus," Analytical Chemistry. 88(14):7289-7294.
Stahl et al. (Jul. 1, 2016) "Visualization and analysis of gene expression in tissue sections by spatial transcriptomics," Science. 353(6294):78-82.
Stepankova et al. (Oct. 14, 2013) "Strategies for Stabilization of Enzymes in Organic Solvents," ACS Catal. 3(12):2823-2836.
Tomlins et al. (2007) "Integrative molecular concept modeling of prostate cancer progression," Nat. Genet. 39(1):41-51.
Toumazou et al. (Jun. 9, 2013) "Simultaneous DNA amplification and detection using a pH-sensing semiconductor system," Nature Methods. 10(7):641-646.
Veigas et al. (Jan. 27, 2017) "Quantitative real-time monitoring of RCA amplification of cancer biomarkers mediated by a flexible ion sensitive platform," Biosensors and Bioelectronics. 91:788-795.
Vincent et al. (Mar. 2, 2013) "Sepsis definitions: time for change," Lancet. 381(9868):774-779.
Wang et al. (2006) "Histological staining methods preparatory to laser capture microdissection significantly affect the integrity of the cellular RNA," BMC Genomics. 7(1):97.
Wang et al. (Jun. 11, 2013) "Current trends in detecting non-O157 Shiga toxin-producing *Escherichia coli* in food," Foodborne pathogens and disease. 10(8):665-677.
World Health Organization (2016) "Global tuberculosis report 2016," Executive Summary, pp. 1-3.
World Health Organization (Jun. 2015) "A WHO external quality assurance scheme for malaria nucleic acid amplification testing," Global Malaria Programme. Meeting Report, pp. 1-16.
Yeh et al. (Mar. 22, 2017) "Self-powered integrated microfluidic point-of-care low-cost enabling (SIMPLE) chip," Science Advances. 3(3):1-12.

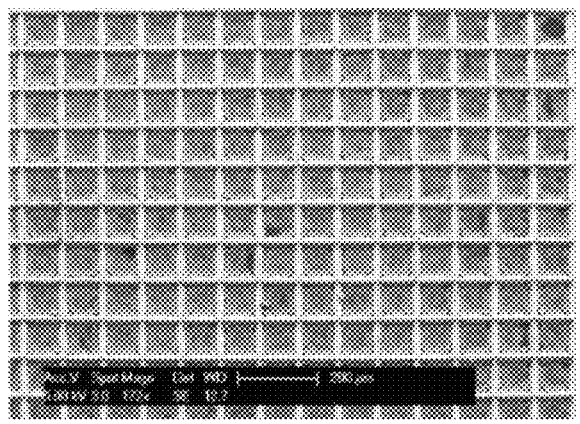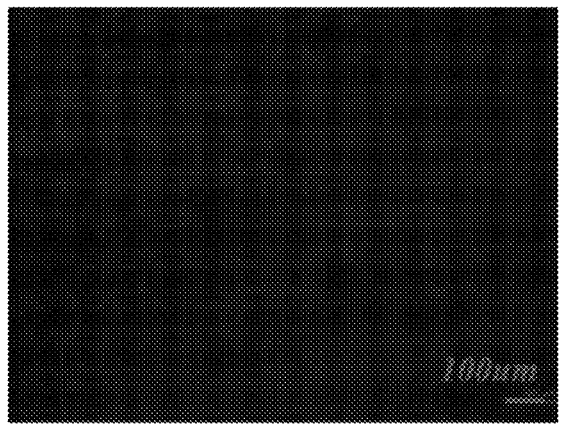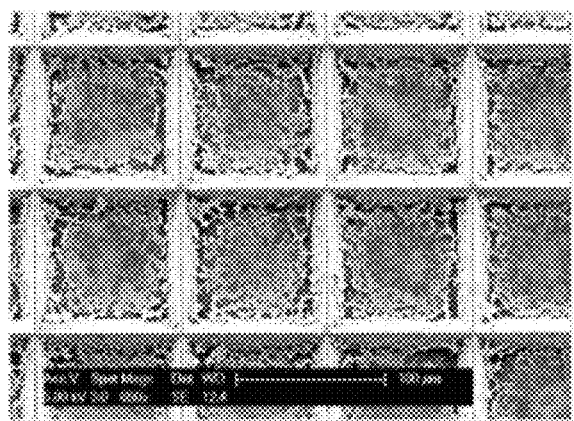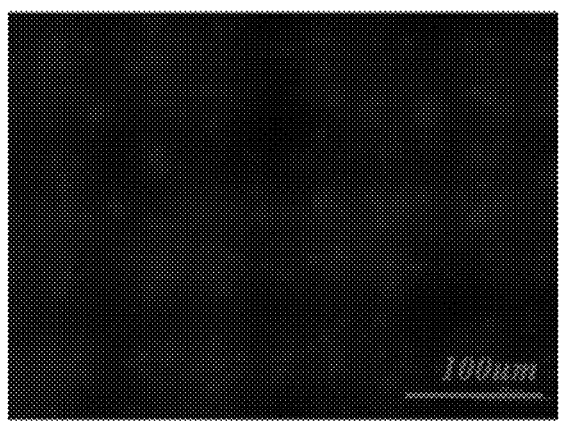
SEM                                    Fluorescence
FIG. 2A

Raw amplification curves

Standard curve

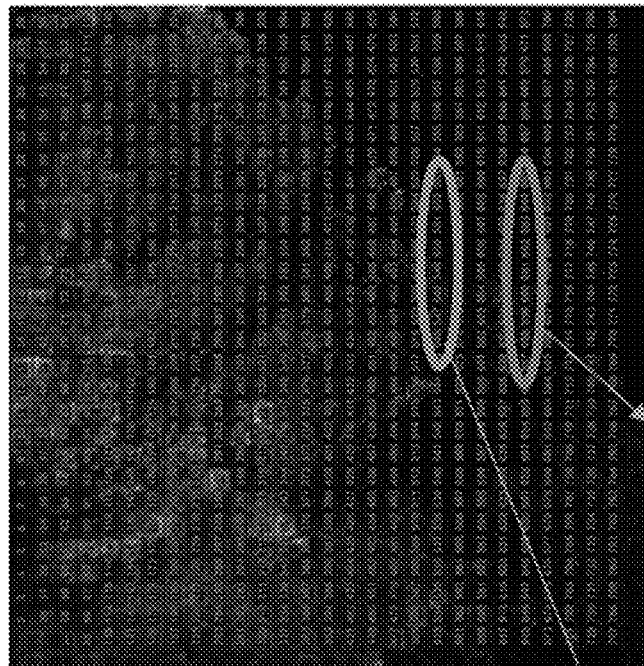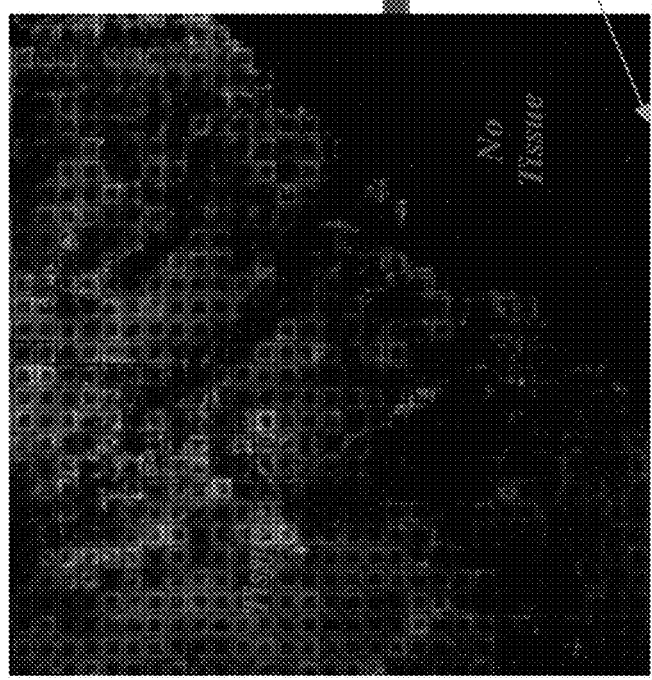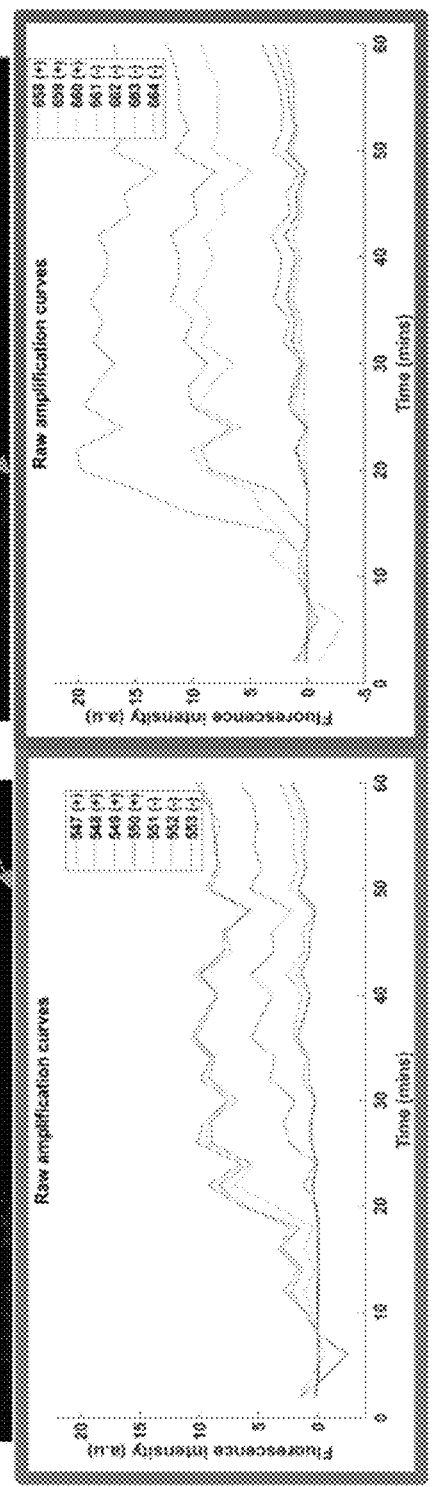
FIG. 13B
FIG. 13A
FIG. 13D
FIG. 13C

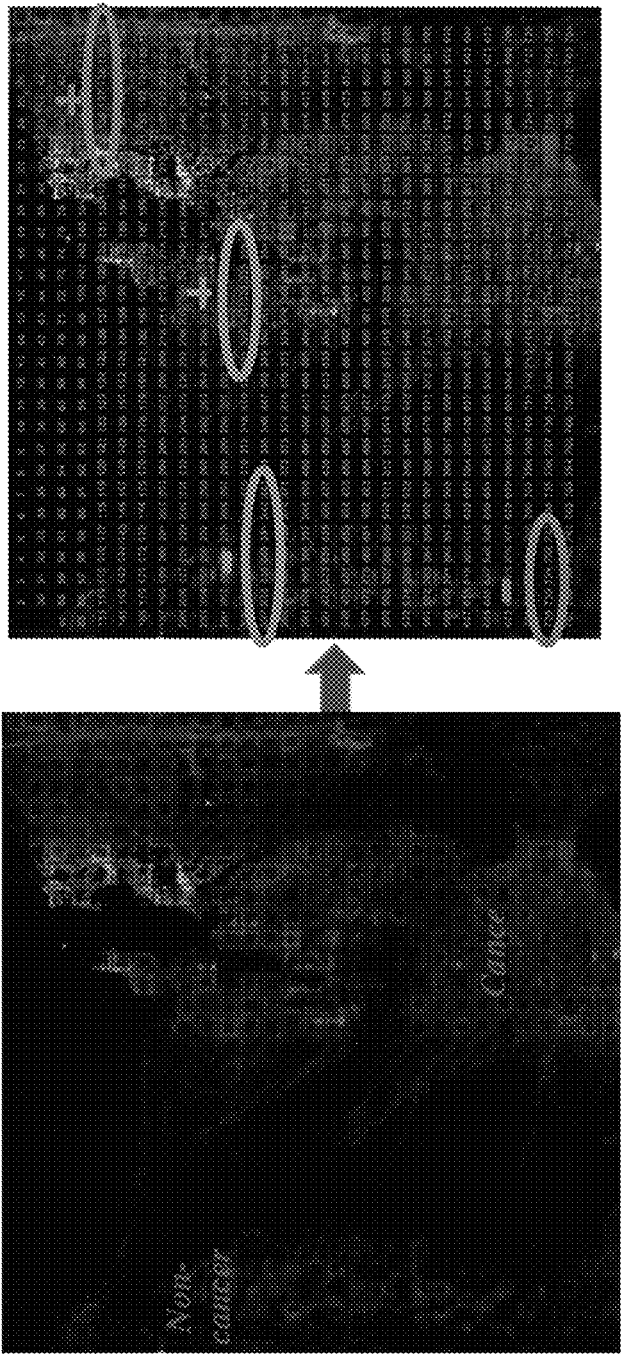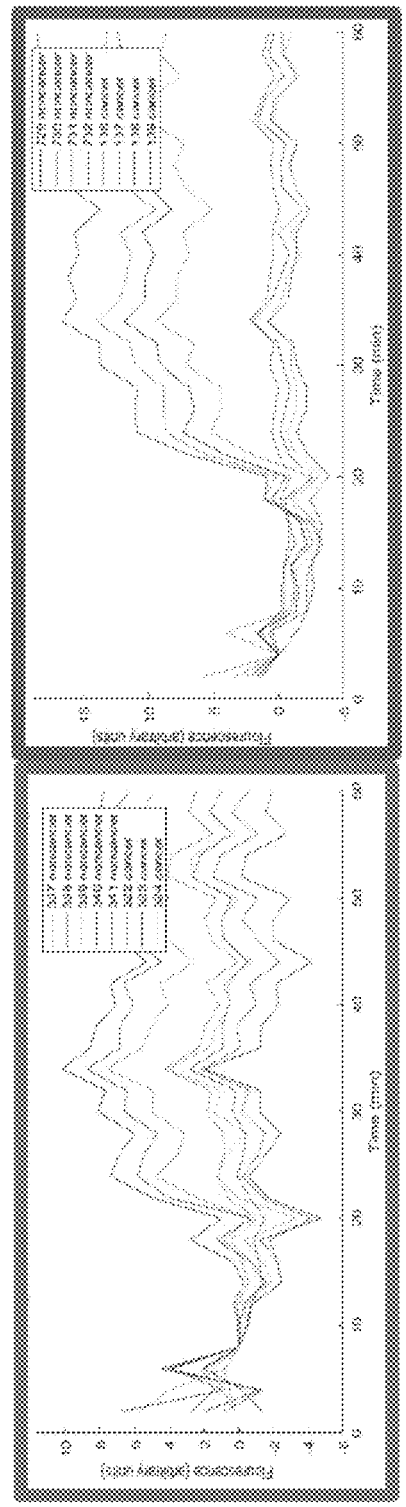
FIG. 15A  FIG. 15B  FIG. 15C  FIG. 15D

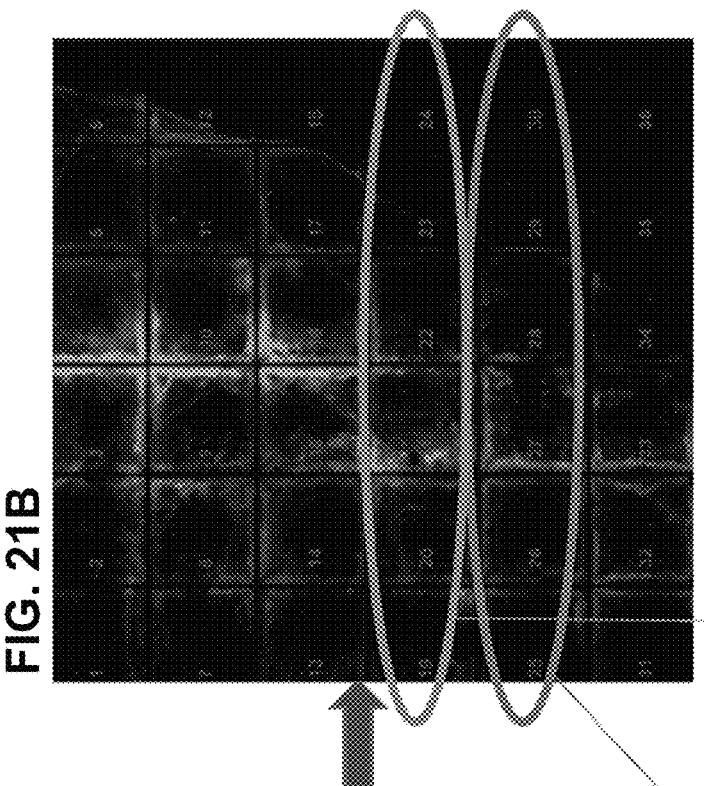
FIG. 21A
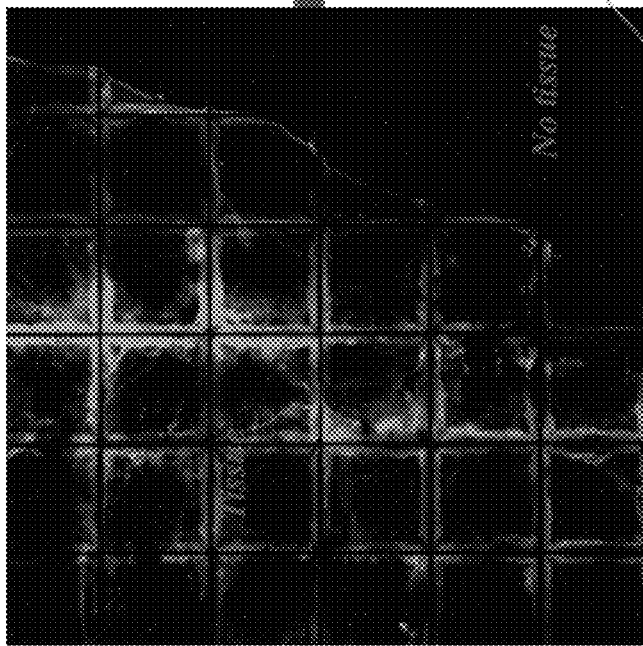
FIG. 21B
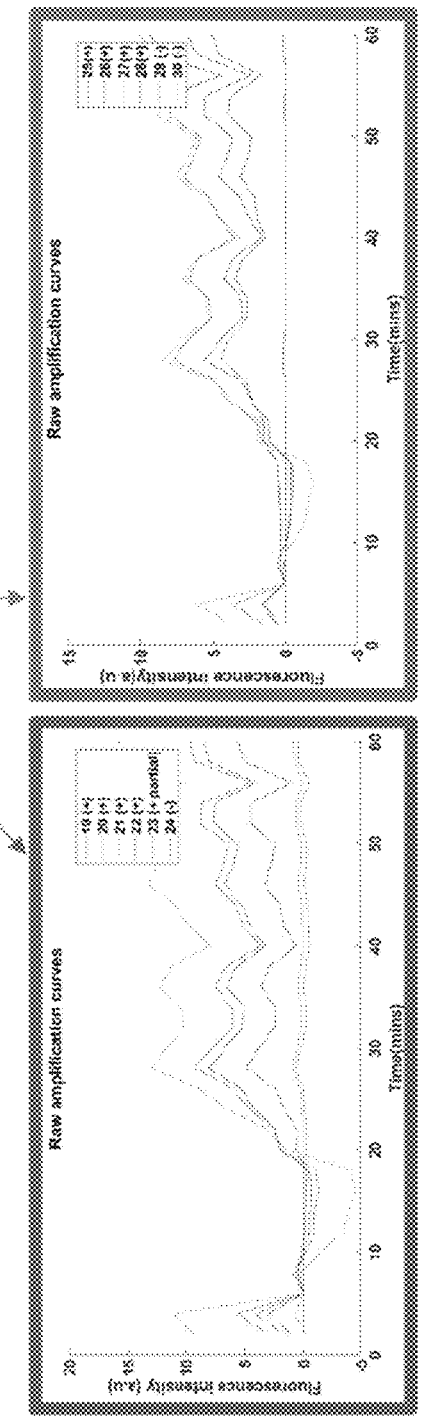
FIG. 21C
FIG. 21D

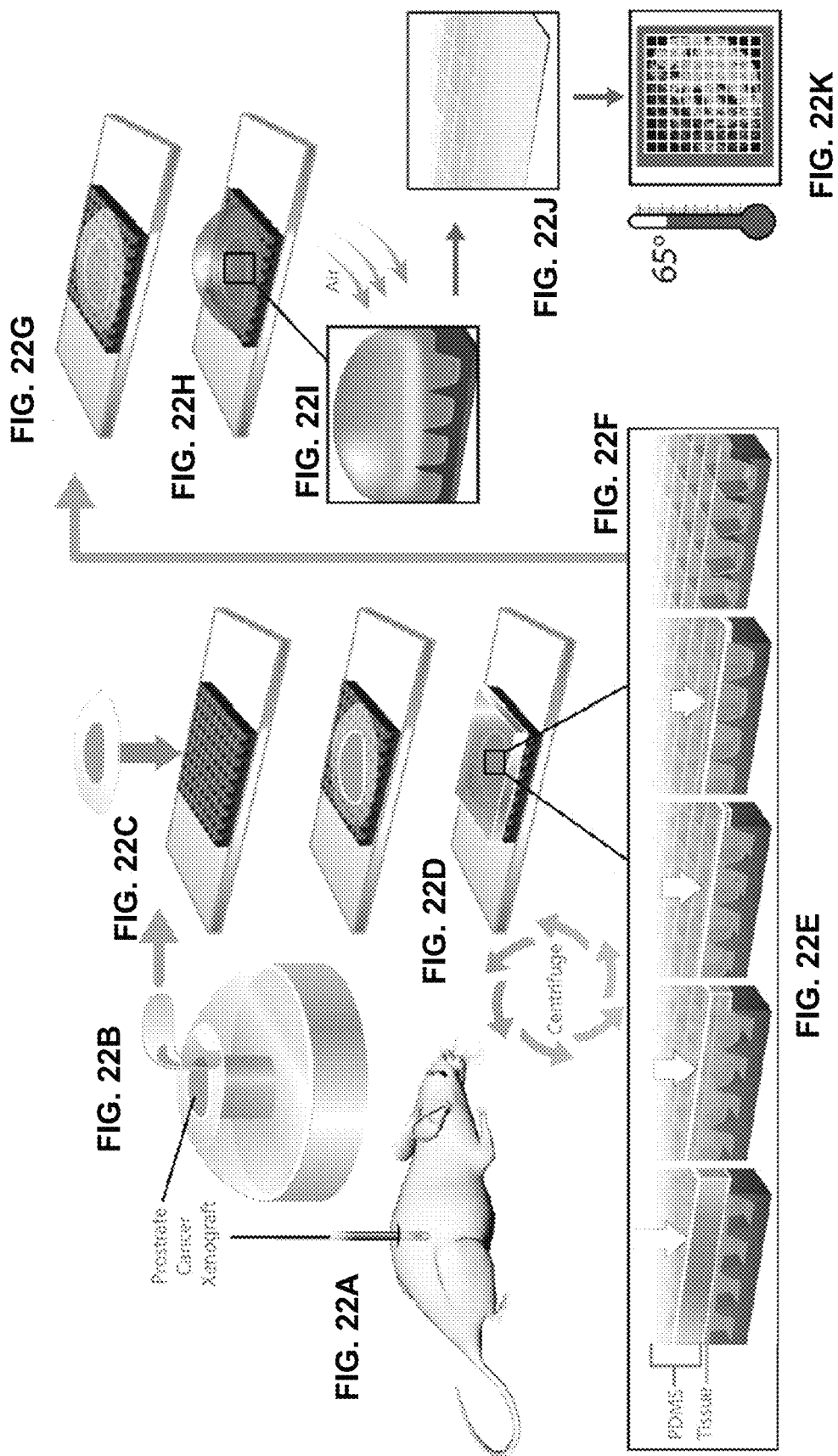

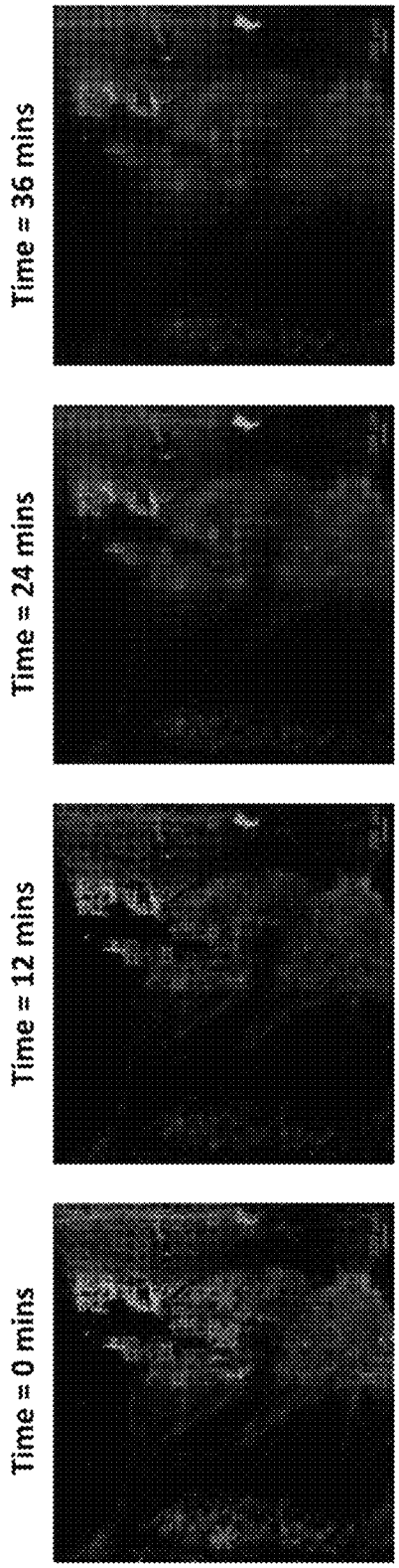
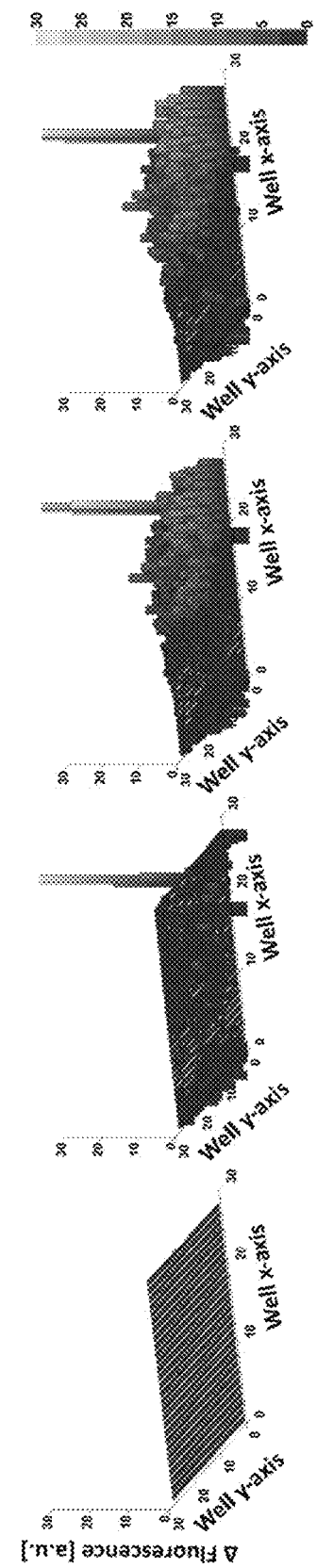
FIG. 25A
FIG. 25B

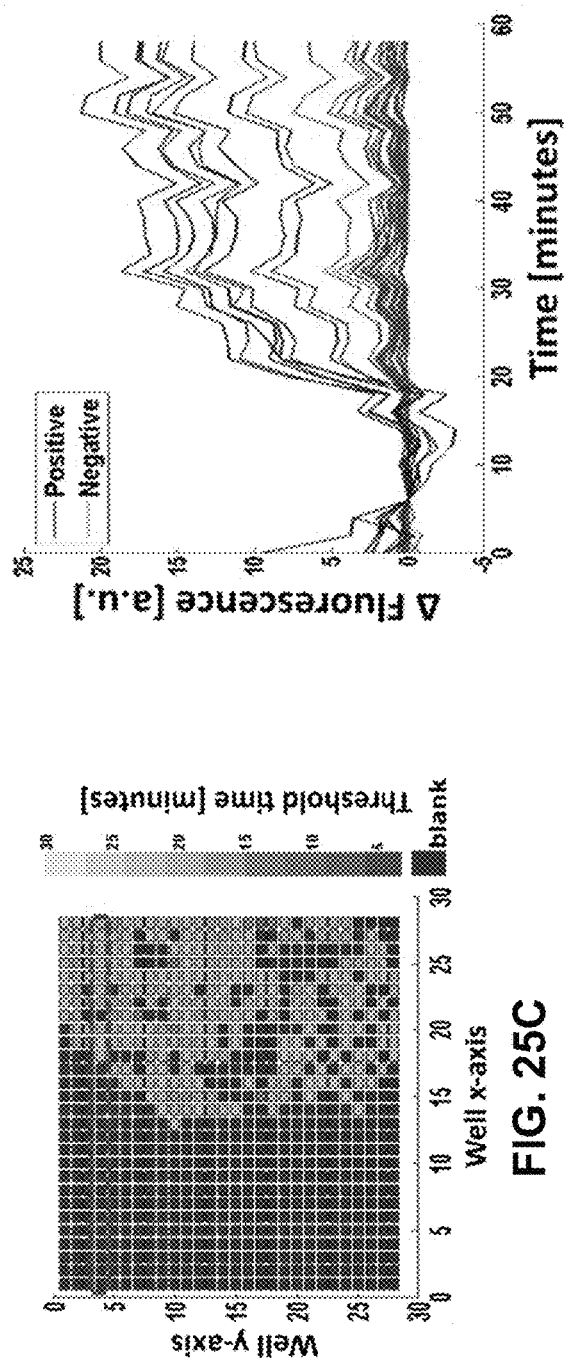
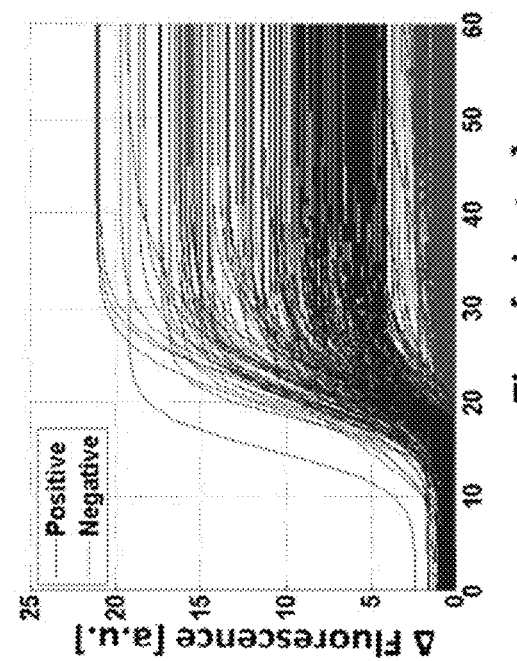
FIG. 25C
FIG. 25D
FIG. 25E

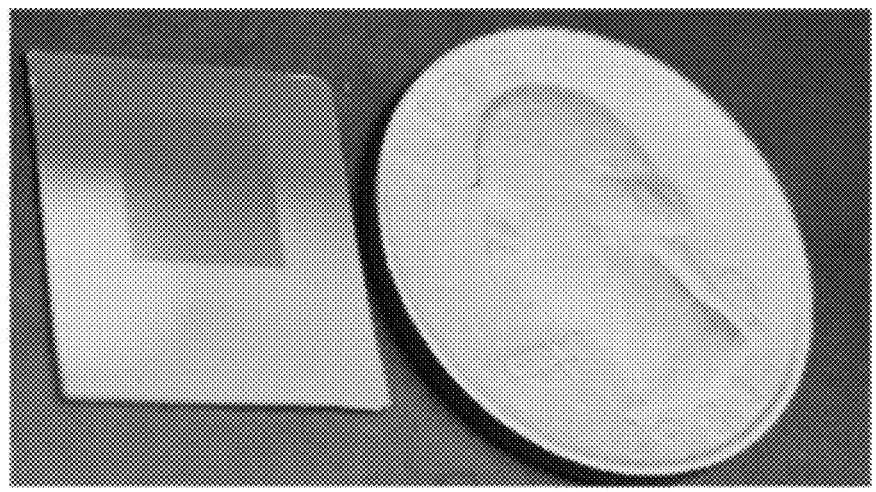
FIG. 27
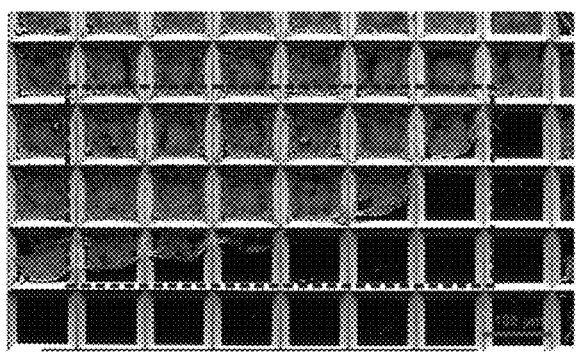 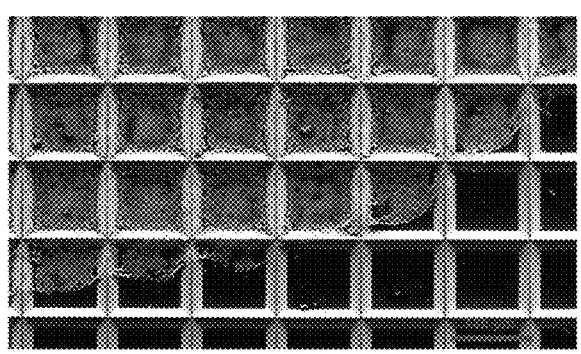
FIG. 28A              FIG. 28B

Mouse cell lines
3T3
RAW
Hoechst
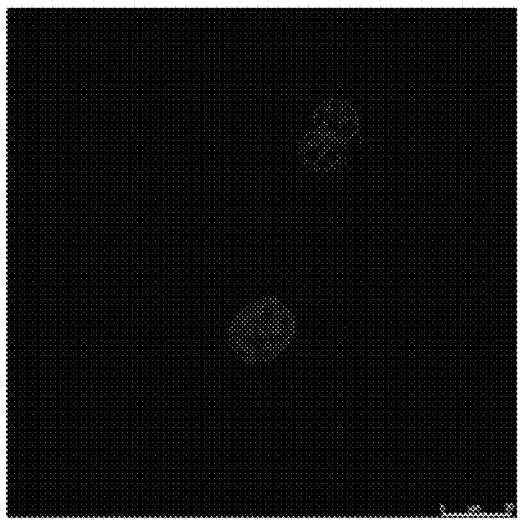
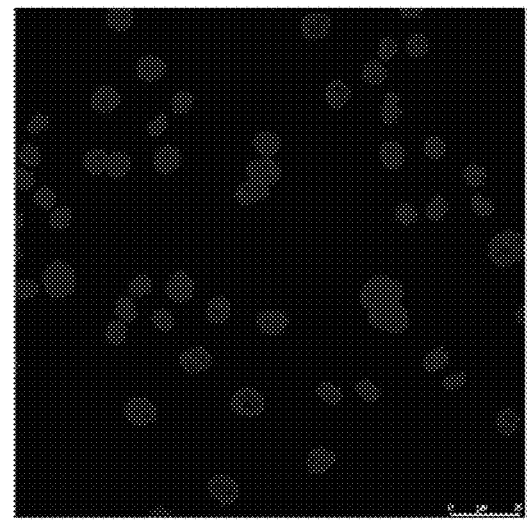
Quasar 647
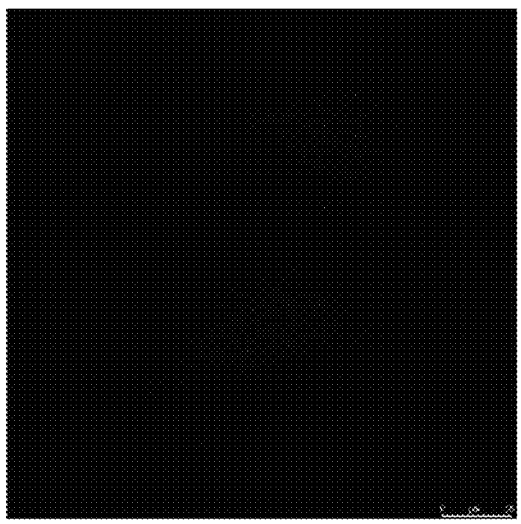
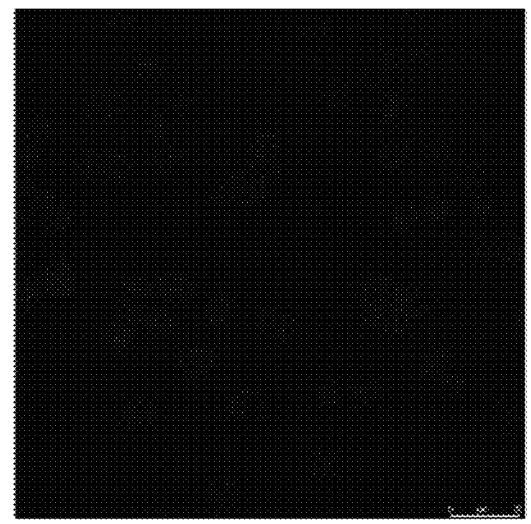
FIG. 30A
FIG. 30B

Human cell lines
PC-3
LnCap
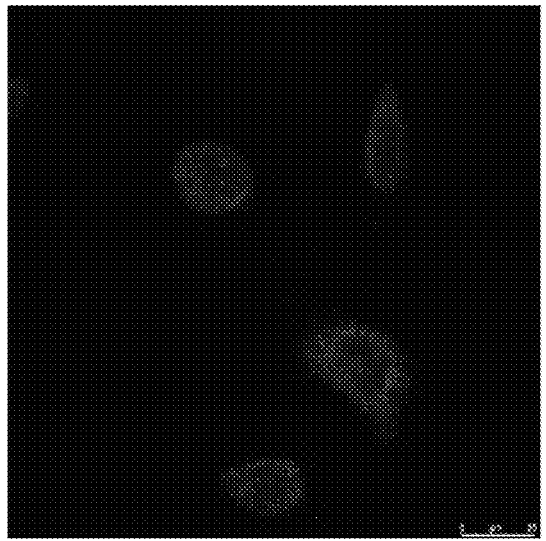
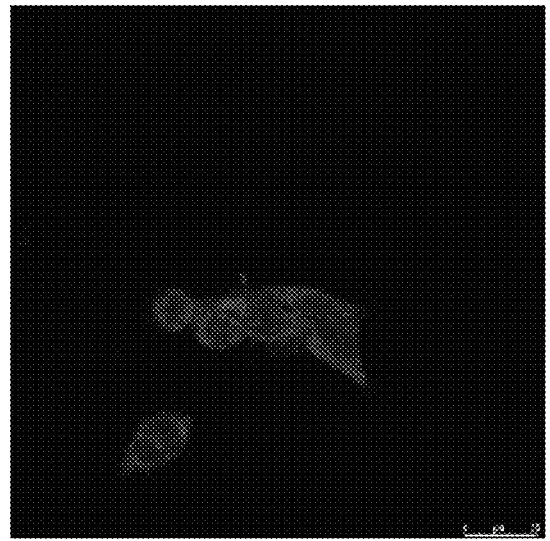
FIG. 30C
FIG. 30D

SEQUENCE LISTING

```
<160> NUMBER OF SEQ ID NOS: 44

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
gtcgtgtcag accttgaa                                                   18

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
tagttccttt tggggcag                                                   18

<210> SEQ ID NO 3
<211> LENGTH: 41
<212> TYPE: DNA
<213> ORGANISM: Artificial Sequence
```

```
<220> FEATURE:
<223> OTHER INFORMATION: Synthetic Construct

<400> SEQUENCE: 3
tctgggaaat gtgtagcagg aggctgatga tgttaagggc a                41

<210> SEQ ID NO 4
<211> LENGTH: 43
<212> TYPE: DNA
<213> ORGANISM: Artificial Sequence
<220> FEATURE:
<223> OTHER INFORMATION: Synthetic Construct

<400> SEQUENCE: 4
aacccagttc ctaaaaagaa tgtgagtgga ggtggaagac tga              43

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ggcttgaaga cagtggtaca c                                      21

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
cagtgaagaa gacagcagca a                                      21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tggctgcctc tgagtctgaa                                        20

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
agtcttctgc aatccagtcc tctt                                   24

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tgttacggag tcactctttt                                        20
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
agttgaaggt tggtccagaa                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
accaaagggg catatcaaga                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ccaagtcttc tttccacaaa                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
cttcaacagc ctccaattct                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
tgttcatctt gtttttcctt                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
atggttattc gtggaatgac                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 16
ttttaggcct tctagttcca                                         20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
ttggcttaaa tgccaatgta                                         20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
gattctgaat cagaccaggg                                         20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
aattactttc gtcactgctc                                         20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
tgtttctcgt ggagggacat                                         20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
taggtggact agcatctgat                                         20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
cttcaaggtc tgacacgaca                                         20

<210> SEQ ID NO 23

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
ggcttgaaga cagtggtaca                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
tctgggaaat gtgtagcagg                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
actgggtttg taatttcagt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
agtggaggtg gaagactgac                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
caaagctgga tccctttag                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
gcttttgaga gacaccagaa                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
```
attcttggtt ttggcaggat                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
ggatttcttg cttgtgactg                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
atggaagtca tcactctccc                                              20

<210> SEQ ID NO 32
<211> LENGTH: 19
<212> TYPE: DNA
<213> ORGANISM: Artificial Sequence
<220> FEATURE:
<223> OTHER INFORMATION: Synthetic Construct

<400> SEQUENCE: 32
cacagctgag tcaaagtcc                                               19

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
ttaaaaccag tcttgggctt                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
ttgggcttta cttcactttg                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
ccatgagatg gtcactattt                                              20

<210> SEQ ID NO 36
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 36
gctgaagtga tcagatagct                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37
tgctctatct catatctact                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
gagtatctgt actagaacca                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
ttggcacata agaggctgag                                                    20

<210> SEQ ID NO 40
<211> LENGTH: 20
<212> TYPE: DNA
<213> ORGANISM: Artificial Sequence
<220> FEATURE:
<223> OTHER INFORMATION: Synthetic Construct

<400> SEQUENCE: 40
tgagcaattt ctcattgctt                                                    20

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
ggcctctgat gatttgagaa                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
aaattggttt ctctctttgg                                                    20
```

```
<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
cttggatcaa atgttgtccc                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
attgctgagc atggttatca                                              20
```

SPATIAL MOLECULAR ANALYSIS OF TISSUE

CROSS-REFERENCE TO RELATED APPLICATIONS

This application is a divisional of U.S. patent application Ser. No. 15/727,026, filed Oct. 6, 2017 (now U.S. Pat. No. 10,724,089, issued Jul. 28, 2020), which claims the benefit of and priority to U.S. Provisional Application No. 62/404,825, filed Oct. 6, 2016, each of which is hereby incorporated in its entirety to the extent not inconsistent herewith.

STATEMENT REGARDING FEDERALLY SPONSORED RESEARCH OR DEVELOPMENT

This invention was made with government support under 1534126 awarded by The National Science Foundation, 59-8072-6-001 awarded by The United States Department of Agriculture, and 087126 awarded by The National Institutes of Health. The government has certain rights in the invention.

REFERENCE TO A SEQUENCE LISTING

A sequence listing containing SEQ. ID. NOs. 1-44 is submitted herewith and is specifically incorporated by reference.

BACKGROUND OF INVENTION

The spatial localization of gene expression can unravel important insights into tissue heterogeneity, functionality and pathological transformations, but the ability to maintain this spatial information remains an enduring challenge in tissue sections routinely used for pathology. Amplification-based spatial gene expression analysis methods provide good sensitivity and specificity but decouple the analyte isolation and biochemical detection steps, making them low throughput and laborious constraints, limiting the translation of the above methods into routine research and clinical practice. Direct probe-based hybridization techniques such as single molecule FISH allow direct visualization of single RNA molecules in their native cellular context but are not amenable on tissue sections in a high throughout manner. In addition, off-target binding of FISH probes and cellular auto-fluorescence can also become a limiting factor in imaging tissue samples. Methods to perform spatially-mapped transcriptome analysis on a tissue section can identify multiple targets simultaneously but they must trade-off between the histologic reference and the quality of recovered biomaterials as staining and manual identification are often needed.

The limitations described above are addressed herein by a special platform to reliably pixelate a tissue section into separate islands of tissue that reside in separate wells and that can be individually analyzed, thereby providing a highly sensitive, reproducible and efficient platform for spatial analysis of tissue. The methods and systems are compatible with on-chip picoliter real-time reverse transcriptase loop mediated isothermal amplification (RT-LAMP) reactions on a histological tissue section, including without any analyte purification, while preserving the native spatial location of the nucleic acid molecules. In an exemplary methodology, the entire process from tissue loading on microchip to results from RT-LAMP, can be carried out in less than two hours. This technique with its ease of use, fast turnaround, and quantitative molecular outputs, is invaluable for a range of applications, including tissue analysis, for researchers and clinicians.

SUMMARY OF THE INVENTION

The methods and systems provided herein overcome conventional limitations and problems associated with spatial imaging of tissue samples, including spatial gene expression useful for tissue characterization. The ability to reliably and efficiently achieve spatial molecular analysis of tissue relies on pixelating tissue samples into individual wells. Corresponding efficient processing of the pixelated tissue, including by reliable interaction of reagent materials and tissue, bulk fluid application and removal, and avoiding cross-talk between different wells containing different pixelated tissue, together ensure the methods and systems provide significant functional benefits that ensure reliable spatial mapping of a tissue sample.

Provided herein are various methods of spatially mapping a tissue sample. The method is particular suited for obtaining information about a biological tissue that may spatially vary, such as arising from different cell type, cell state, pathogen, disease state, therapeutic response state, target analyte, including presence or absence of a target nucleic acid. The method may comprise the steps of: providing a microarray having a plurality of wells, wherein adjacent wells are separated by a shearing surface; overlaying the microarray with a tissue sample; applying a deformable substrate to an upper surface of the tissue sample; applying a force to said deformable substrate, thereby forcing underlying tissue sample into the plurality of wells; shearing the tissue sample along the shearing surface into a plurality of tissue sample islands, with each unique tissue sample island positioned in a unique well; and imaging or quantifying the plurality of tissue sample islands, thereby generating a spatial map of the tissue sample. The spatial map may be observed in real time on a display and/or may be digitally recorded for later analysis.

The method may further comprise the step of pre-spotting or printing one or more molecules on a surface of the plurality of wells. The molecules may be useful in the imaging or quantifying step. For example, in applications where nucleic acid amplification occurs, the molecules may comprise enzymes and/or primers useful in the amplification technique.

Any of the methods may further comprise the step of removing the deformable substrate before the imagining or quantifying step and applying a reagent for use in the imaging or quantifying step. In this aspect, some materials may be pre-spotted/printed and other materials may be applied at a later time point in the method.

The reagent may comprise a plurality of reagents for nucleic acid amplification, the method further comprising the step of amplifying each of said plurality of wells using a nucleic acid amplification technique, including polymerase chain reaction (PCR) or an isothermal technique, thereby generating a plurality of amplified products. Accordingly, the imaging may comprise analyzing the plurality of amplified products, thereby generating a spatial gene analysis of the tissue sample. The imaging may be optical in nature, such as by fluorescence or phase-contrast microscopy. The imaging may be electrical in nature, such as by monitoring a change in an electrical parameter in the wells, including using a FET, such as an ISFET.

The step of applying a force upon the microarray may be by any technique that reliable forces the deformable substrate into the plurality of wells, such that the tissue is sheared into separate pieces (e.g., "islands" or "pixelated"), with each piece in a unique well. Suitable force application techniques include by spinning the assembled microarray, tissue sample and deformable substrate in a centrifuge. The resultant centrifugal force accordingly forces the deformable substrate, and corresponding underlying tissue, into the wells. Similarly, a non-centrifugal uniform force may be applied over the deformable substrate, such as a weighted block or driver that results in desired deformable substrate deformation into the wells and corresponding shearing of the tissue sample into corresponding wells.

The wells may be described as having a volume of less than or equal to 1000 pL; a cross-sectional dimension of less than or equal to 1 mm, or a maximum depth of less than or equal to 1 mm.

The method is compatible with a range of tissue samples, including a histological tissue section. The tissue sample may be described as having an average thickness, including of less than or equal to 20 μm or a range between 3 μm and 20 μm. The tissue sample may be cryopreserved.

The deformable layer may comprise a polymer or an elastomer, or any material that exhibits a deformation property such that after the applied force is removed, the deformable layer exits the wells and relaxes back to a rest state. In contrast, the plurality of tissue sample islands remains within the wells. The wells may be coated with an adhesion-promoting layer that ensures a bonding force between the tissue and the well that is greater than the adhesion force between the tissue and the deformable layer. This ensures that tissue islands remain in the wells even when the deformable layer exits the wells. Accordingly, the deformable layer may be coated with an anti-adhesion-promoting layer to minimize the adhesive force between the tissue and the deformable substrate.

The deformable substrate may be formed of a polymer that is polymethylsiloxane (PDMS), SU-8, polyethylene glycol (PEG), a photoresist, a PEG-based polymer or any combination thereof.

The method may further comprise the step of delivering one or more reagents and/or molecules to the plurality of wells before the step of overlaying said microarray with the tissue sample, wherein the one or more reagents and/or molecules are useful for the imaging or quantifying step.

The method may further comprise the step of delivering one or more reagents and/or molecules to the plurality of wells after the shearing step, wherein the one or more reagents and/or molecules are useful for the imaging or quantifying step and the delivering is by one or more than one delivery application steps.

The method may further comprise the step of processing the tissue sample islands by: removing the deformable substrate; applying reagents used to image and/or quantify the tissue sample islands to each of the wells, wherein the applying step comprises: covering the wells with liquid reagent, wherein the liquid reagent enters the wells by capillary action; immersing the wells with liquid reagent in an inert covering fluid having a density that is less than the liquid reagent density, thereby enveloping each well containing a tissue sample island and liquid reagent without entering the wells; and removing excess reagent by forcing a gas over the microarray, thereby avoiding cross-talk between different wells. In this manner, the liquid filling is rapid, reliable, and avoids unwanted material communication between adjacent wells. The covering fluid may comprise mineral oil.

Any of the tissue sample islands may be fixed and permeabilized, including to facilitate desired interaction between biological material and reagents and/or molecules in the liquid reagent.

The nucleic acid amplification technique may comprise PCR or an isothermal technique, such as reverse transcription, loop-mediated isothermal amplification (RT-LAMP).

Any of the methods may comprise fluorescent imaging to facilitate mapping of the tissue sample that has been pixelated into tissue islands.

The method may further comprise adding an optically detectable dye or particle to each of the plurality of wells.

The mapping may be a quantifiable mapping, such as by measuring an optical, electrical and/or mechanical parameter in each of the wells. Mechanical properties may include stress-induced mechanical bending or resonant frequency of a mechanical resonator (e.g. a quartz crystal microbalance or MEMS cantilever). Electrical parameters may be measured, for example, by field effect transistors.

The methods provided herein may are compatible for a range of applications, including for one or more of: an on-chip spatial gene expression analysis; on-chip spatial RNA sequence analysis; on-chip spatial methylation analysis; on-chip gene mutation analysis; copy number variation analysis; or insertion and deletion analysis.

The method may be for pathogen detection, tissue functionality assessment, or pathological diagnostics. Examples of pathogen detection include detection of bacteria, fungi, mold, or viruses, including by amplification of target nucleic acids specific for the genome of a range of bacteria or viruses. The configuration of systems and methods provided herein allows for highly multiplexed detection, including different target analytes having, for example, different fluorescent spectrum.

The method is compatible with a range of well numbers, including greater than 500 wells up to 10,000, 100,000 or $1 \times 10^6$. In this manner, even for relatively large surface area tissue, a desired spatial resolution may be maintained.

Also provided herein are devices for performing any of the methods described herein. For example, provided is a device for generating a pixelized tissue sample comprising: a substrate; a plurality of wells supported by or embedded in the substrate; and a shearing surface positioned between adjacent wells, wherein the shearing surface has a sharp edge configured to sever a tissue sample under an applied centrifugal force into a plurality of tissue sample islands, with each well containing a unique tissue sample island so as to maintain spatial information of a tissue sample during use.

The substrate may be silicon, a glass, a metal, an insulator or a dielectric.

The shearing surface may be described as having a sharp edge along which during use the tissue sample is sheared. The well may have a geometric shape that is inverted pyramidal. Other geometric shapes are compatible, so long as the sharp edge is accessible to the tissue and the tissue is capable of being forced into the well.

Each of the wells may comprise a target-specific primer set and an enzyme for nucleic acid amplification. The primer set is selected, as known in the art, for specificity to a desired portion of a nucleic acid, such as in a genome indicative of a pathogen or mutation.

The device may further comprise a deformable substrate configured to cover the plurality of wells and during application of a force, to force a tissue sample into each of the plurality of wells.

Also provided herein is a method for generating a pixelated, spatially-preserved tissue sample. Numerous functional advantages are achieved with such methods, including the ability to rapidly, reliably and at a high sensitivity and resolution, characterize molecular variation of a tissue sample, The method may comprise the steps of: providing a microarray having a plurality of wells, wherein at least a portion of each edge of the well is a shearing surface; providing a tissue sample in contact with each of the wells; overlaying a deformable layer on said tissue sample; applying a force upon the deformable layer, thereby forcing the deformable layer and the tissue sample into the plurality of wells and shearing the tissue sample into a plurality of tissue sample islands positioned in the plurality of wells; and relaxing the force, thereby removing the deformable layer from the plurality of wells, while maintaining the plurality of tissue sample islands positioned in the plurality of wells, thereby generating a pixelated, spatially-preserved tissue sample.

Also provided is a method of determining spatial gene expression by: loading a cryopreserved tissue sample onto a chip, the chip comprising a substrate having a plurality of inverted pyramidal microwells with sharp, defined edges; placing an organic polymer on top of the cryopreserved tissue sample; centrifuging the substrate to force the organic polymer to force the tissue sample into the microwells, thereby shearing the tissue sample and forming a pixelated tissue sample; removing the organic polymer from the pixelated tissue sample; applying a plurality of PCR (or LAMP) reagents in bulk by pipetting the reagents to cover the entirety of the microwells and allowing the reagents to enter the microwells by capillary action; applying mineral oil to cover the microwells and applying forced air at an angle to remove excess reagents while keeping the reagents located inside the microwells; performing PCR (or LAMP) in the microwells by incubating the chip at a desired temperature to create a plurality of PCR products; and analyzing the presence of the plurality of PCR products.

The well size may be about 5 µm on a side to about 1000 µm on a side. The well size is about 1 µm deep to about 1000 µm deep. Accordingly, the wells may be described a microwell, referring to at least one dimension that is less than 1 mm.

The primers may be printed or spotted in the wells prior to the transfer and pixelation of the tissue.

The organic polymer may be described as pliable and capable of entering the microwells and pushing the tissue sample into the well when centrifugal force is applied, and bending back to its original shape and vacating the microwells when centrifugal force is no longer applied.

The organic polymer may be polydimethylsiloxane (PDMS), SU8, photoresist, and any PEG based material.

Any of the methods described herein may have a plurality of PCR products that are fluorescent, thereby facilitating imaging and, if desired, quantifying.

The nucleic acid amplification reagents may be suitable for reverse transcription loop-mediated isothermal amplification (RT-LAMP) or PCR.

The presence of the plurality of PCR or LAMP products can be detected by fluorescence or electrical means, including by fluorescent imaging or FET devices, including ISFETs. Mechanical properties may be measured using one or more mechanical sensors, such as QCM (quartz crystal microbalance) or MEMS (microelectromechanical system) resonator.

Also provided is a gene expression analysis chip comprising a substrate comprising a plurality of microwells having inverted pyramidal walls and sharp, distinct edges. The substrate may be silicon oxide on silicon. The size of the microwells may be about 5 µm on a side to about 1000 µm on a side and/or about 1 µm deep to about 1000 µm deep.

The chip can be used to analyze many different cell populations.

Also provided is a kit for performing spatial gene expression analysis on tissue, the kit comprising at least one of the any chips described herein, at least one polymerase enzyme, and dinucleotide triphosphates (dNTPs) in a single, dry format; wherein said reagent preparation is water soluble and stable above 4° C.

The kit may further comprise a target-specific primer set.

The kit may further comprise a positive control.

The polymerase and target-specific primer set may be printed or spotted onto the chip.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

The features, objects and advantages other than those set forth herein will become more readily apparent when consideration is given to the detailed description below. Such detailed description makes reference to the following drawings, wherein:

FIG. 2A. SEM and DAPI-fluorescence characterization of the same chip after tissue pixelation. Tissue partitioning and division into small pixels (pixelation) can be clearly visualized as tissue seen inside the wells.

FIG. 4A. Raw fluorescence images of real-time RT-LAMP with tissue on chip at four different time points. FIG. 4B. Fluorescence bar graphs of the raw images showing a differential increase in fluorescence over time. The gain in fluorescence over time is calculated taking time=0 image (initial) as the reference. FIG. 4C. Spatial threshold analysis showing the spatially mapped threshold times. Note that the tissue boundaries are maintained during reaction. Threshold time=0 refers to blanks. FIG. 4D. Raw amplification curves of a row showing positive and negative wells.

FIG. 5A. Raw fluorescence images of real-time RT-LAMP with prostate cancer tissue on right and non-cancer (mouse skeletal muscle) tissue on left of chip at four different time points. FIG. 5B. Fluorescence bar graphs of the raw images showing a differential increase in fluorescence over time. The gain in fluorescence over time is calculated taking time=0 image (initial) as the reference. Note the amplification occurring only for the cancerous tissue. FIG. 5C. Spatial threshold analysis showing the spatially mapped threshold times. Threshold time=0 refers to blanks. FIG. 5D. Raw amplification curves of a row showing positive and negative wells. Note that well 23 shows no amplification and is captured in the threshold analysis.

FIG. 6A. Optical image of the chip. FIG. 6B. SEM image of the wells. FIG. 6C. SEM image of the sharp well edge shown as red box in FIG. 6B. Note that the edge width is close to 1 micron. FIG. 6D. Surface profilometer measurement of fabricated silicon oxide micro wells showing the depth of the wells.

FIG. 7A. Stitched fluorescent image of the complete chip showing filling distribution of the wells using a Rhodamine dye. It can be seen that only some of the wells at the edges are partially filled. The well edges are dark and clearly visible indicating no cross-talk between adjacent wells. FIG. 7B. Histogram showing the well fluorescence distribution after filling. Note that lower fluorescence is attributed to partially filled wells and higher fluorescence values are for wells without tissue.

FIG. 13A. Raw fluorescence image at time 0 showing regions with and without tissue. FIG. 13B. Processed image with numbered wells (FIG. 13C). FIG. 13D. Raw amplification curves for marked regions showing that the positive wells (with tissue) amplify while the adjacent negatives don't and that the tissue boundary remains preserved during amplification. This confirms that there is no cross talk between adjacent wells.

FIG. 15A. Raw fluorescence image at time 0 showing regions with and without tissue. FIG. 15B. Processed image with numbered wells (FIG. 15C). FIG. 15D. Raw amplification curves for marked regions showing that the positive wells (with cancerous tissue) amplify while the negatives (with non-cancerous tissue) don't and also that the tissue boundary remains the tissue boundary remains preserved during amplification. This confirms that our on-chip reaction is specific.

FIG. 16A. Raw fluorescence images of RT-LAMP reaction on chip with no-primers in the reaction mix. FIG. 16B. Raw fluorescence curves of all the wells showing no amplification.

FIG. 17A. Raw fluorescence images of RT-LAMP reaction on chip with RNase A treated tissue. FIG. 17B. Raw fluorescence curves of all the wells showing no amplification.

FIG. 18A. Raw fluorescence images of real-time RT-LAMP with tissue on chip at four different time points. FIG. 18B. Fluorescence bar graphs of the raw images showing a differential increase in fluorescence over time. The gain in fluorescence over time is calculated taking time=0 image (initial) as the reference. FIG. 18C. Spatial threshold analysis showing the spatially mapped threshold times. Note that the tissue boundaries are maintained during reaction. Threshold time=0 refers to blanks. FIG. 18D. Amplification curves for all wells after curve fitting.

FIG. 19A. Raw fluorescence image at time 0 showing regions with and without tissue. FIG. 19B. Processed image with numbered wells (FIG. 19C). FIG. 19D. Raw amplification curves for marked regions showing that the positive wells (with tissue) amplify while the negatives (without tissue) don't and also that the tissue boundary remains preserved during amplification.

FIG. 20A. Raw fluorescence images of real-time RT-LAMP with tissue on chip at four different time points. FIG. 20B. Fluorescence bar graphs of the raw images showing a differential increase in fluorescence over time. The gain in fluorescence over time is calculated taking time=0 image (initial) as the reference. FIG. 20C. Spatial threshold analysis showing the spatially mapped threshold times. Note that the tissue boundaries are maintained during reaction.

Threshold time=0 refers to blanks. FIG. 20D. Amplification curves for all wells after curve fitting.

FIGS. 21A-21D. On-chip RT-LAMP 500 um wells. FIG. 21A. Raw fluorescence image at time 0 showing regions with and without tissue. FIG. 21B. Processed image with numbered wells (FIG. 21C). FIG. 21D. Raw amplification curves for marked regions showing that the positive wells (with tissue) amplify while the negatives (without tissue) don't and also that the tissue boundary remains preserved during amplification.

FIGS. 22A-22K. Overall process flow schematic. FIG. 22A. LNCaP cells are injected into a mouse and prostate cancer xenograft obtained. FIG. 22B. Xenograft is resected and immediately frozen and embedded in optimal cutting temperature compound (OCT). FIG. 22C. A 7 um tissue cryosection is loaded onto our microchip. FIG. 22D. A cured PDMS block is loaded on top of tissue-chip assembly. FIGS. 22E-22F. The PDMS shears and partitions the tissue into small pixels at sharp well edges and pushes them into wells under centripetal force in a standard centrifuge. The pixelated tissue adheres to the silanized (APTES) well surfaces and the PDMS is removed. We call this process "Tissue pixelation" (Time=2 minutes). FIG. 22G. Post pixelation, the tissue is fixed with acetone (Time=10 minutes). A proteinase K digestion is performed after this to create a pathway for amplification enzymes to reach the target nucleic acids inside cells. (Time=30 minutes). FIG. 22H. RT-LAMP reagents are pipetted on chip in bulk (5 ul). FIG. 22I. Compressed air is blown on it at an angle inside mineral oil. FIG. 22J. Excess reagents are sheared away and fluid only inside wells is retained due to capillary forces. In the above steps, picoliter volume RT-LAMP reagents (~175 pL/well) are loaded onto the chip through a rapid instrument-free technique we call "bulk picoliter reagent loading". (Time=2 minutes). FIG. 22K. Quantitative gene expression is visualized through real-time imaging of the amplification reaction in each well performed using only a hot plate at 65 C and a fluorescence microscope. (Time=45 minutes).

FIG. 23A. Amplification curves and standard curve of the TOP2A mRNA RT-LAMP with purified total RNA extracted from LNCaP cells. $10^4$ cells had 940 ng of purified total RNA per reaction as measured with nanodrop spectrophotometer. FIG. 23B. Amplification curves and standard curve of the RT-PCR assay for TOP2A mRNA performed using previously published primers[21]. Our RT-LAMP assay can detect TOP2A mRNA from a single cell in reaction tube, whereas the RT-PCR assay can detect mRNA from only up to 100 cells (~9.4 ng total RNA) in a reaction tube (25 ul per reaction). The amounts of RNA per reaction for each dilution was the same as in RT-LAMP (FIG. 23A) to allow direct comparison. FIG. 23C. Amplification curves and standard curve of the TOP2A mRNA RT-LAMP assay with whole cells spiked directly into the reaction tubes. TOP2A down to a single cell could be reliable amplified.

FIGS. 24A-24D. SEM characterization after tissue pixelation. Tissue partitioning and division into small pixels can be clearly visualized as tissue seen inside the wells. The blue box in FIG. 24A is shown in FIG. 24B and the blue box in FIG. 24B is shown in FIG. 24C and FIG. 24D. FIGS. 24E-24F. DAPI-fluorescence imaging of the same pixelated tissue showing nuclei inside the well boundaries. FIG. 24F shows the region in yellow box in FIG. 24E. FIGS. 24G-24H. Characterization after bulk picoliter reagent loading in tissue loaded wells. Fluorescent rhodamine dye was filled in the wells for characterization of cross-over across wells. FIG. 24G shows the low magnification image of dye filled tissue (*) and no-tissue (**) regions and FIG. 24H shows the high magnification image of a dye filled region (shown in yellow box in FIG. 24G) with tissue. Well edges are seen as dark lines showing that they are above the fluid level and there is no overflow between adjacent wells. Partially filled wells indicated by a lower fluorescence were a small fraction of total wells on chip and confined to the chip boundaries as shown in FIG. 7A.

FIGS. 25A-25E. On-chip RT-LAMP: Cancer vs non-cancer control. FIG. 25A. Raw fluorescence images of real-time RT-LAMP with prostate cancer tissue on right and non-cancer (mouse skeletal muscle) tissue on left of chip at four different time points (*Non-cancer, **Cancer). FIG. 25B. Fluorescence bar graphs of the raw images showing a differential increase in fluorescence over time. The gain in fluorescence over time is calculated taking time=0 image (initial) as the reference. Note the amplification occurring only for the cancerous tissue. FIG. 25C. Spatial threshold analysis showing the spatially mapped threshold times. Threshold time=0 refers to blanks. FIG. 25D. Raw amplification curves of a row showing positive and negative wells. FIG. 25E. Fluorescence curves for all wells after curve fitting.

FIG. 26A and FIG. 26B show two sets of serial sections. For each set, on-chip RT-LAMP is performed on section 1 (1-2) and mRNA FISH is performed on section 2 (3-4). 1. Baseline-subtracted fluorescence images of real-time RT-LAMP with tissue on chip at three different time points showing the increase in fluorescence over time. 2. Spatial threshold analysis showing the spatially mapped threshold times. Threshold time=0 refers to wells which are not amplifying. 3. DAPI (blue) and TOP2A mRNA FISH (red) images of the consecutive section showing spatial heterogeneity in TOP2A mRNA expression. 4. Pixelated intensity map of mRNA FISH fluorescence. The spatial pattern of TOP2A expression is similar between the two assay types.

FIG. 27. Optical image of the chip beside a quarter. The dark region in the chip is the array of microwells.

FIGS. 28A-28E. SEM characterization of rat heart tissue pixelation. Tissue partitioning and division into small pixels can be clearly visualized as tissue inside the wells. The blue box in FIG. 28A is shown in FIG. 28B and the blue box in FIG. 28C is shown in FIG. 28D. FIG. 28E shows pixelated tissue inside a single well.

FIG. 29A. Raw fluorescence image at time=0 showing regions with and without tissue. FIG. 29B. Zoomed in processed image with numbered wells. The inset shows the entire processed image. FIGS. 29C-29D. Raw amplification curves for marked regions (blue and green) showing that the positive wells (with tissue) amplify while the adjacent negative wells do not. The tissue boundary remains preserved during the amplification reaction confirming that there is no cross talk between adjacent wells. FIG. 29E. Representative amplification curve with sigmoidal fit from a positive and negative well.

FIGS. 30A-30D. Specificity validation of TOP2A mRNA FISH in cultured cell lines. Fluorescence micrographs show nuclear stain (Hoechst; top row) and TOP2A mRNA FISH (Quasar 647; bottom row). FIGS. 30A-30B. TOP2A-negative mouse 3T3 fibroblasts and RAW 264.7 macrophages show no significant TOP2A mRNA FISH signal. FIGS. 30C-30D. TOP2A-positive human prostate cancer cell lines PC-3 and LNCaP show significant TOP2A mRNA FISH signal. The scale bar on the bottom right of each image is 25 micrometers.

DETAILED DESCRIPTION OF THE INVENTION

Figure 1:
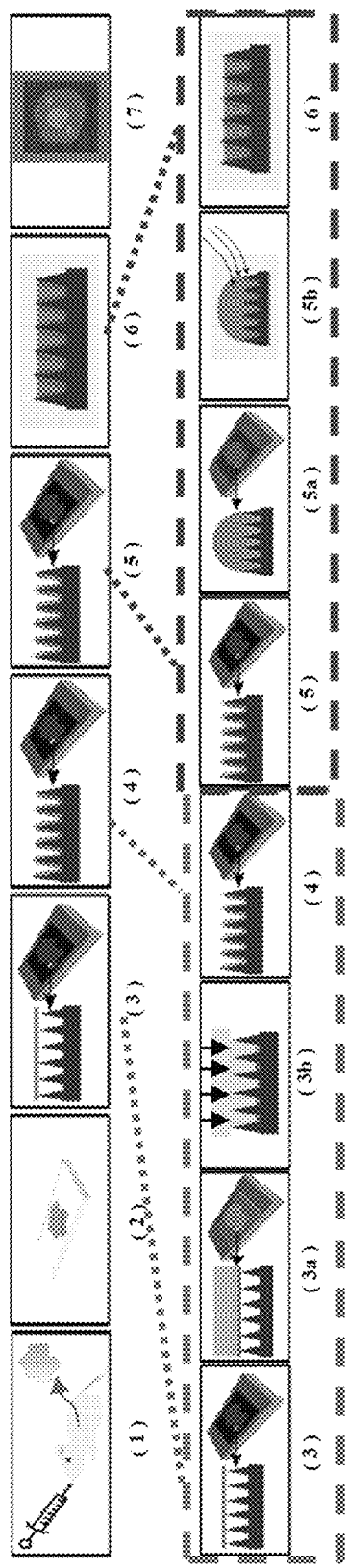
FIG. 1. Exemplary overall process flow schematic (top). LNCaP cells are injected into a mouse and prostate cancer xenograft obtained (1); Xenograft is immediately frozen after embedding in OCT (2); A 7 um tissue cryosection is loaded onto chip (3) and the tissue is "pixelated" and transferred into individual wells (4); Post pixelation, the tissue is fixed with acetone and treated with proteinase K (5); Picoliter volume RT-LAMP reagents are loaded onto the chip through a rapid bulk loading technique (6); Quantitative gene expression is visualized through real-time imaging of the amplification reaction in each well. Tissue pixelation process schematic (bottom blue box). A PDMS loaded on top of tissue-chip assembly (3a), the PDMS shears the tissue at sharp well edges and pushes into wells under centripetal force in a standard centrifuge. The tissue adheres to the silanized (APTES) well surfaces and the PDMS is removed. Reagent bulk loading process schematic (bottom red box). RT-LAMP reagents are pipetted on chip in bulk (5 ul) (5a) and compressed air is blown on it at an angle. (5b). Excess reagents are removed and fluid only inside wells is retained due to capillary forces.

In general, the terms and phrases used herein have their art-recognized meaning, which can be found by reference to standard texts, journal references and contexts known to those skilled in the art. The following definitions are provided to clarify their specific use in the context of the invention.

"Spatially mapping" is used broadly herein to refer to obtaining useful information about a tissue in a manner that is spatially preserved. Accordingly, the information may correspond to molecular information that spatially varies. In contrast, certain conventional assays simply provide a "reading", including presence/absence or magnitude from a tissue sample. The ability to read-out a signal in a spatially-preserved manner provides access to a number of useful applications, including spatial mRNA analysis of tissue, pathogen detection localization, and information that normally is associated with histological staining of proteins or only morphology of cells, including localization of mutated (e.g., cancerous) cells with attendant tumor shape characteristics and spreading information. Spatial mapping may be used to detect or read nucleic acid molecules and genes. Accordingly, the spatial mapping methods and devices provided herein provide a useful platform for cells and pathogen detection/analysis, tissue research, 3-D modeling of gene expression, and is readily compatible with any amplification methods, including nucleic acid amplification. Such gene mapping and analysis can occur in relatively short run-times, such as less than about 2 hours.

"Array" refers to an ordered placement of wells to provide the desired pixelation of tissue into a plurality of tissue islands. Each tissue island can then undergo individual and simultaneous processing, such as for nucleic acid amplification. Such amplification accordingly occurs in a manner that is spatially preserved. Conventional amplification techniques, in contrast, generally occur in a manner that spatial information is lost. Accordingly, as used herein "well" broadly refers to a volume in which tissue can be confined, including in a manner to ensure there is no or minimal cross-talk between wells. That is, tissue or target analyte does not significantly pass between wells. Such unwanted cross-talk would adversely impact spatial information and spatial sensitivity.

As used herein, "substrate" refers to a material, layer or other structure having a surface, such as a receiving surface, supporting one or more components or devices including an array or microarray. Arrays may be embedded in substrates so that the array is formed within and made the same material as the substrate. Arrays embedded in substrate may be manufactured from a single piece of material. Substrates which may be useful in the methods and devices described herein include silicon, glasses, metals, insulators and/or dielectrics. Substrates may be composite materials. The substrate and/or supported array may also be referred herein as a chip.

"Deformable substrates" are substrates having sufficient elasticity such that they deform under an applied force and relax back to or nearly their undeformed shape upon removal of the applied force. Materials useful as deformable substrates include polymers, for example, PDMS, SU-8, PEG, and photoresists.

"Array" refers to material or device having a number of wells, receiving chambers, void spaces or is otherwise configured to hold a number of tissue samples. Microarrays refer to wells that have at least dimension that is less than 1 mm. An array may have any number of wells and may be provided in various configurations including a grid, as described herein. Wells useful in the described arrays may have any geometric shape including inverted pyramids, cones, and rounded bottom wells with circular, square or polygonal cross-sections. Arrays may be described in terms of one or more dimensions (e.g. depth, width), volume and/or shape. Microarrays may have greater than or equal to 1000 individual wells, greater than or equal to 2500 wells, or optionally, greater than or equal to 5000 wells, depending on the desired spatial resolution. "Spatial resolution", accordingly, is directly correlated to the spacing between wells and the well footprint size. As wells are more tightly spaced, the spatial resolution increases. Any of the methods and devices provided herein, may have a spatial resolution as high as 1 µm, 10 µm or 100 µm. Spatial resolution refers to the minimum distance at which reliable differences arising from tissue-differences within the tissue sample are detectable. Depending on the application of interest, the spatial resolution is correspondingly tailored, with relative large well footprint surface areas and volumes for those applications not requiring high spatial-sensitivity and where large tissue sample volumes are desired. In contrast, for applications where detailed differences over small regions are desired, the array may have relatively small surface area footprint and/or volume, so fine differences over short distances are detectable.

"Shearing surface" is a surface positioned between two or more of the wells that is capable of severing, cutting or otherwise shearing a tissue sample into more than one piece when the tissue sample is forced into the shearing surface. Shearing surfaces may be configured as to form the walls, edges or boundaries of the wells of a microarray. Shearing surfaces may be defined as their cross-sectional width at or near the point of contact with a tissue sample. For example, shearing surfaces may have a width of less than or equal to 5 µm, or optionally, less than or equal to 2.5 µm. The shearing surface may also be described as having a relatively high slope and appropriate depth, both to ensure the tissue is reliably cut or sheared and that the cut or sheared tissue remains within the well and physically separated from adjacent wells. For example, the shearing surface may correspond to a well edge having a depth of between about 20 µm and 200 µm and an average slope of between about 0.5 and 1.5, or about 1, with the top of the well meeting at sharp-edged region where the slope changes from a positive to negative direction, such as over a sharp-edged distance that is less than or equal 5 µm, toward a sharp-point where the slope changes from a positive to negative direction over a distance that is less than 0.1 µm. Conceptually, the shearing surface may be continuous so as to sever the tissue sample into separate islands, with one unique island per well.

"Imaging" and/or "quantifying" is used broadly herein to refer to any method of analyzing a target analyte or biomarker, depending on the application of interest. For example, the amount or even presence/absence of a target nucleic acid in a tissue sample island. Imaging may utilize dyes, including fluorescent dies, or fluorescently labeled tags, with any imaging device such as a camera, electrical device or computer to quantitatively (e.g. measuring intensity) or qualitatively determine the amount of nucleic acid in a sample. Imaging and/or quantifying includes electrically-based techniques, such as implementing FETs and/or ISFETs, to measure nucleic acid presence, quantity or concentration.

"Polymerase chain reaction" (PCR) is a commonly used technique that enzymatically replicates targeted portions of nucleic acids which uses thermal cycling for example to denature, extend and anneal the nucleic acids to amplify the amount of a nucleic acid sample analyzed by taking the sample through 3 temperature steps. These steps are for the annealing of the primer (lowest temperature), extension (the actual amplification, medium temperature) and denaturation of the product, which make up one cycle of the PCR. In each cycle the amount of nucleic acid is amplified twice the value before the cycle. By cycling many times, the nucleic acid at hand can be amplified orders of magnitude. Relevant measures include measurement of a PCR by-product, such as pH changes or hydrogen ion levels as hydrogen ions are generated as byproducts of the amplification reaction. For more specific amplification assessment, the measurement may relate to generated pyrophosphates whose generation is electrically detected, or a detection of the amplified DNA sequence, such as by a binding event to a surface that is electrically detected by the corresponding FET. See, e.g., U.S. Pat. Nos. 8,945,912, 9,433,943, incorporated specifically by referenced for the FET-based detection, including ISFET.

"Inert covering fluid" refers to layer of fluid selected to cover the array of wells and facilitates removal of excess fluid reagents, including by forcing air over the wells at a sufficient force to remove the excess liquids on top the wells, while the liquids in the well remain under a relatively higher capillary force or surface tension in the relatively small-dimensioned well.

EXAMPLE 1

RT-LAMP Analysis of Prostate Cancer

Described herein is an on-chip spatial gene expression analysis technique that can perform real-time nucleic acid amplification, including reverse transcriptase loop mediated isothermal amplification (RT-LAMP) starting from tissue samples, while keeping the native spatial location of the nucleic acid preserved. We engineered a silicon oxide chip with an array of microwells that serve as independent picoliter volume RT-LAMP reaction vessels. The wells were designed to have knife-like sharp edges (referred herein as a "shearing surface") that help in tissue partitioning-and-transfer into wells starting from a tissue cryosection. A capillary action based reagent loading technique was developed to fill all the wells on the chip simultaneously while preventing reagent overflow between wells in the final loaded chip. Using this platform we amplified the TOP2A mRNA starting from a 7 micron tissue section of a prostate cancer xenograft and visualized the variation in amplification threshold times across the tissue.

The example described herein eliminates all of the drawbacks described above by use of a tissue cryosection as a starting tissue sample, requires minimal sample processing and performs parallel picoliter reverse transcription loop-mediated isothermal amplification (RT-LAMP) reactions in an array of wells (volume~175 pL) with tissue in them. The native spatial distribution of nucleic acid in tissue is preserved throughout the process.

RT-LAMP: Loop-mediated isothermal amplification (LAMP) overcomes the dependence on expensive equipment (via elimination of thermocycling and the requirement for machine-based result detection) while amplifying DNA or RNA rapidly and specifically. Notomi et al., Nucl. Acids Res. 28:E63 (2000); U.S. Pat. No. 6,410,278. Because of the advantage in rapid, efficient, and specific amplification of small amounts of DNA and RNA, LAMP has emerged as a powerful tool to facilitate genetic testing for the rapid diagnosis of viral and bacterial infectious diseases in clinical laboratories. A novel nucleic acid amplification method, known as reverse transcription loop-mediated isothermal amplification (RT-LAMP), has been recently used for detection influenza A virus, Newcastle disease virus, classical swine fever virus and porcine reproductive and respiratory syndrome virus (Notomi et al, Nucleic Acids Res. 2000 Jun. 15; 28(12):E63; Pham et al., J Clin Microbiol. 2005 April; 43(4):1646-50; Chen et al., Mol Cell Probes. 2009 April; 23(2):71-4.)

The substrate can be any material, including, but not limited to, silicon glass, metal, insulator, and dielectrics.

The chip or microarray can be used for analyzing different sample types such as cells, and for differentiating and quantifying different cell populations on a chip based on their genetic markers/make-up.

The sensing modality of the PCR products can include, but is not limited to, fluorescent, mechanical and electrical. For example, the technique can be combined with field effect transistors (FETs) and the amplification reaction can be detected electrically via a change in pH or a mechanical signal from QCM or MEMS cantilever.

The described methods and devices can also be coupled with histological or immunostaining prior to amplification and thus a protein level analysis is possible in addition to the nucleic acid analysis.

LAMP is an exemplary amplification reaction from tissue that is robust against inhibitors such as cellular debris or blood which usually inhibit a PCR reaction. LAMP uses 4-6 primers which identify 6-8 regions on the template for amplification which makes it more specific than PCR.

Moreover, LAMP is isothermal so it only needs a portable heater to carry out the reaction, eliminating the bulky instruments required for PCR. We designed fingernail sized silicon oxide—on-silicon chips with an array of 5625 inverted pyramidal wells having knife-like sharp distinct edges to carry out the reactions. Once the tissue is loaded onto our chip, it is partitioned and transferred inside the wells in a process we call "tissue pixelation". This is followed by tissue fixation, permeabilization, loading of wells with amplification reagents and final RT-LAMP reaction on-chip carried out on a hot plate. (FIG. 1).

We select prostate cancer tissue for this example. Despite being the most common cancer diagnosed in men and second leading cause of cancer death in the United States, accounting for more than 25,000 deaths annually according to 2015 cancer statistics [49], the molecular mechanisms fueling the prostate cancer pathogenesis remain relatively unknown. Topoisomerase II alpha (TOP2A), a nuclear enzyme involved in processes such as chromosome condensation and chromatid separation, has been shown to be upregulated with increasing Gleason score and with hormone insensitivity in prostate carcinoma [50]. The combination of prostate cancer xenografts grown in mice using LNCaP cell line and TOP2A mRNA were chosen to visualize the spatial mRNA variation within the xenograft tissue using our technique. With a rapid turn-around-time of 2 hours, starting from sample acquisition to RT-LAMP reaction, our low cost technique can perform spatially mapped nucleic acid amplification test (NAAT) in any basic laboratory with minimal facilities.

TOP2A mRNA RT-LAMP off-chip: Here, we characterize a sensitive and specific RT-LAMP reaction for TOP2A mRNA. Provided is a novel RT-LAMP reaction for amplifying TOP2A mRNA using 6 sequence specific primers. The details about the primer design are described herein, with specific sequences provided in the tables.

Figure 3A:
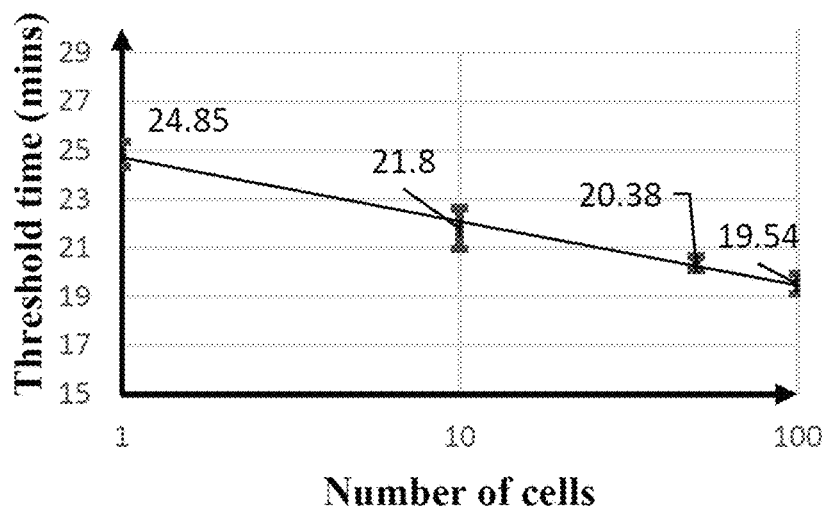
FIG. 3A. Standard curve for cells spiked in reaction. The standard curve shows a good linear fit. A single cell could be reliably detected.
Figure 3B:
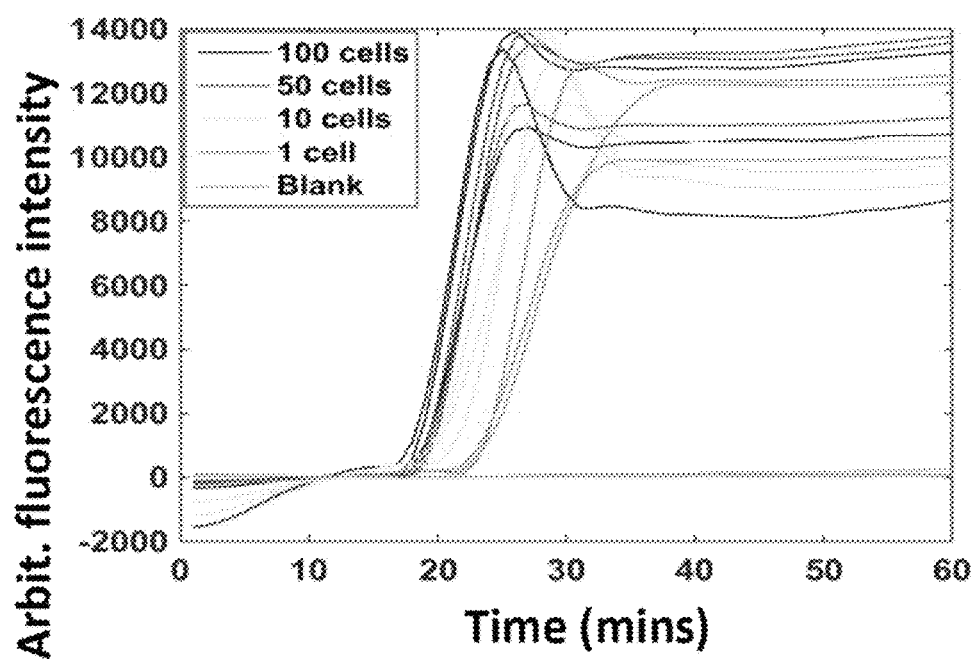
FIG. 3B. Raw thermocycler amplification curves for cells spiked in reaction. The standard curve shows a good linear fit. A single cell could be reliably detected.
Figure 10A:
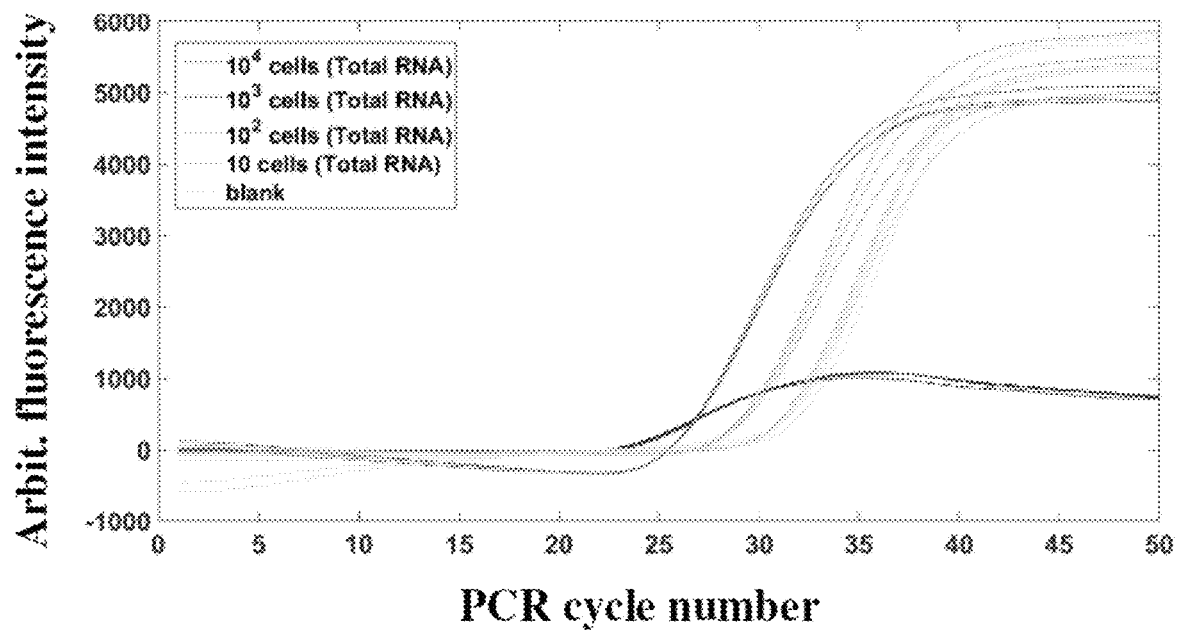
FIGS. 10A-10B. Raw thermocycler fluorescence data (FIG. 10A) and standard curve (FIG. 10B) of RT-PCR reaction for TOP2A with purified total RNA extracted from LNCaP cell. $10^4$ cells had 37.6 ng/ul concentration of purified total RNA per reaction as measured nanodrop spectrophotometer (same as for RT-LAMP reactions). In contrast with the RT-LAMP reaction, the RT-PCR reaction could only detect total RNA from a 100 cells equivalent. The blanks start to amplify after 30 cycles for this reaction. This shows the superiority our designed RT-LAMP assay for TOP2A over the existing RT-PCR assay.
Figure 10B:
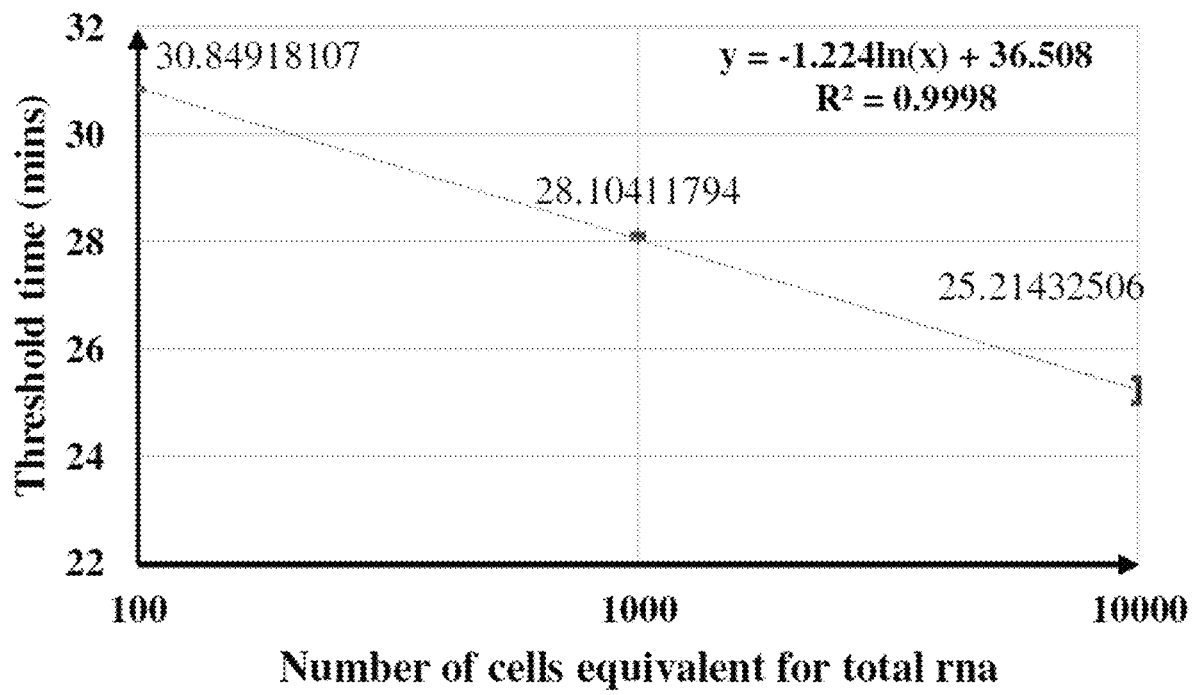

As a first characterization of the reaction, the off-chip ('tube-based') TOP2A RT-LAMP reaction is performed using purified total RNA from cells and tissue sections (FIGS. 13A-13D and FIGS. 14A-14B). The standard curve in both the cases showed a good linear fit ($R^2$=0.93 and 0.98 for total RNA from cells and tissue respectively). TOP2A from purified total RNA of 1 cell equivalent could be detected by our designed RT-LAMP reaction. We compared this reaction sensitivity with RT-PCR by performing reactions with the same RNA concentrations and previously published RT-PCR primers for TOP2A. As can be seen from FIGS. 10A-10B, the RT-PCR reaction was 2 orders of magnitude less sensitive and could only detect TOP2A from purified RNA of 100 cells equivalent. The next step was to test the robustness of our RT-LAMP reaction. We spiked 1 to 100 LNCaP cells directly in a 25 ul tube-based reaction and tested for amplification. (FIGS. 3A-3B). The figures show the amplification fluorescence curves and standard curve for 1, 10, 50 and 100 cells spiked in reaction. The reaction with a single cell could be reliably amplified. Together these data demonstrate the sensitivity, specificity and robustness of the RT-LAMP reaction for TOP2A mRNA.

Tissue pixelation and bulk reagent loading: To perform the RT-LAMP reaction on chip from tissue sample there are two unique preparatory steps required: 1. Tissue pixelation—Dividing the tissue cryosection on chip into small separated bits/pixels that are put into their corresponding underlying wells for downstream parallel and independent amplification reactions. 2. Bulk picoliter reagent loading—Loading the amplification reagents into the wells post tissue pixelation. The wells have a volume of ~175 pL and there are 5625 wells on a chip which need to be filled with reagents while making sure there is no overflow between any two wells. The schematic in FIG. 1 shows the tissue pixelation protocol. When the PDMS block is placed on top of the tissue and the whole assembly is exposed to centripetal force in a standard centrifuge, the flexible PDMS pushes its way into the wells, shearing the tissue at the well edges in the process. The tissue sticks to the pre-silanized (APTES) chip surface while the PDMS restores to its original shape in the absence of the force. We named this process "tissue pixelation" as a continuous cryosection disc (7 um thick) is divided into thousands of small pixels in this step. FIG. 2A shows the DAPI stained and SEM images of the tissue in wells after pixelation. The well edges can be clearly visualized as dark lines in the DAPI stained fluorescent images. These data show that the tissue is completely inside the wells after the pixelation step and the tissue partitioning into pixels is complete.

Figure 2B:
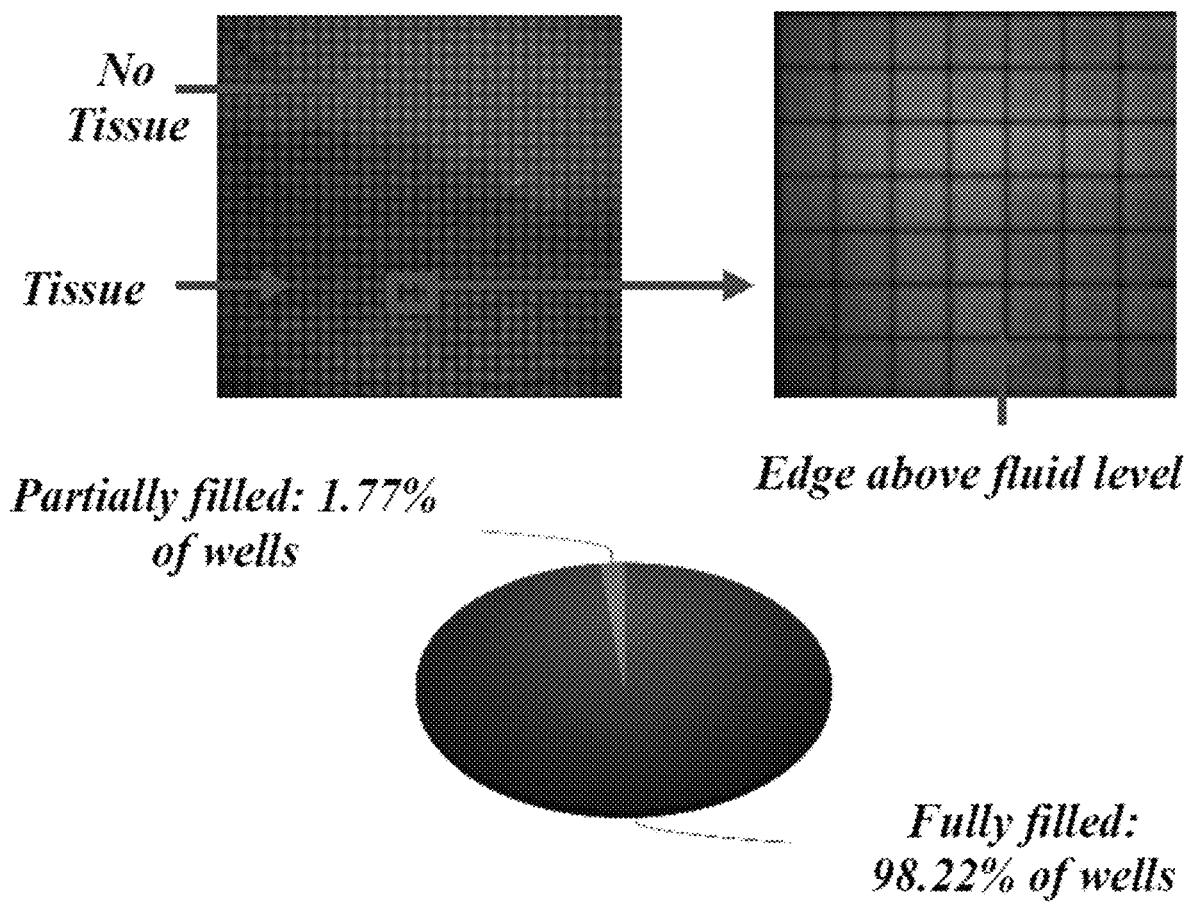
FIG. 2B. Chip characterization after bulk picoliter volume reagent loading in wells. Rhodamine dye was filled in wells for characterization. Well edges can be seen as dark lines showing that they are above the fluid level and there is no overflow between adjacent wells. Partially filled wells indicated by a lower fluorescence were a small fraction of total wells on chip and confined to the chip boundaries.
Figure 7A:
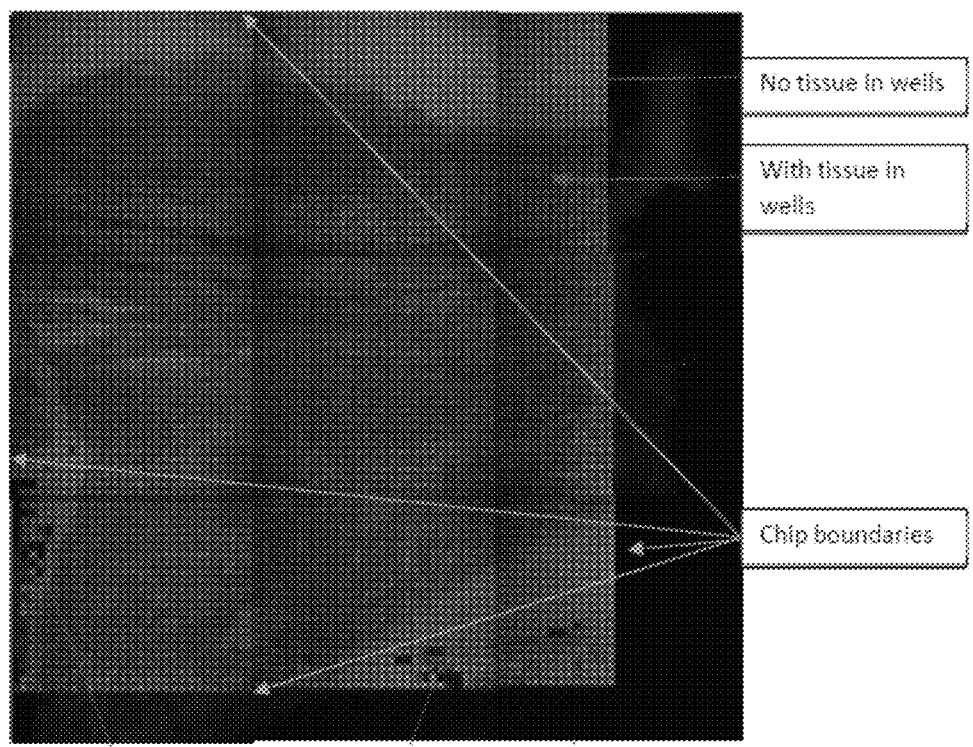
FIGS. 7A-7B. Bulk reagent loading characterization.
Figure 7B:
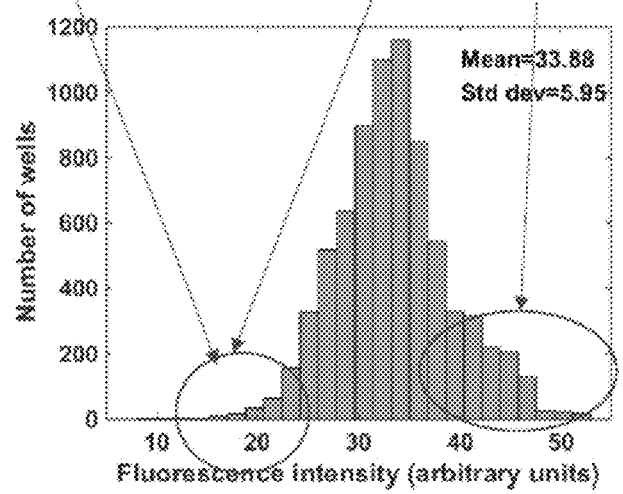
Figure 8A:
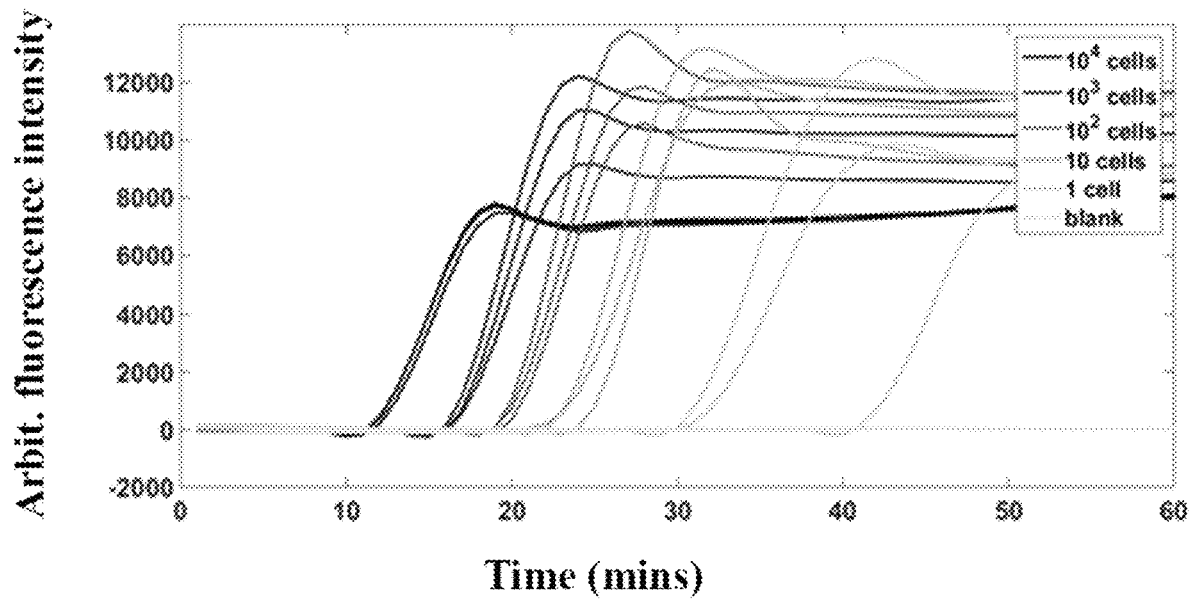
FIGS. 8A-8B. Raw thermocycler fluorescence data (FIG. 8A) and standard curve (FIG. 8B) of RT-LAMP reaction for TOP2A with purified total RNA extracted from LNCaP cell. $10^4$ cells had 37.6 ng/ul concentration of purified total RNA per reaction as measured nanodrop spectrophotometer. A good linear fit was observed in the standard curve and total RNA from 1 cell equivalent could be detected.
Figure 8B:
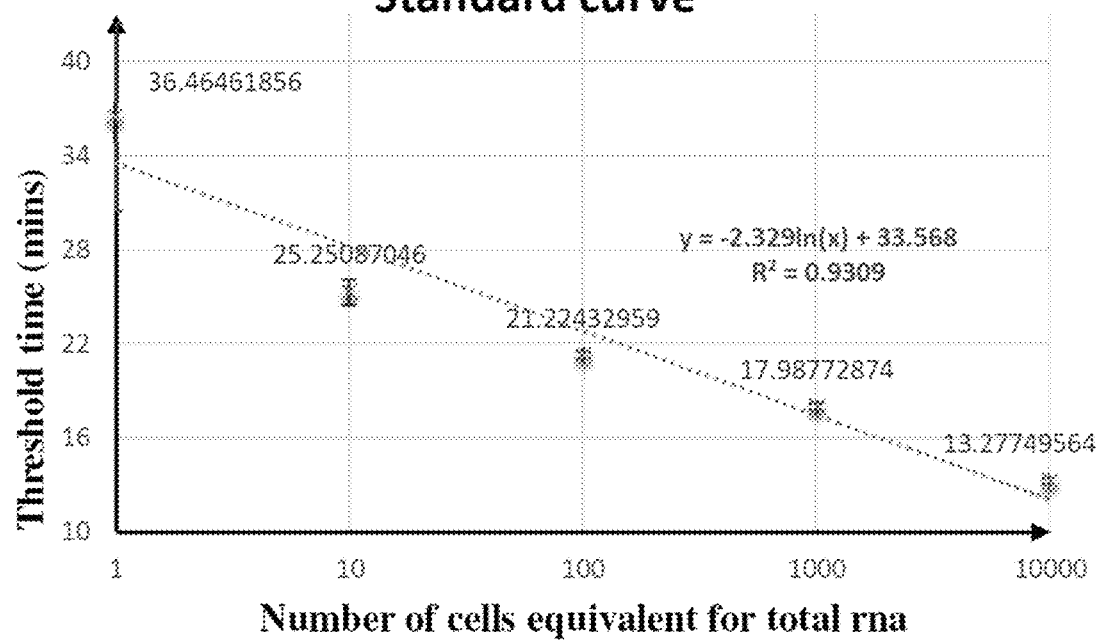

FIG. 1 panel (3) shows the bulk picoliter reagent loading protocol. After the reagents are pipetted in bulk (<5 uL), the whole chip (with tissue inside wells and pipetted reagents on top) is immediately immersed in mineral oil and compressed air is blown on it. With the mineral oil acting as an envelope for the reagents, the excess of reagents are sheared away due to air pressure while the capillary forces retain fluid only inside the wells. In this step, we filled 7225 wells with ~175 pL volume per well. There are a few commercial solutions for spotting arrays of nanodroplets but none of these can spot picoliter volumes in such close spacing. These commercial systems also have large dead volumes (milliliters of solution that are used to fill reservoirs but can't be used for droplets) and loading over 5000 wells using any such commercial micro-injector system would take hours. The bulk loading technique we showed here can be scaled to fill larger arrays with millions of wells using the same principle in a matter of 1-2 minutes. We used fluorescent rhodamine dye to characterize this process as shown in FIG. 2B. The figure shows the fluorescent images after filling the wells with the dye. The well edges are above the fluid level and can be seen as dark lines showing that there is no cross-talk between adjacent wells. Partially filled wells can be seen with lower fluorescence intensity and were seen only near the chip boundaries. FIGS. 7A and 7B show a histogram of well fluorescence distribution and complete chip data for fluorescence.

On-chip real time RT-LAMP reaction: To perform the real-time on chip RT-LAMP reaction we first fixed the pixelated tissue using acetone. Fixing the tissue in acetone takes only about 10 mins and stops the RNA degradation at room temperature. Acetone is a precipitative fixative and has been shown to provide good RNA yields for downstream amplification reactions. The tissue was then treated with proteinase K (5-10 mg/ml) for 30 mins. The pre-treatment of tissues with proteinase K digests the proteins in the cell membrane and makes them permeable to polymerase and reverse transcriptase enzymes. This allows the RT-LAMP reagents to penetrate the cells and carry out the amplification reaction. Both the above steps are standard in many biological protocols such as for in situ hybridization, or in situ PCR.

Figure 11:
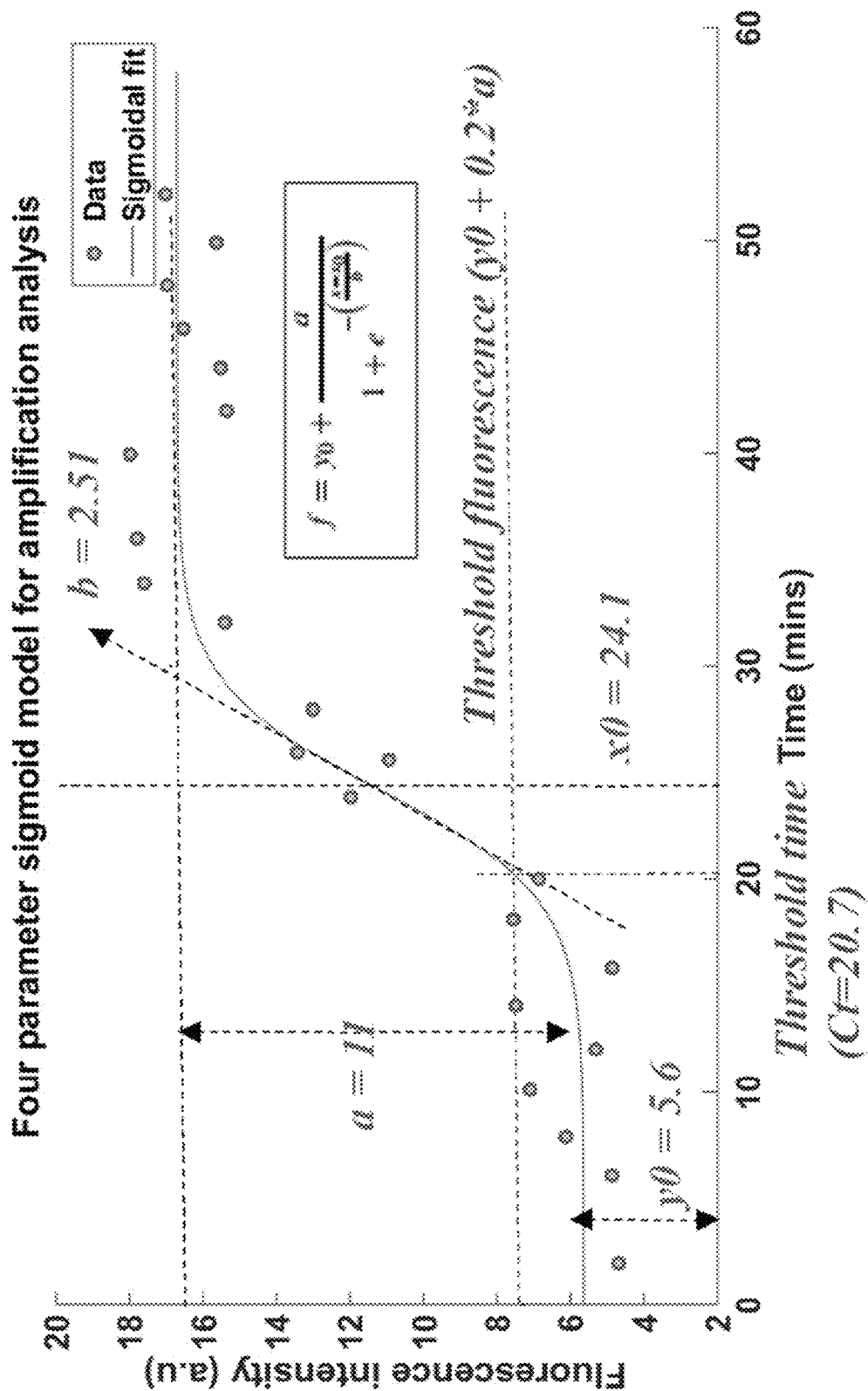
FIG. 11. 4 point parameter model used for sigmoidal fitting of the raw amplification curves. The equation for the sigmoidal fit is given in the red box inside the figure and the corresponding parameters are represented in the data fit shown as an example. The threshold time was taken as (yo+0.2*a) which is in line with our thermocycler threshold time calculation.
Figure 12A:
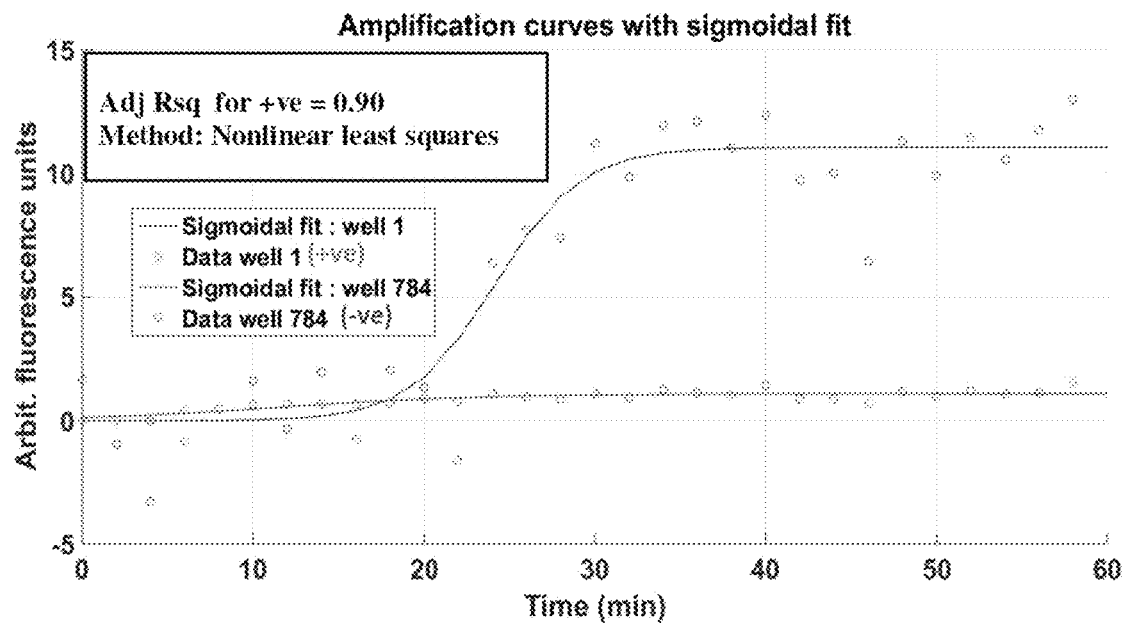
FIG. 12A. Curve fitting analysis showed for a positive and a negative well.
Figure 12B:
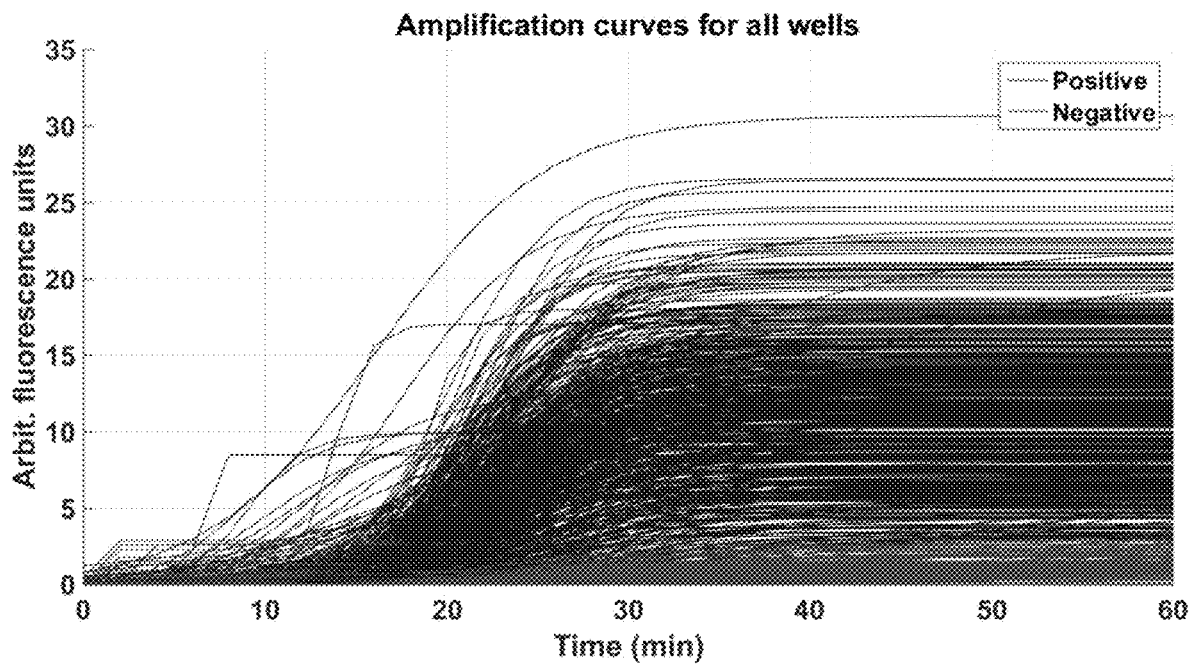
FIG. 12B. Amplification fluorescence curves for all wells.
Figure 14A:
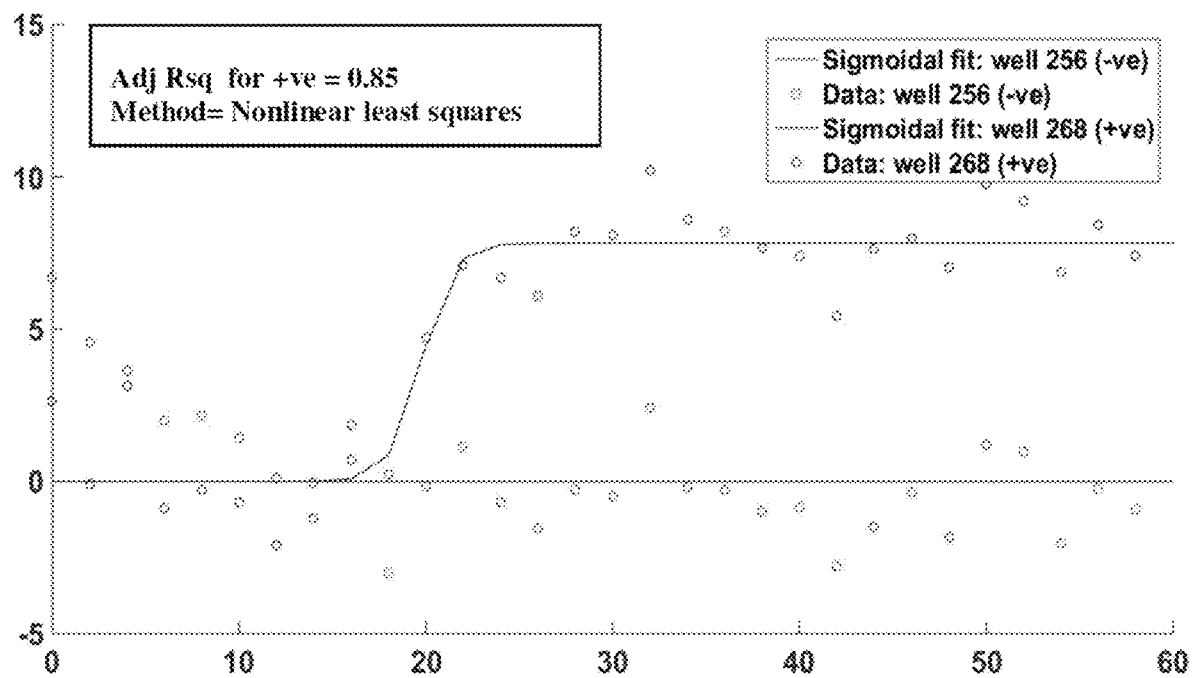
FIG. 14A. Curve fitting analysis showed for a positive and a negative well.
Figure 14B:
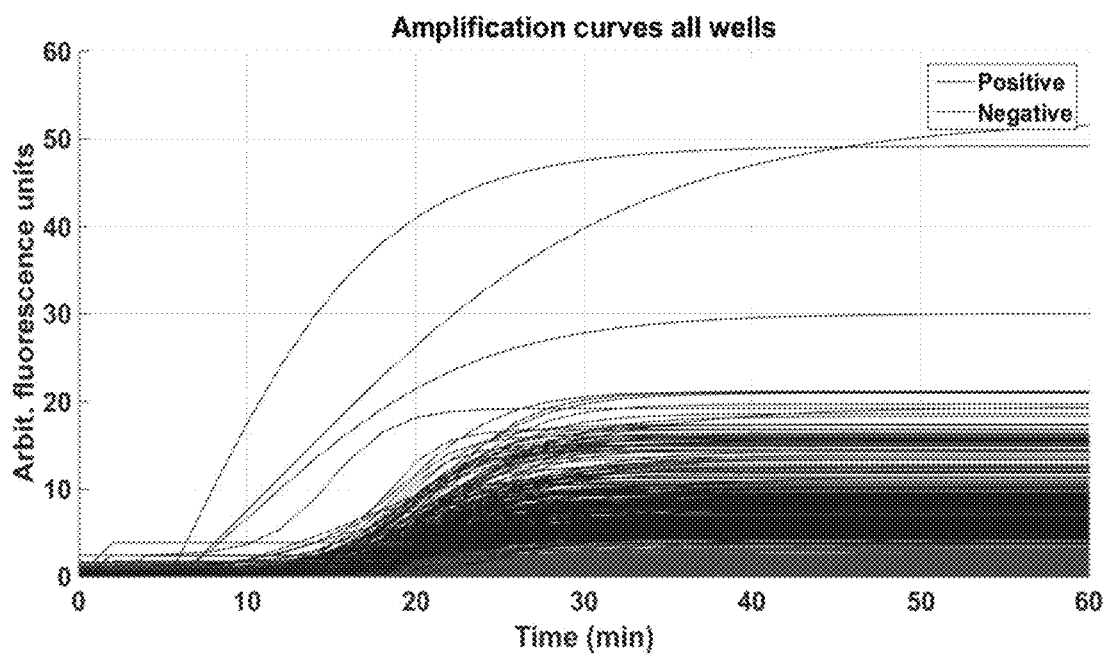
FIG. 14B. Amplification fluorescence curves for all wells.

After the above steps are performed, the tissue/chip is ready for the on-chip RT-LAMP reaction. The reagents were loaded using the previously described bulk reagent loading technique and the amplification reaction was carried out on a hot plate at 65 C, imaged every 2 mins using an Olympus BX51 fluorescence microscope. The on-chip amplification reaction was completed in 35 mins and the progressive product accumulation in each well was visualized as proportional increase in the fluorescence in the corresponding well. These real-time fluorescence curves were used to calculate the threshold times for each well. FIGS. 4A-4D show the raw fluorescence images at different time points, the differential spatial fluorescence bar graphs and the spatial threshold time analysis. A sigmoidal curve fitting was performed on the raw fluorescence curves and threshold time was calculated as shown in FIG. 11. FIGS. 12A-12B show the curve fitting parameters for this experiment and all amplification curves. Analyzing regions close to the tissue boundary showed that there was no crosstalk between adjacent wells (FIGS. 13A-13D). The raw amplification curves were found highly comparable to the ones obtained off-chip using the commercial thermocycler.

Figure 16A:
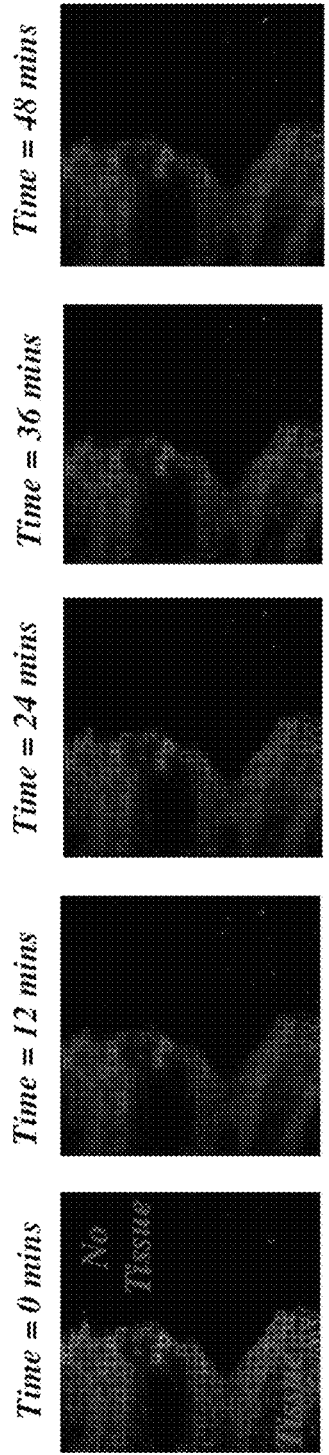
FIGS. 16A-16B. No primer on-chip negative control.
Figure 16B:
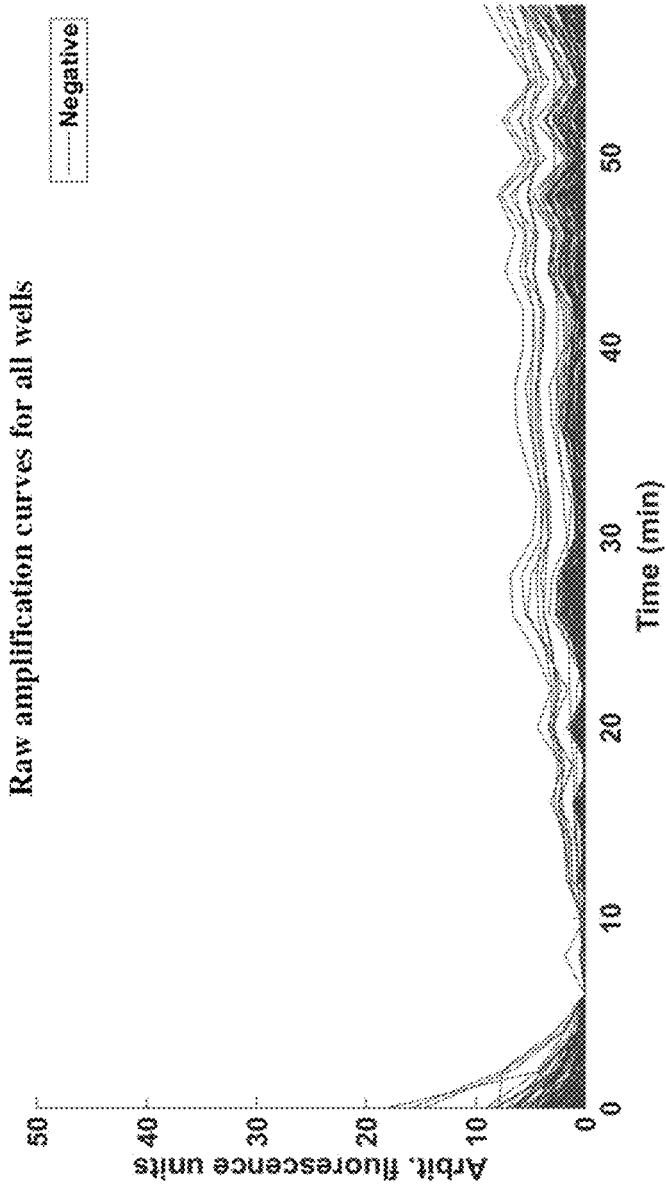
Figure 17A:
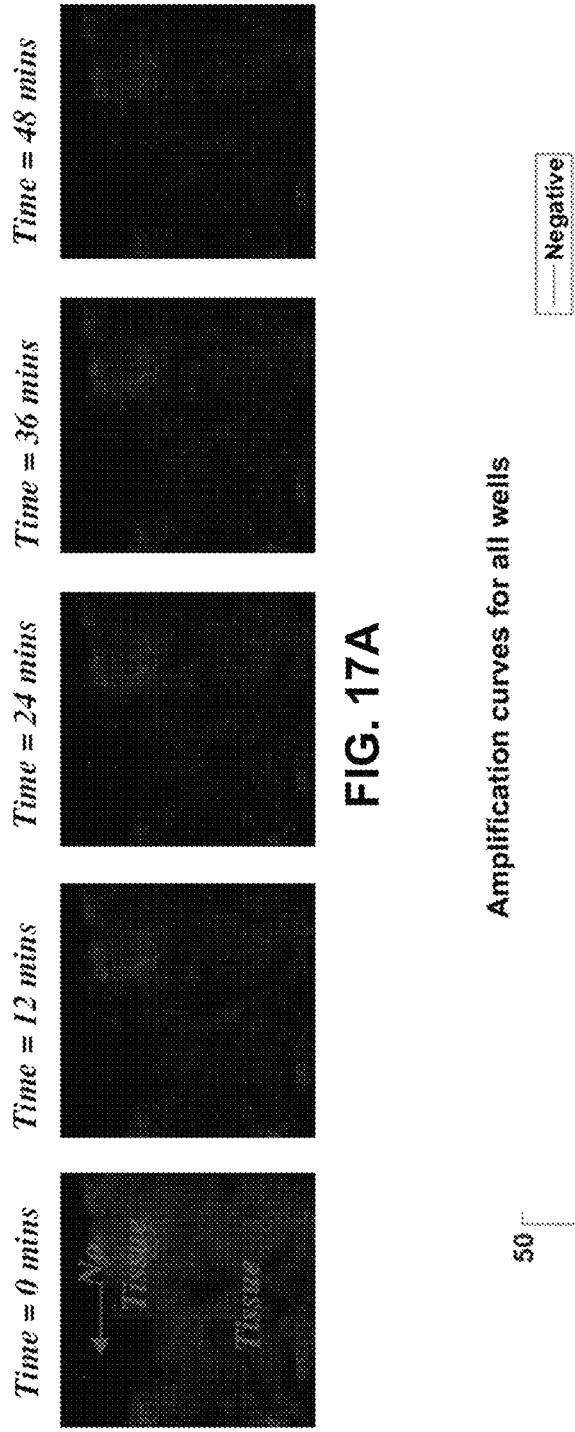
FIGS. 17A-17B. RNase treated-on-chip negative control.
Figure 17B:
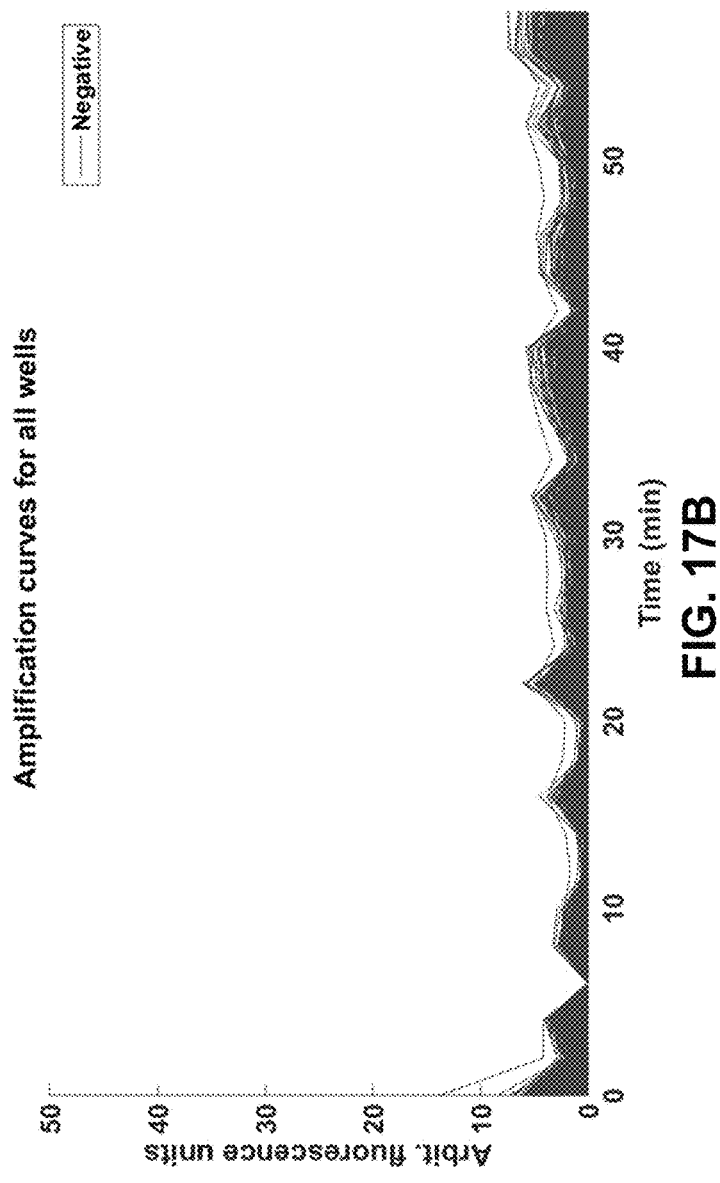
Figure 18A:
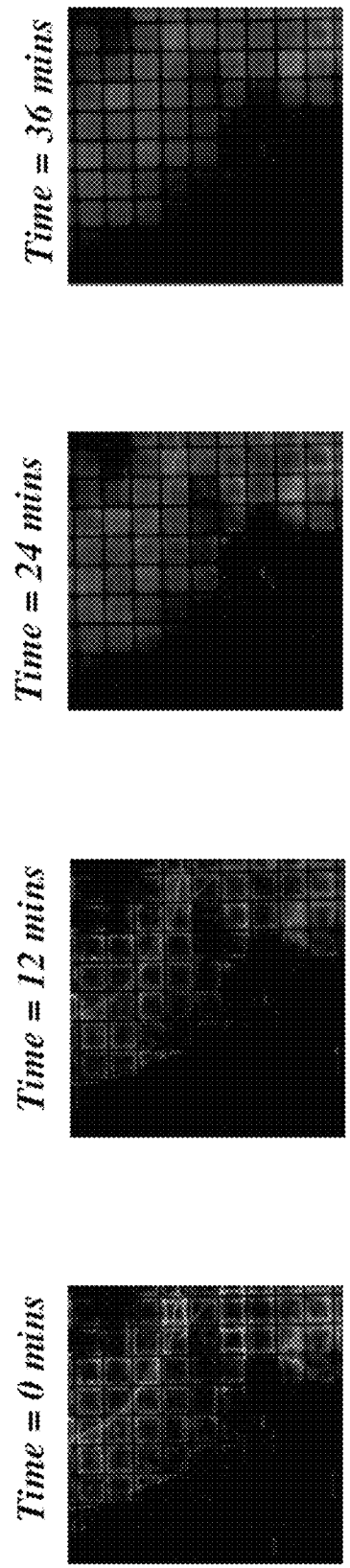
FIGS. 18A-18D. On-chip RT-LAMP 300 um wells.
Figure 18B:
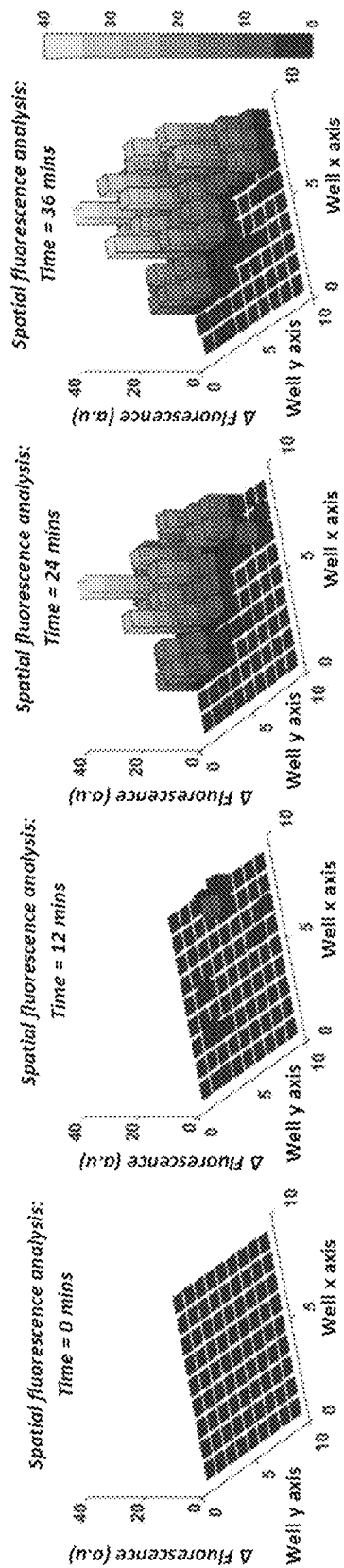
Figure 18C:
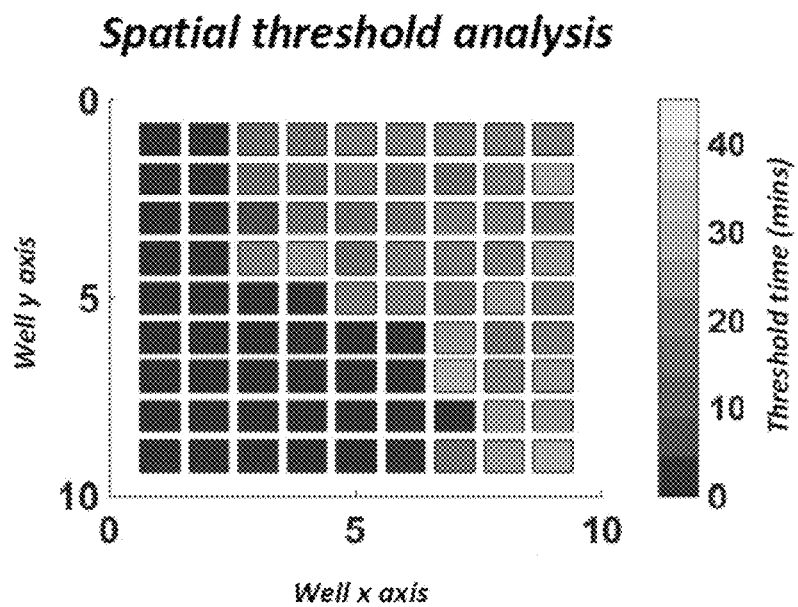
Figure 18D:
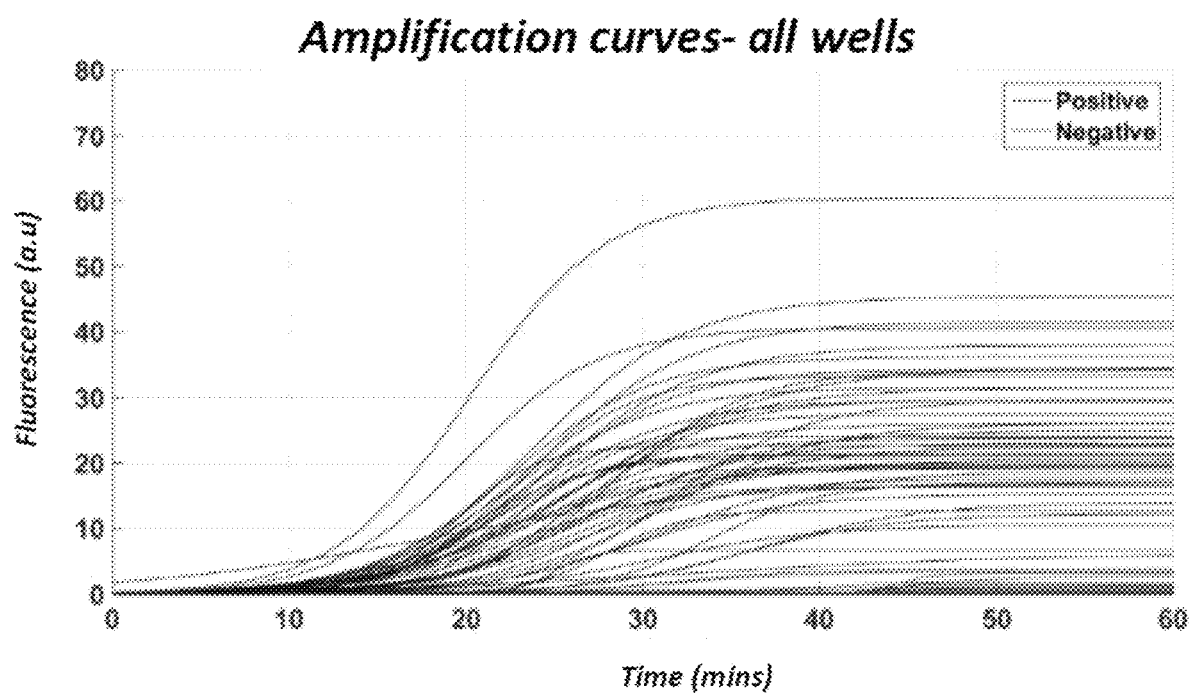
Figure 19B:
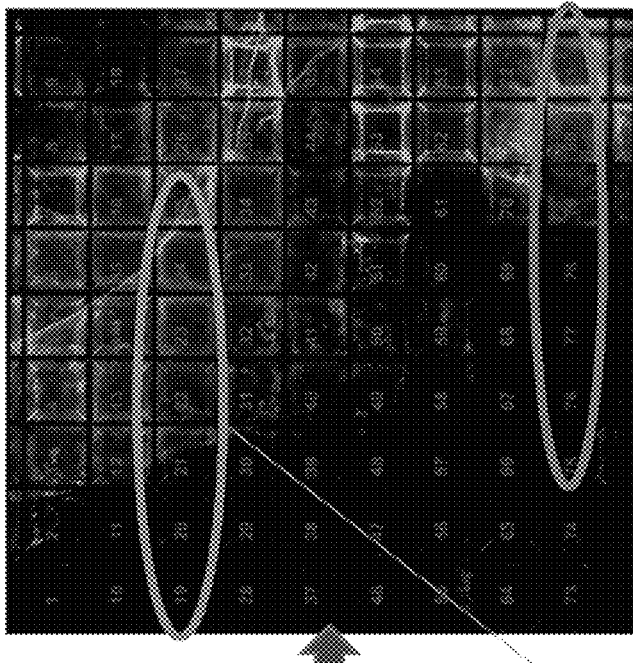
FIGS. 19A-19D. On-chip RT-LAMP 300 um wells.
Figure 19D:
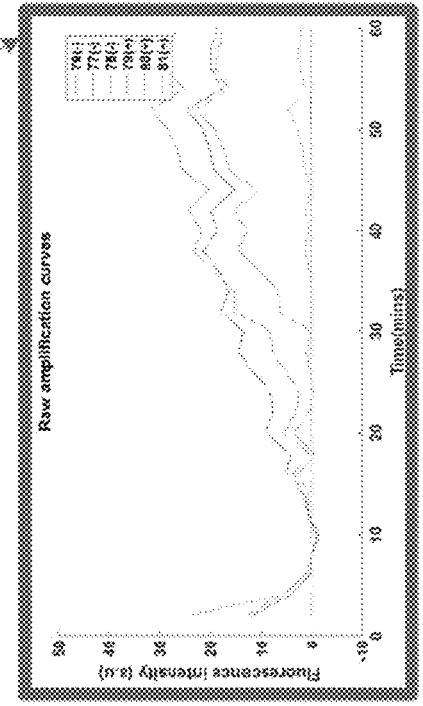
Figure 19A:
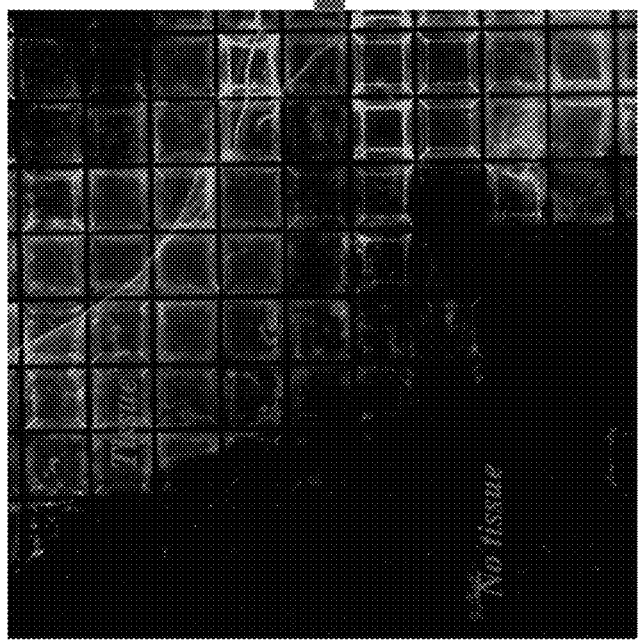
Figure 19C:
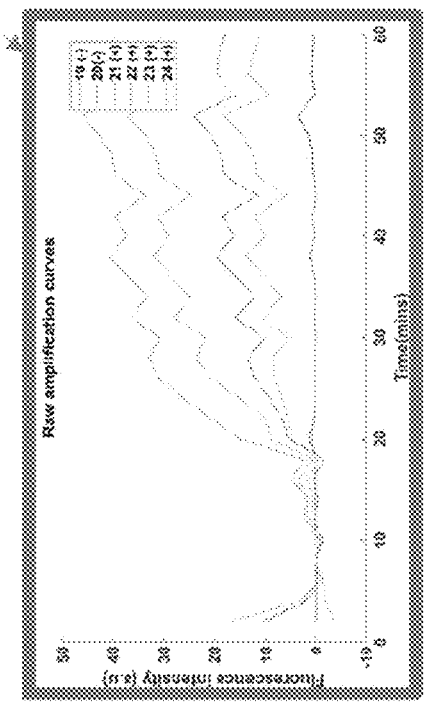
Figure 20A:
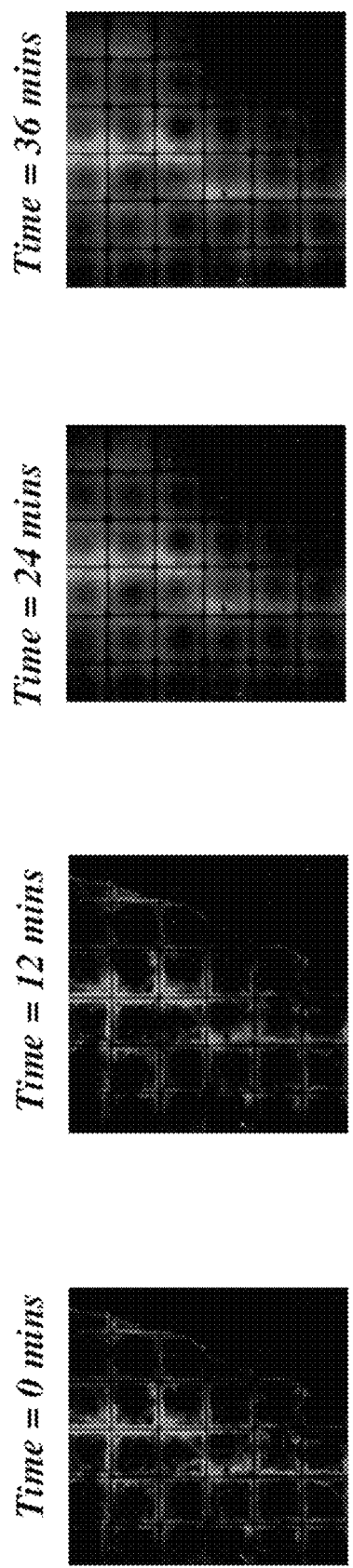
FIGS. 20A-20D. On-chip RT-LAMP 500 um wells.
Figure 20B:
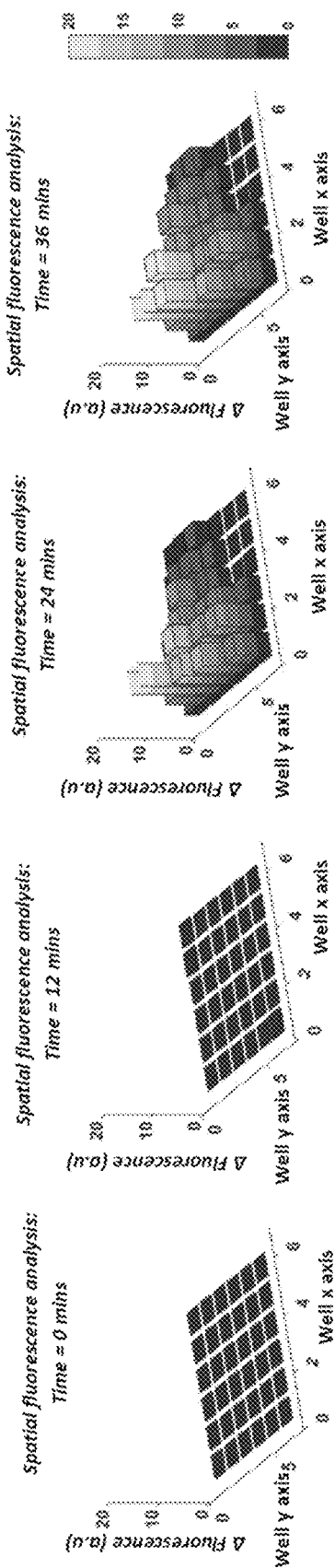
Figure 20C:
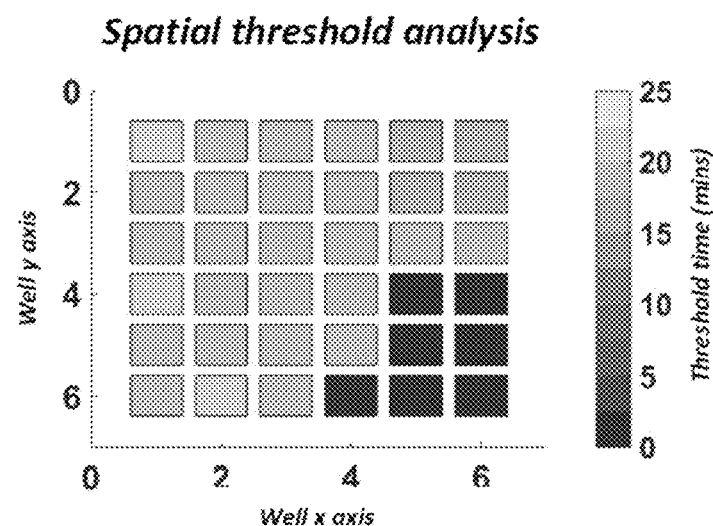
Figure 20D:
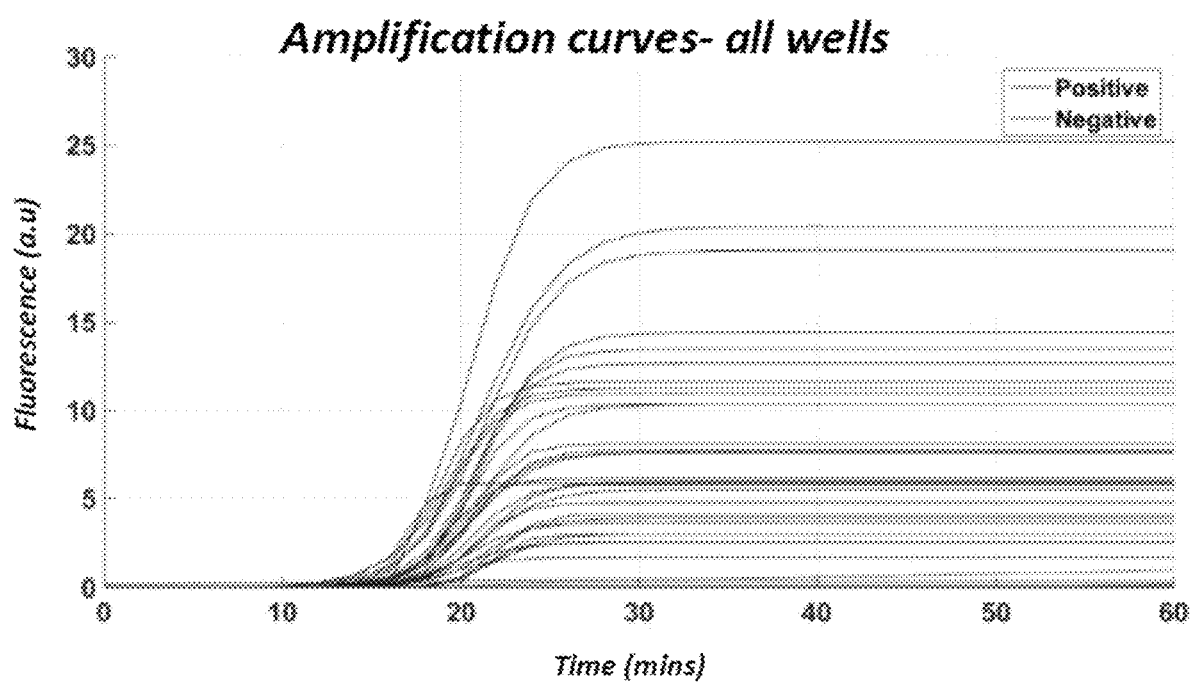

To ensure that the signal observed was not due to spurious/non-specific amplification, we performed a series of on-chip controls. In the first negative control, primers were omitted from the reaction mixture and no amplification was observed in the tissue (FIGS. 16A-16B). To test if the reaction is not amplifying genomic DNA, usually a no RT control is performed. Since BST polymerase itself has significant RT activity we performed an RNase digestion step using 100 ug/ml RNase A for 60 mins prior to amplification to degrade all the RNA. No amplification was observed in this case (FIGS. 17A-17B). As a final test for the specificity of the reaction on chip, cancer and non-cancer (mouse skeletal muscle tissue) tissue were loaded on the same chip and the reaction was performed. FIGS. 5A-5D show that only the cancerous tissue amplified validating the specificity of our on-chip assay. As the field-of-view reduces for higher magnification objectives, we could only image 784 wells for all the real-time on-chip measurements.

We harnessed the sensitivity, specificity and robustness of a LAMP reaction and combined that with basic micro fabrication techniques to deliver a technique that is simple and easy to perform, has a rapid overall run time of less than 2 hours and has the ability to quantitate. The process, which currently requires only a fluorescent microscope and a hot plate to carry out can be easily integrated into a completely portable setup using a smartphone and in-built heater making the technique accessible to even labs without a microscope. We demonstrated the sensitivity of the LAMP reaction off-chip for TOP2A down to a single cell spiked in tube while the theoretical sensitivity of the LAMP reaction goes down to a single molecule. The fluorescence curves for on-chip experiments look comparable to the off-chip thermocycler fluorescence curves. This is the first demonstration of on-chip picoliter RT-LAMP reactions with tissue in them.

The size of the chip and well are both variable and can be designed and fabricated depending on the number of samples to be analyzed simultaneously on a chip and the resolution required. We demonstrated on-chip amplification for 300 and 500 um well sizes apart from the standard 100 um well size. (FIGS. 18A-18D, 19A-19D, 20A-20D and 21A-21D). With the advent of multiplexing in LAMP, internal control (housekeeping gene) can be incorporated in each well and the gene expression data can be normalized accordingly for a more accurate interpretation. The functional benefit of the instantly described technique addresses a number of problems associated with conventional prior techniques, as summarized in Table 1.

TABLE 1

Comparison to prior techniques.

| Prior Technique | Problems |
| --- | --- |
| In situ hybridization | Low sensitivity, long run times |
| In situ PCR | Non-quantitative, long run times, poor reproducibility |
| Laser Capture Microdissection followed by qPCR | Long sample acquisition times, purification times, resource intensive, only small regions analyzed at a time |

EXAMPLE 2

Pixelated Spatial Gene Expression Analysis from Tissue

Described herein is a rapid technique that performs on-chip picoliter real-time reverse transcriptase loop mediated isothermal amplification (RT-LAMP) reactions on a histological tissue section without any analyte purification while maintaining the native spatial location of the nucleic acid molecules. This example includes a method of amplifying TOP2A messenger RNA (mRNA) in a prostate cancer xenograft with 100 μm spatial resolution and by visualizing the variation in threshold times across the tissue. The on-chip reaction was validated through fluorescence mRNA in situ hybridization (ISH). The entire process, from tissue loading on microchip to results from RT-LAMP can be carried out in less than two hours. This technique with its ease of use, fast turnaround, and quantitative outputs is an invaluable tissue analysis tool for researchers and clinicians in the biomedical arena.

The spatial localization of gene expression can unravel important insights into tissue heterogeneity, functionality and pathological transformations, but the ability to maintain this spatial information remains an enduring challenge in tissue sections routinely used for pathology. Amplification-based spatial gene expression analysis methods provide good sensitivity and specificity but decouple the analyte isolation and biochemical detection steps, making them low throughput and laborious[1-3]. Direct probe-based hybridization techniques such as single molecule FISH allow direct visualization of single RNA molecules in their native cellular context but off-target binding of FISH probes and cellular auto-fluorescence become a limiting factor in imaging tissue samples[4-7]. Methods performing spatially-mapped transcriptome analysis on a tissue section can identify multiple targets simultaneously but they must trade-off between the histologic reference and the quality of recovered biomaterials as staining and manual identification are often needed[8]. Also, since they utilize RNA-sequencing platforms, it makes them very resource intensive and expensive to perform[8-11]. These constraints limit the translation of the above methods into routine research and clinical practice.

Here, we introduce a technique which improves upon these drawbacks by analyzing a starting sample of tissue cryosection and performing parallel picoliter RT-LAMP reactions with minimal sample processing. LAMP is an isothermal reaction which has been shown to be robust against inhibitors in tissue that inhibit a PCR reaction[12]. It uses 4-6 primers which identify 6-8 regions on the template for amplification which makes it more specific than PCR[13]. We designed fingernail-sized silicon oxide-on-silicon chips with an array of 5,625 inverted pyramidal ~175 pL wells having knife-like sharp distinct edges to carry out the reactions (FIGS. 27 and 6A-6C). Once a tissue cryosection is loaded onto our chip, it is partitioned and transferred inside the wells in a process we call "tissue pixilation," also referred herein as "tissue islands." This tissue pixilation process which divides a solid tissue section into small tissue pixels takes less than 2 minutes. This is followed by tissue fixation (10 minutes), permeabilization (30 minutes), loading of wells with amplification reagents (2 minutes), and finally on-chip RT-LAMP reaction on a hot plate (45 minutes) (FIGS. 22A-22K). The native spatial distribution of nucleic acid in tissue is preserved throughout the process.

This example utilizes frozen sections of human prostate tissue xenografts grown in mice. Prostate cancer is the most commonly-diagnosed cancer in men and is the second leading cause of cancer death in men in the United States, accounting for more than 25,000 deaths in 2015[14]. The molecular mechanisms fueling prostate cancer pathogenesis remain relatively unknown[15-19]; however, topoisomerase II alpha (TOP2A), a nuclear enzyme involved in chromosome condensation and chromatid separation, has been shown to be upregulated with increasing Gleason score and with hormone insensitivity in prostate carcinoma[20]. LNCaP xenografts grown in mice was chosen to visualize the spatial variation of TOP2A mRNA using our technique. With a rapid turn-around time of less than 2 hours, starting from sample acquisition to RT-LAMP reaction, our low-cost technique can perform spatially mapped nucleic acid amplification testing (NAAT) in a typical analytical laboratory.

TOP2A mRNA RT-LAMP in a thermocycler: The first step is to develop and characterize a sensitive and specific RT-LAMP reaction for TOP2A mRNA. We designed a novel RT-LAMP reaction for amplifying TOP2A mRNA using 6 sequence specific primers (primer sequences provided in Table 2).

Figure 9A:
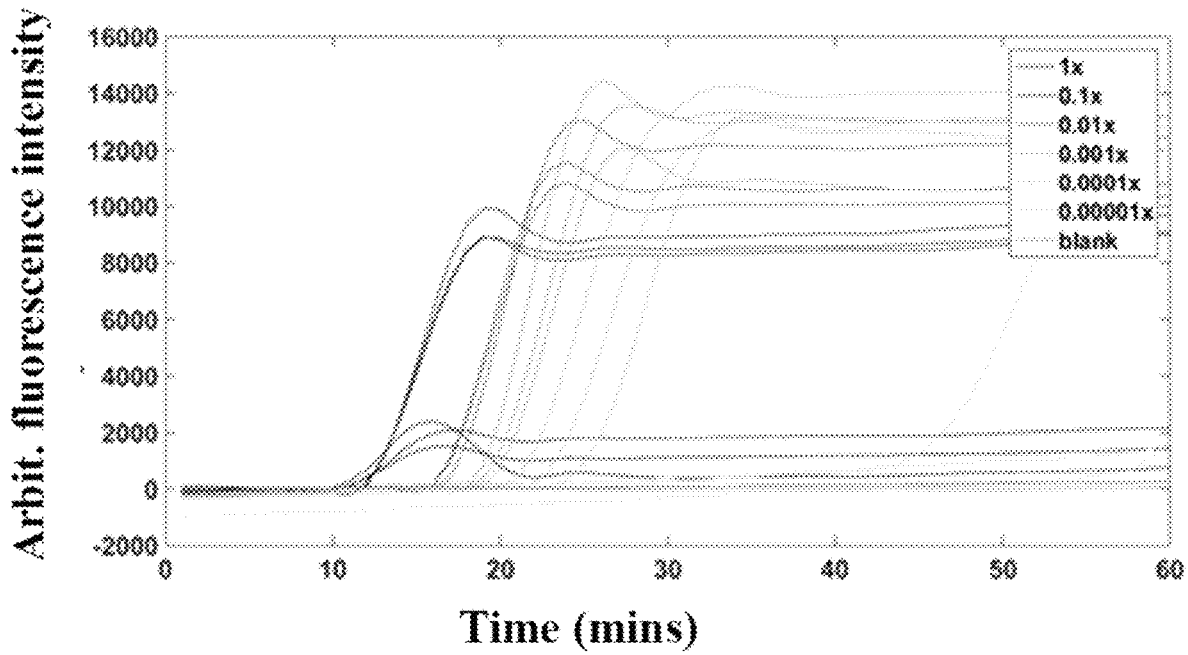
FIGS. 9A-9B. Raw thermocycler fluorescence data (FIG. 9A) and standard curve (FIG. 9B) of RT-LAMP reaction for TOP2A with purified total RNA extracted from tissue. 1× has 98 ng/ul concentration of purified total RNA per reaction. A good linear fit was observed in the standard curve.
Figure 9B:
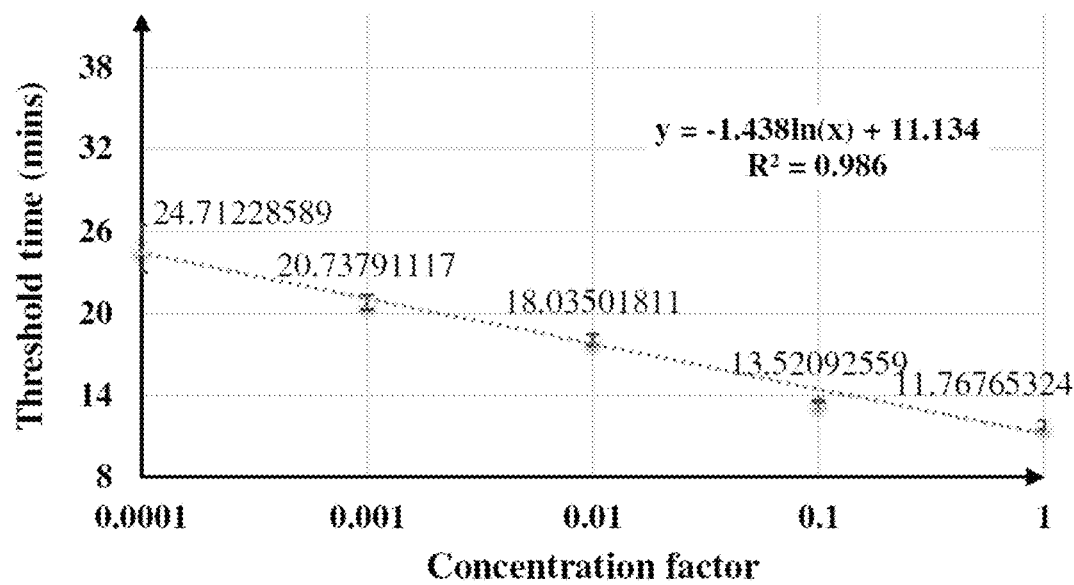
Figure 23A:
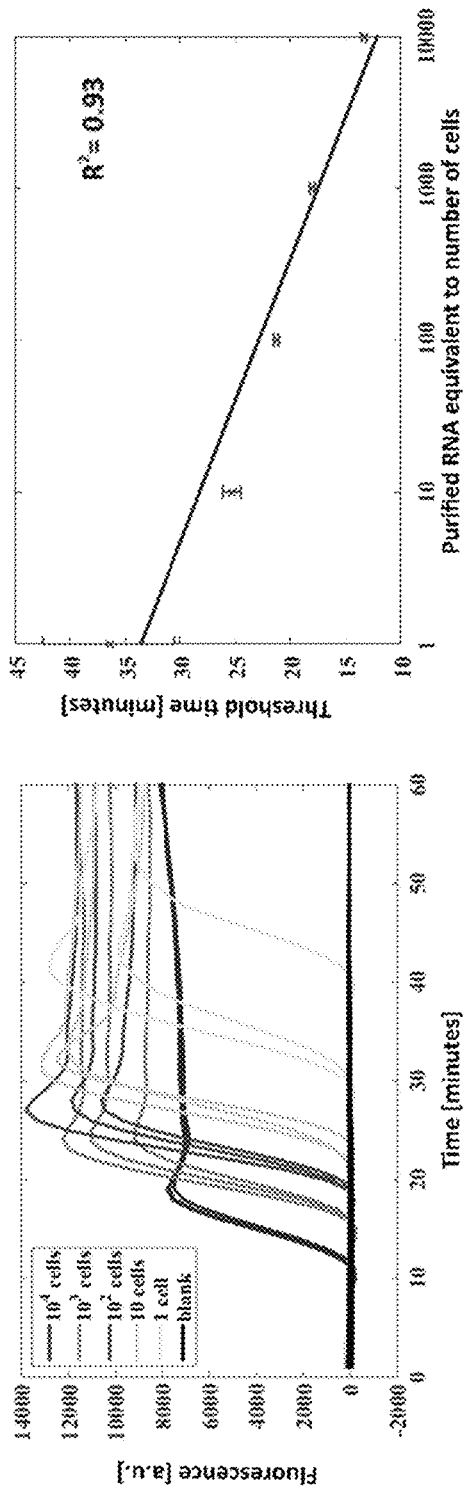
FIGS. 23A-23C. Off-chip RT-LAMP assay characterization.
Figure 23B:
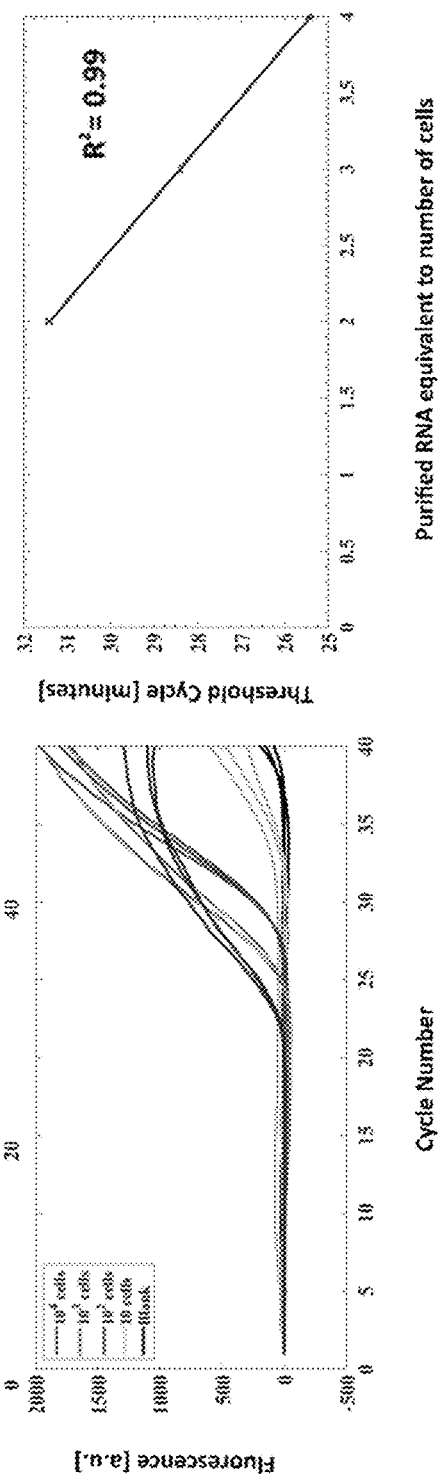

To characterize our TOP2A reaction, RT-LAMP experiments using purified total RNA from xenograft tissue sections and cultured LNCaP cells were performed in a commercial thermocycler and compared with RT-PCR reactions performed using previously published primers with same RNA concentrations[21]. FIG. 23A and FIGS. 9A-9B show the amplification curves and the standard curve for RT-LAMP reactions from purified RNA from LNCaP cells and tissue xenograft, respectively. A good linear fit for the standard curves was obtained for both the reactions ($R^2$=0.93 and 0.98 for total RNA from cells and tissue respectively). FIG. 23B shows the similar amplification curves and standard curve for TOP2A qRT-PCR reaction. The total amounts of RNA per reaction for each dilution was identical in the RT-LAMP and RT-PCR reactions for comparison. TOP2A RT-LAMP was found to be at least one order of magnitude more sensitive than the corresponding RT-PCR reaction with detection down to a single cell equivalent of total RNA (in 25 μL tube-based reactions).

Figure 23C:
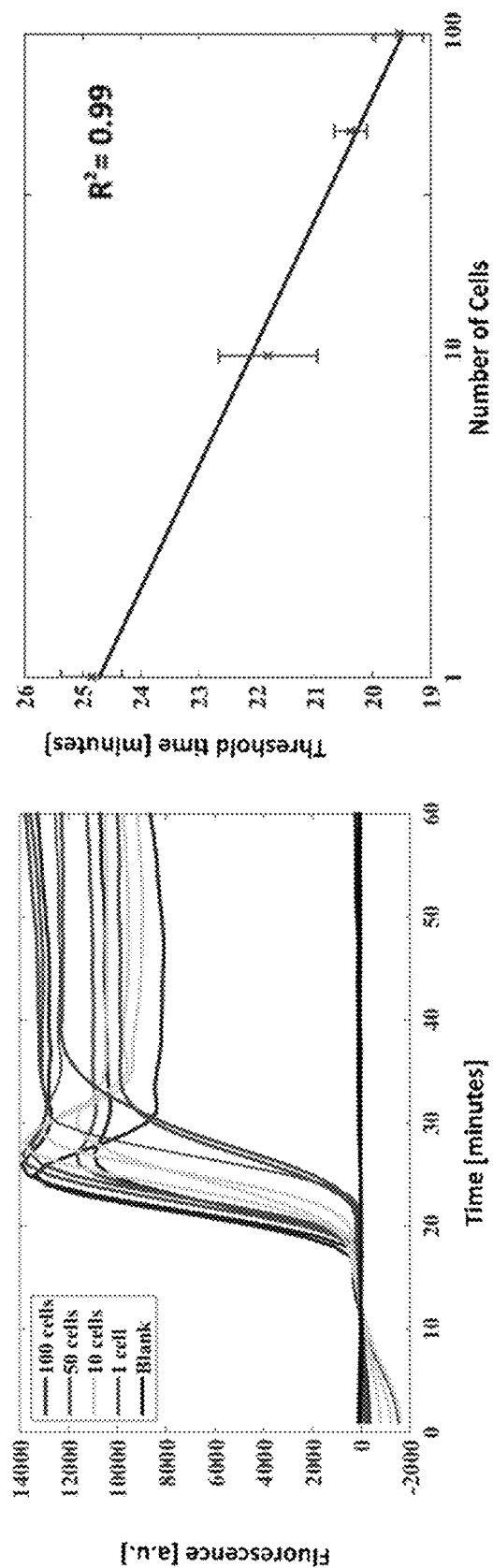

Next, to demonstrate the robustness of our RT-LAMP reaction against inhibitors, using hemocyotemeter counting and serial dilutions we spiked 1 to 100 LNCaP cells directly in a 25 μL reaction tube and performed RT-LAMP in a thermocycler. FIG. 23C shows the amplification fluorescence curves and standard curve for this experiment. Reaction with a single cell could be reliably amplified even in the presence of cell lysate. As seen from FIG. 23A and FIG. 23C, the amplification reaction works better for 100 cells spiked directly into the reaction as compared to purified RNA from 100 cells. We believe that this is due to the loss of some RNA during the RNA purification process. We expect the on-chip sensitivity to go down to a single molecule as the on-chip reaction volumes will be 5 orders of magnitude lower in microchip wells (Vol~175 pL) making the analyte concentrations equivalently higher when compared to tube based thermocycler reactions (Vol~25 μL). As shown in the on-chip experiments on Prostate cancer xenograft tissue, the tissue debris/chassis remains attached to the bottom of the wells and does not become an effective part of the reaction in the solution above. This causes the effect of tissue contaminants on the reaction in wells to be minimized.

Tissue pixelation and bulk picoliter reagent loading: To perform the RT-LAMP reaction on a microchip from tissue samples, we developed two unique preparatory steps: (A) Tissue pixelation—A continuous tissue cryosection disc (7 um thick) was partitioned into thousands of small tissue "pixels" and placed into the corresponding microwells. This was done by pushing a deformable substrate, such as a flexible cured polydimethylsiloxane (PDMS) block into the wells with overlaying tissue using centrifugation in a standard centrifuge (1 min@1500 g force). When the flexible PDMS pushes its way into the wells under centrifugal forces, it shears and partitions the tissue at the sharp well edges. The tissue sticks to the pre-silanized (APTES) well surface and the PDMS layer restores back to its original shape in the absence of force as shown in the FIGS. 22D-22F. Characterization of this process using scanning electron microscopy (SEM) and fluorescence imaging for Nuclei after DAPI staining is shown in FIGS. 24A-24F. The well edges can be clearly visualized as dark lines in the DAPI stained fluorescent images. These data show that the tissue is completely inside the wells after the pixelation step and the tissue partitioning into pixels is complete, allowing for independent RT-LAMP reaction from tissue in each picowell. The 2-D tissue distribution is maintained throughout the process. FIGS. 28A-28E show additional SEM images of tissue pixelation for a rat heart tissue section.

Figure 24A:
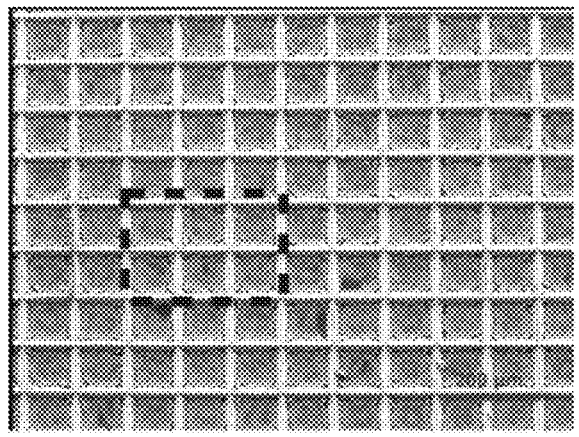
FIGS. 24A-24H. Tissue pixelation and Bulk picoliter reagent loading characterization.
Figure 24B:
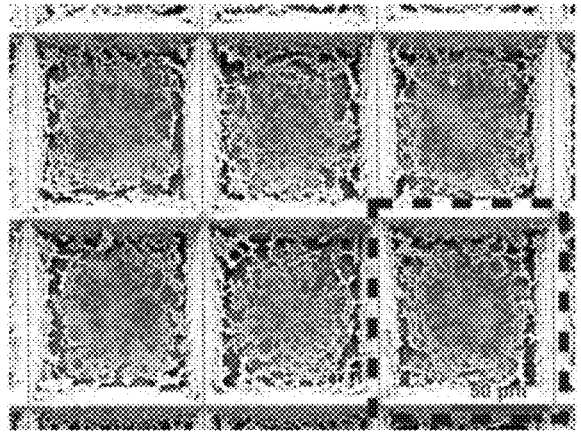
Figure 24C:
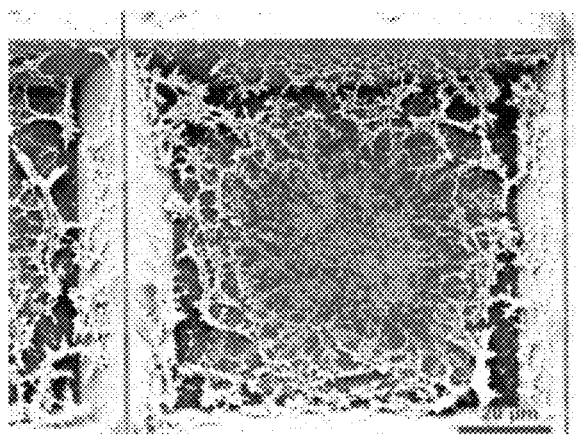
Figure 24D:
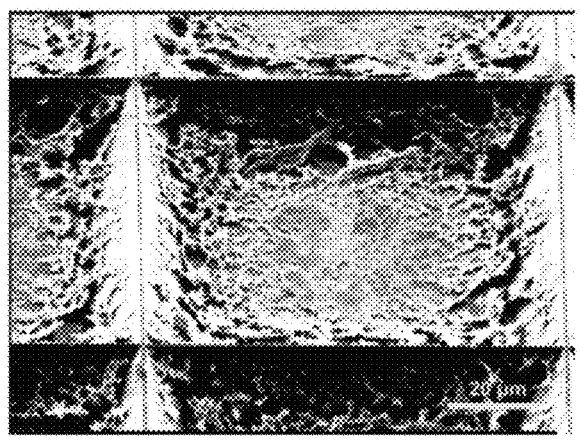
Figure 24E:
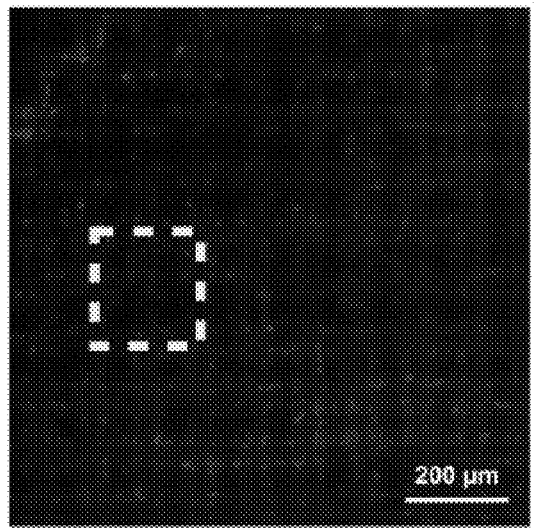
Figure 24F:
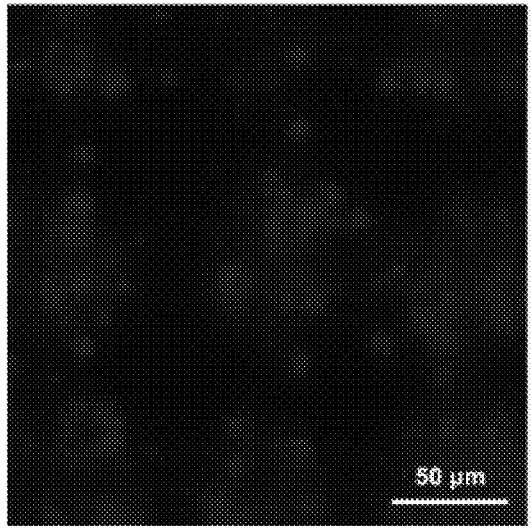
Figure 24G:
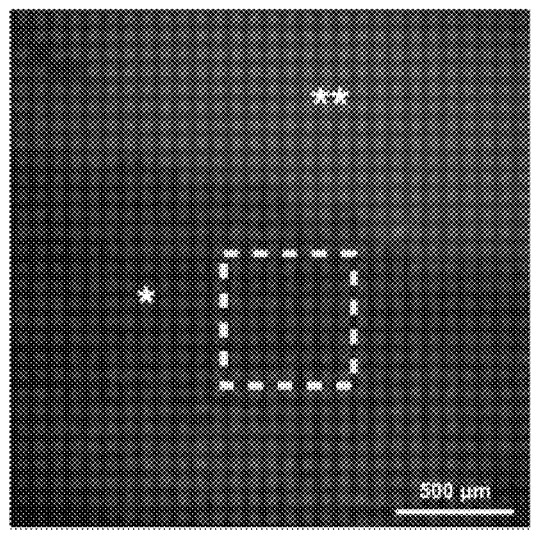
Figure 24H:
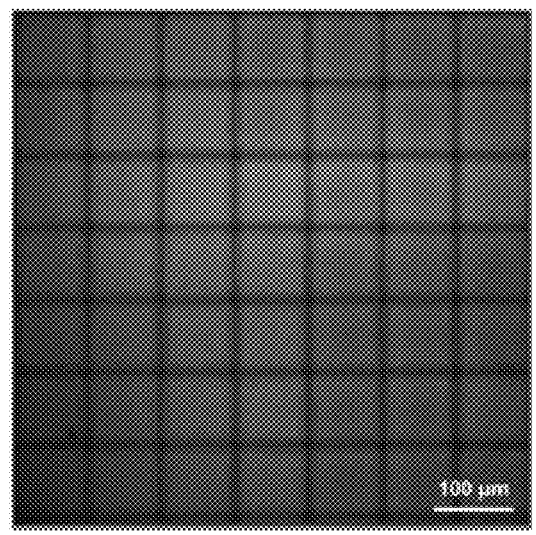

(B) Bulk picoliter reagent loading—To fill the tissue loaded wells with ~175 pL of reagents per well, we developed a capillary action-based instrument-free loading technique. 5 μL of reagents were pipetted on the chip and then the chip was immediately immersed in mineral oil. Mineral oil has a lower density than water based reaction-mixture and hence it stays on top of the reagent-filled wells. With mineral oil acting as an envelope, excess reagents were sheared away using air pressure while capillary forces retained fluid only inside the wells. The process was characterized using fluorescent rhodamine dye. FIGS. 24G-24H show well edges seen as dark lines indicating they are above the fluid level and that there is no cross-talk between adjacent wells. 98.2% of the wells were found to be fully filled (fluorescence intensity greater than 22 a.u). and partially filled wells d were found only near the chip borders. FIGS. 7A-7B show the complete chip data for this process. The above two processes ensure independent picoliter RT-LAMP reactions in each well starting from a tissue sample. Mineral oil is one example of an "inert covering fluid" that does not substantively react with any of the relevant materials and is used to facilitate bulk fluid handling and removal.

Figure 4A:
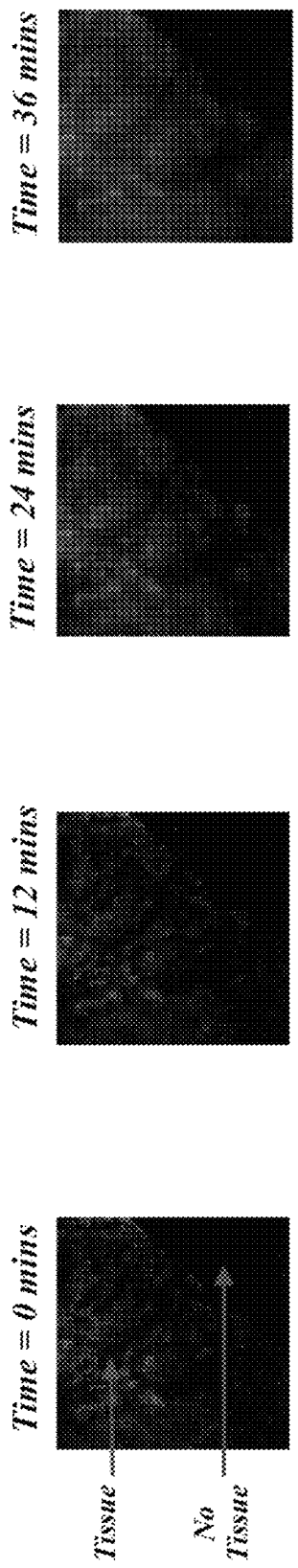
FIGS. 4A-4D. On-chip RT-LAMP.
Figure 4B:
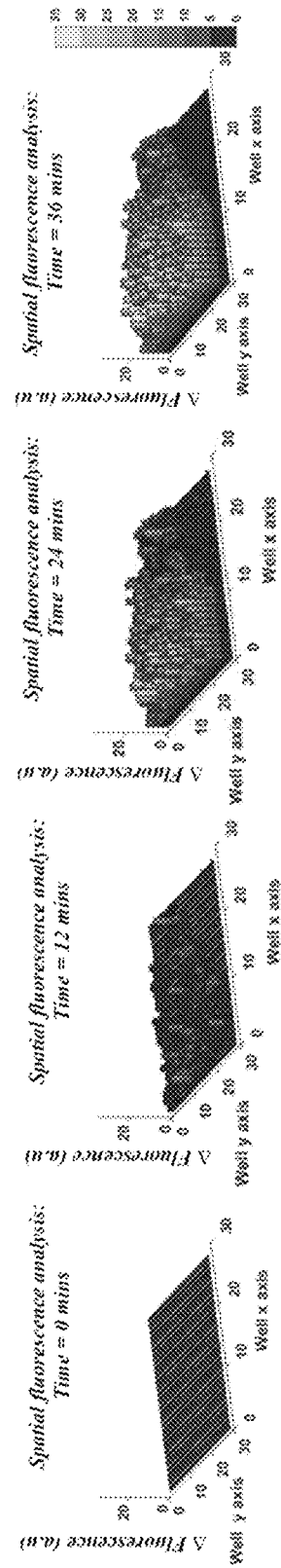
Figure 4C:
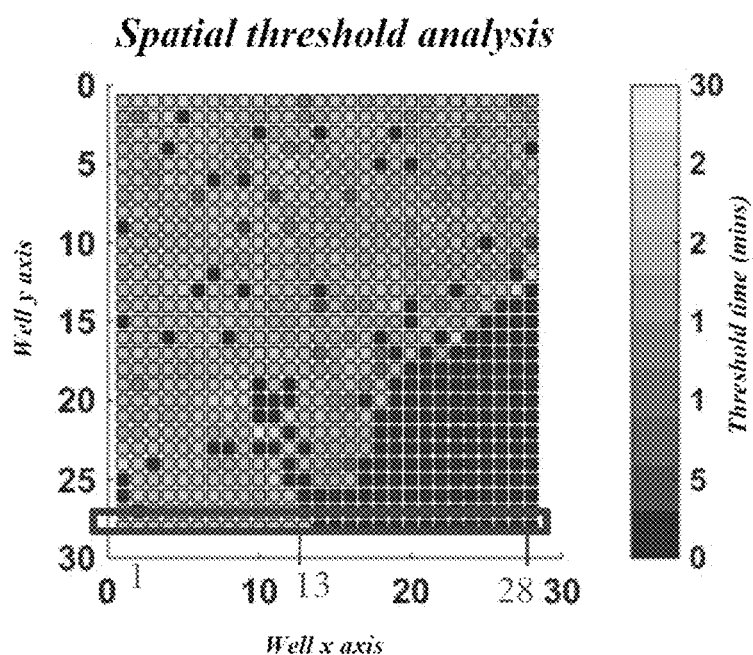
Figure 4D:
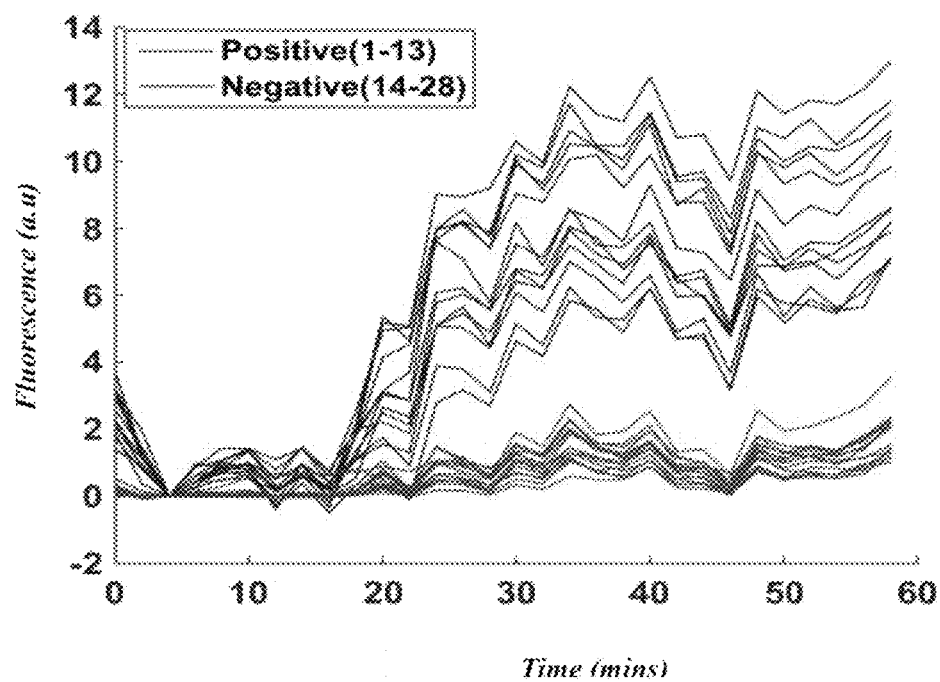
Figure 5A:
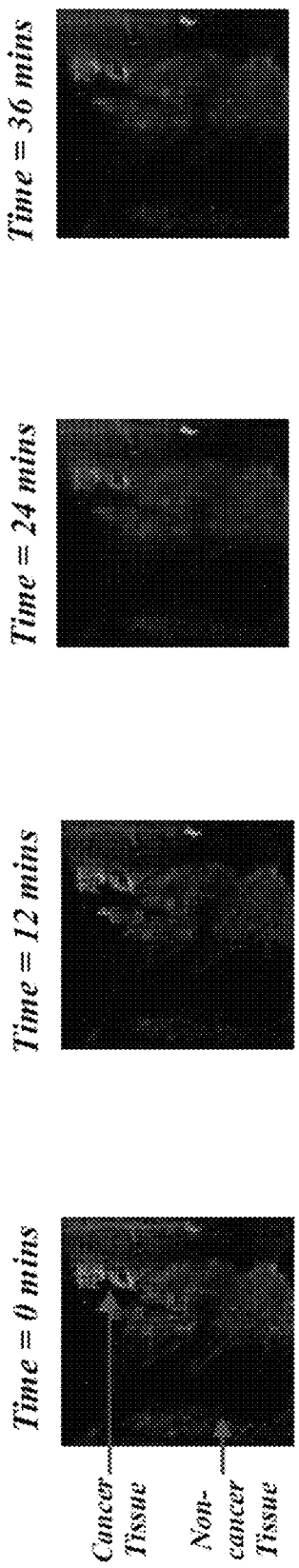
FIGS. 5A-5D. On-chip RT-LAMP: Cancer vs non-cancer control.
Figure 5B:
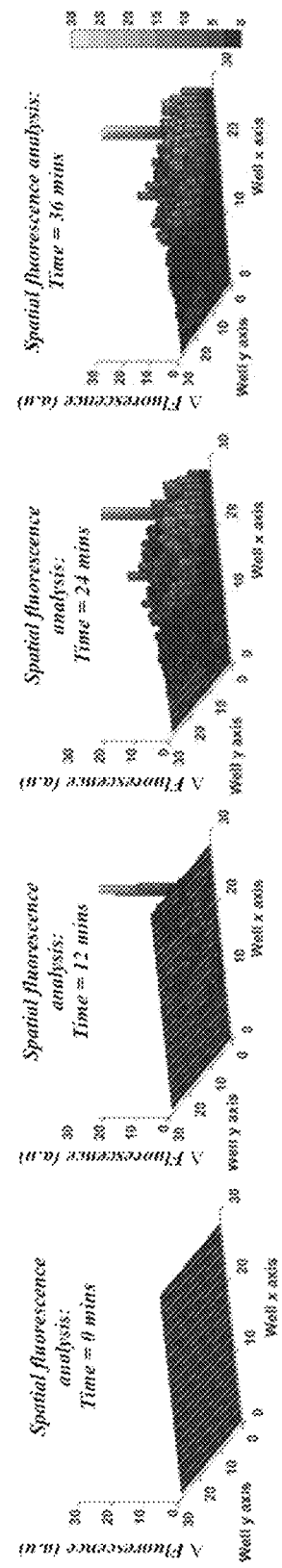
Figures 5C, 5D:
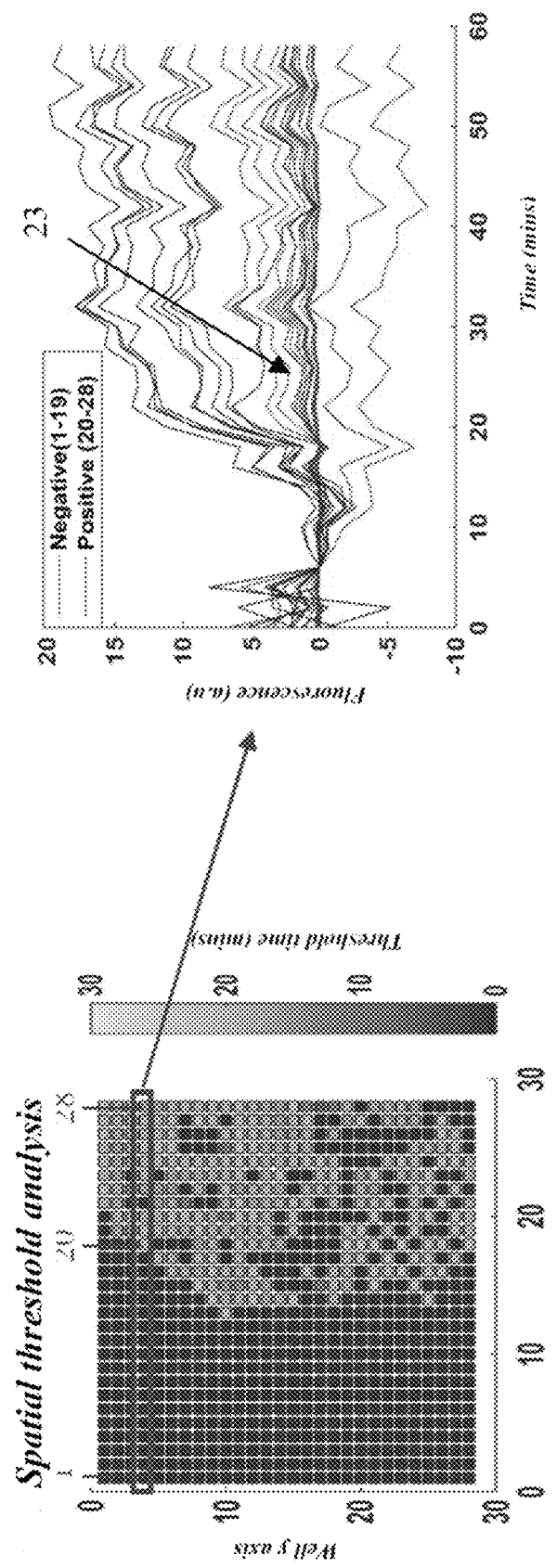
Figure 6A:
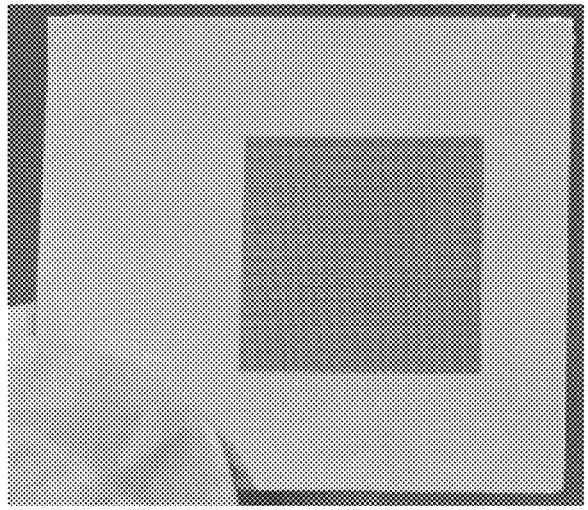
FIGS. 6A-6D. Chip characterization.
Figure 6B:
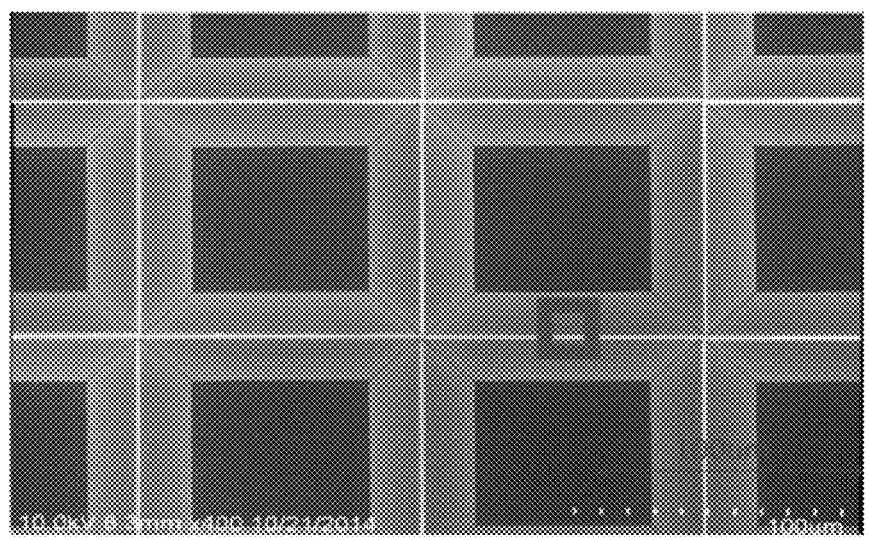
Figure 6C:
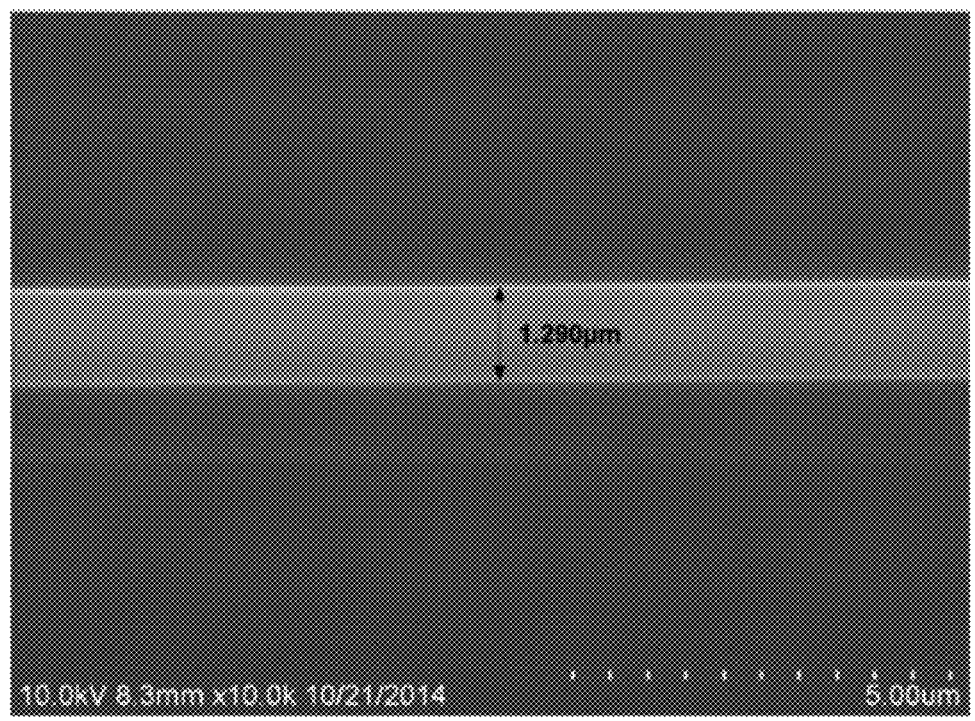
Figure 6D:
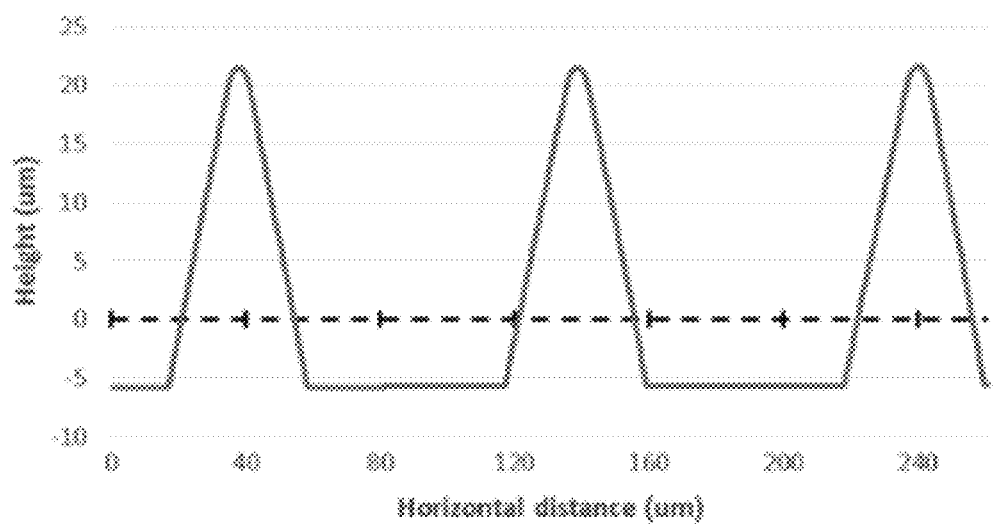
Figure 29A:
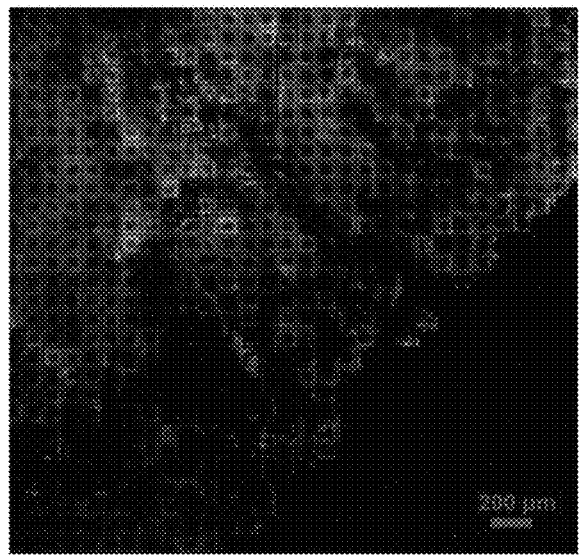
FIGS. 29A-29E. Regional Image Analysis for FIG. 24.
Figure 29B:
Figure 29C:
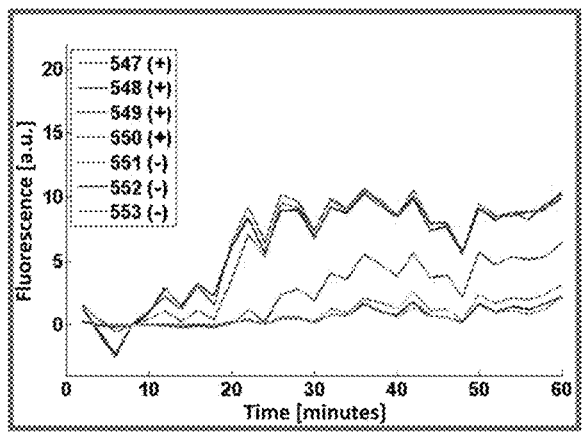
Figure 29D:
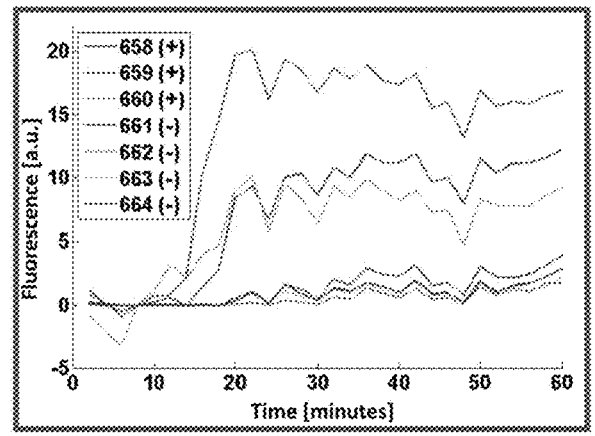
Figure 29E:
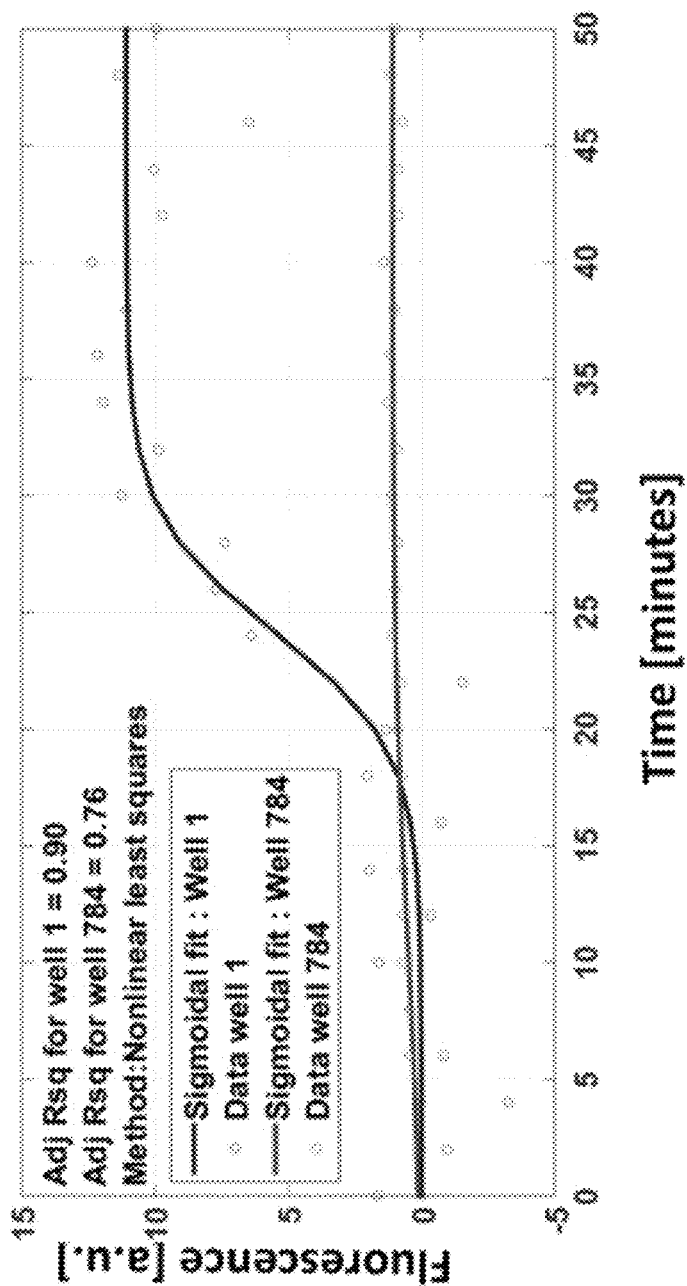

Real-time microchip RT-LAMP: Before performing the real-time microchip RT-LAMP reaction, the pixelated tissue was first fixed using acetone for 10 minutes to prevent RNA degradation at room temperature[22]. Following this, the tissue was treated with proteinase K (7.5 mg/ml for 30 mins), which digests the cell membrane proteins making the cells permeable to polymerase and reverse transcriptase enzymes.[3] This allows RT-LAMP reagents to penetrate the cells and carry out amplification. As opposed to lysing the whole tissue, in which scenario the tissue debris would have been completely mixed with the overlying solution in wells, using proteinase K digestion to expose the target analyte inside the tissue prevents the tissue contaminants from becoming an effective part of the reaction. The amplification reagents were loaded using the previously described technique and the amplification was performed on a hot plate at 65 C. Imaging was done every 2 minutes using a 5× objective and TRITC filter in an Olympus BX51 fluorescence microscope. The on-chip amplification reaction was completed in 35 minutes and the progressive product accumulation in each well was visualized as proportional increase in the fluorescence in the corresponding well. These real-time fluorescence curves were used to calculate the threshold times for each well. FIGS. 4A-4C show the fluorescence images at different time points, the differential spatial fluorescence bar graphs and the spatial threshold time analysis showing the variation in threshold times, respectively. FIG. 12A shows the raw fluorescence data over time for a row of wells. A sigmoidal curve fitting was performed on the raw fluorescence curves from all the imaged wells and threshold time was calculated as shown in FIGS. 11 and 29E. Fluorescence curves from all the imaged wells are shown in FIG. 12B after the fitting analysis. Analyzing regions close to the tissue boundary showed that the tissue boundary was maintained during the reaction suggesting that there was no crosstalk between adjacent microwells and our rapid tissue pixelation and reagent loading technique indeed isolated each picowell. (FIGS. 4A-4C and FIG. 12A). The regions without any tissue showed no non-specific amplification. To demonstrate the scalability of our technology, we also performed similar on-chip reactions from tissue on two different well sizes of 300 um and 500 um, the results for which are shown in FIGS. 18A-18D, 19B-19D, 20A-20D and 21B-21D. To further ensure that the signal observed was not due to spurious amplification, two negative controls, one with no primers in the reaction mix and other with RNase A (100 µg/ml for 1 hr) treated tissue for RNA degradation were performed and no amplification was observed for either. (FIGS. 16A-16B and 17A-17B).

As a final specificity test of our on-chip assay, we challenged our platform by loading cancer and non-cancer (mouse skeletal muscle tissue) tissue on the same chip and performing the reaction simultaneously on them. FIGS. 25A-25E show the fluorescence images at different time points, the differential spatial fluorescence bar graphs and the spatial threshold time analysis showing the variation in threshold times, respectively. FIG. 25D shows the raw fluorescence data over time for a row of wells and fluorescence curves from all the imaged wells are shown in FIG. 25E after the fitting analysis. It is observed that only the cancerous tissue amplified validating the specificity of our on-chip assay. We imaged at most 784 wells (100 um well size) for our real-time on-chip measurements.

Figure 26A:
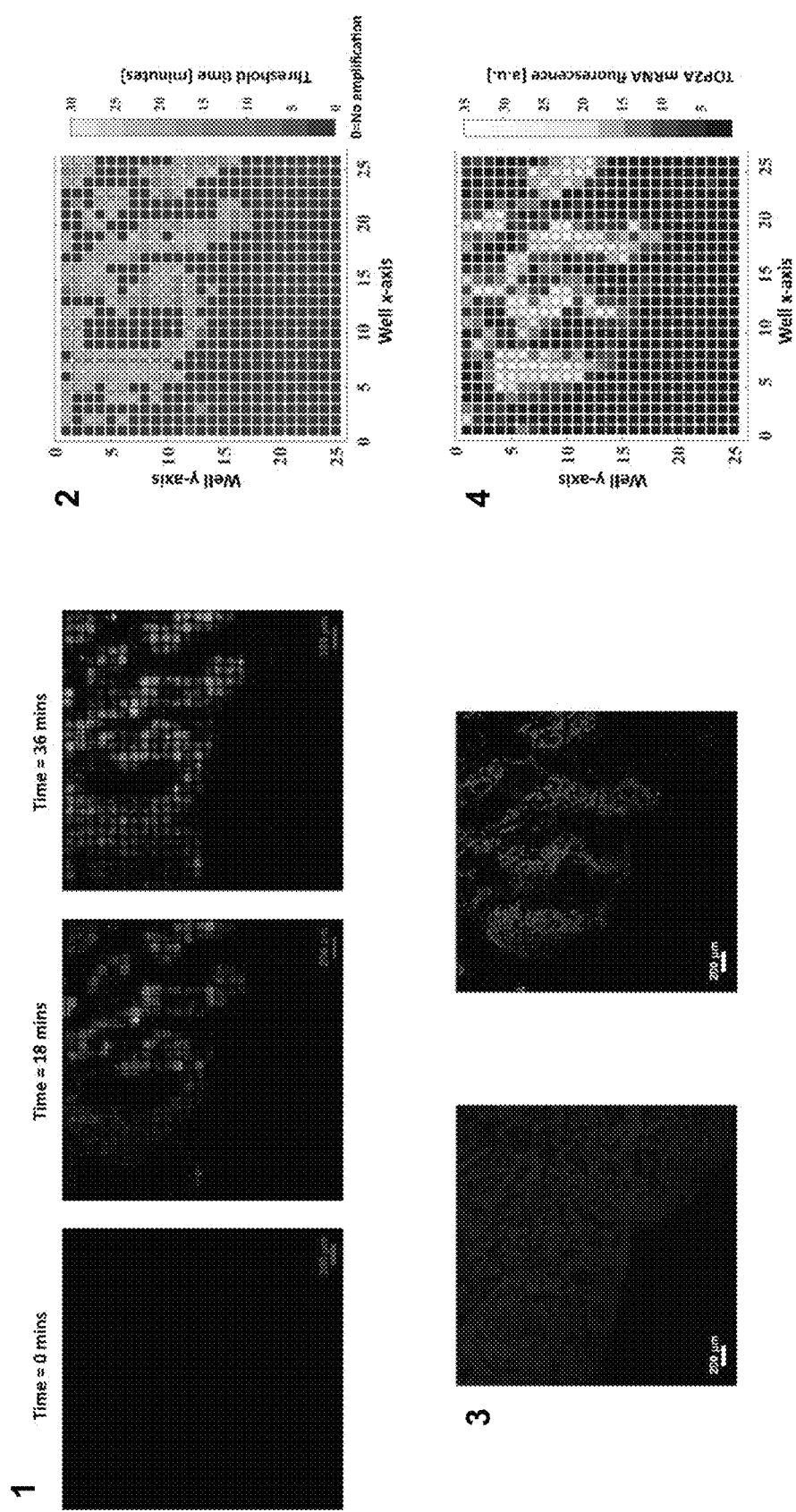
FIGS. 26A-26B. On-chip RT-LAMP with mRNA FISH on serial sections.
Figure 26B:
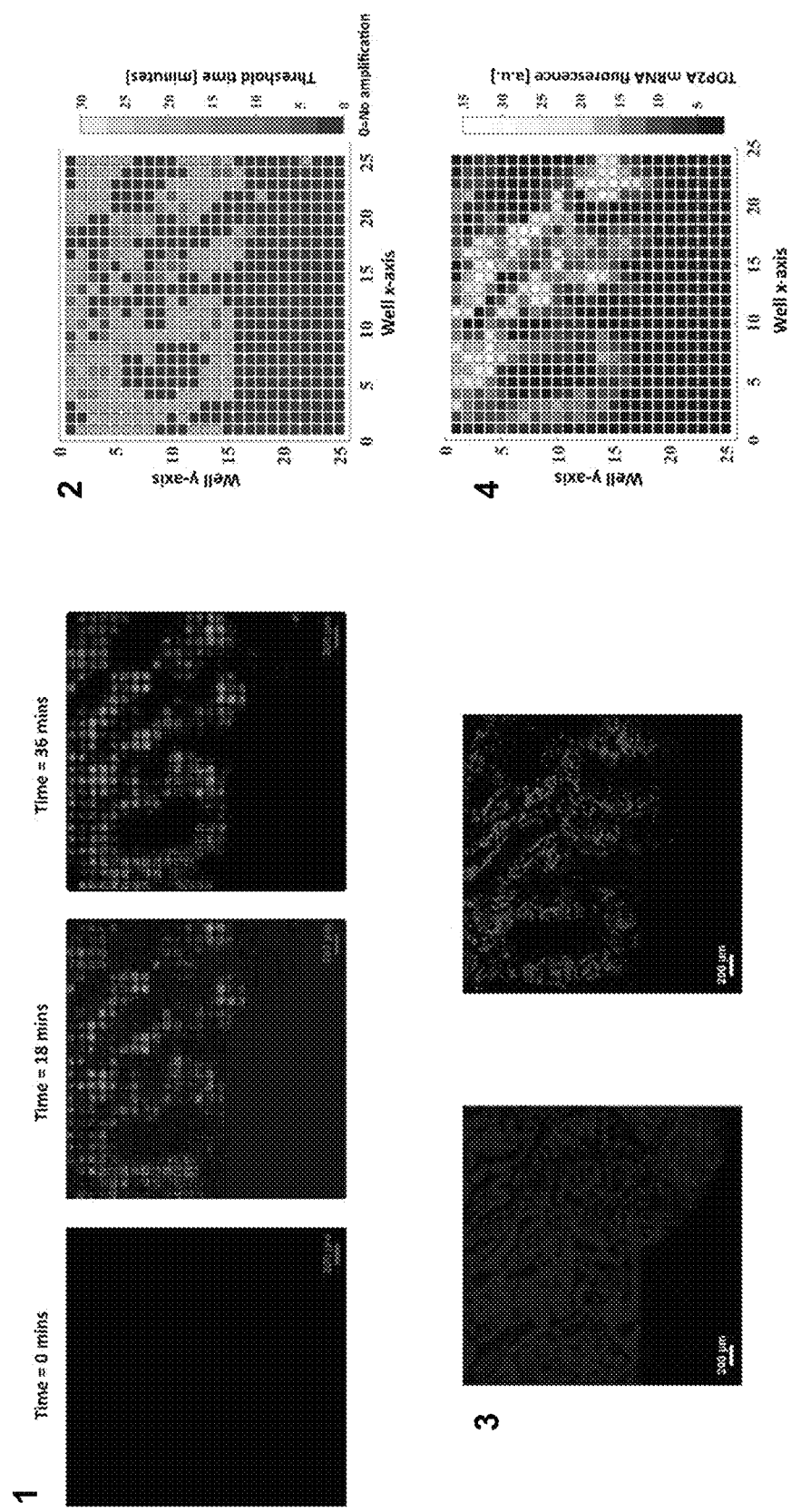
Figure 28C:
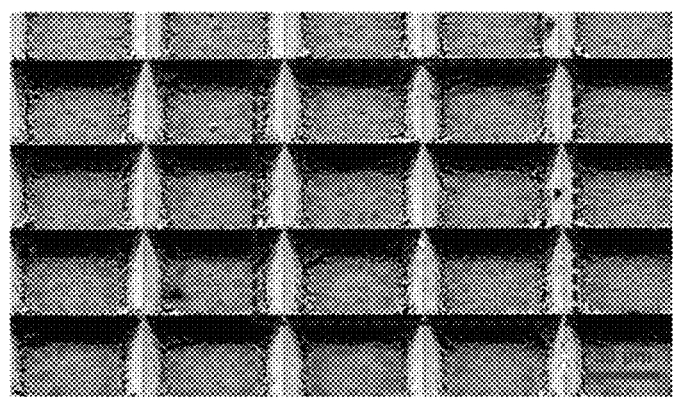
Figure 28D:
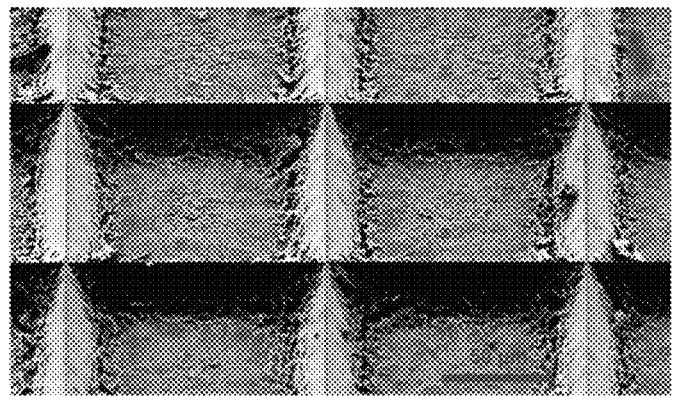
Figure 28E:
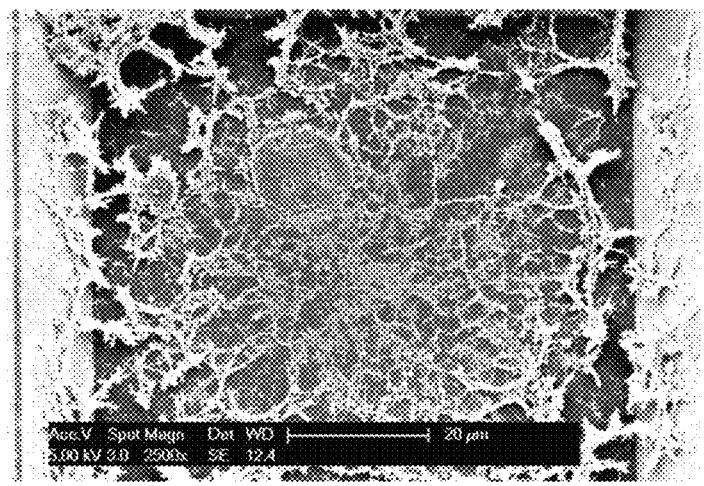

Comparison with mRNA fluorescence in situ hybridization (FISH): As further validation of our technique, we performed mRNA FISH and microchip spatial amplification on serial sections of the tissue. FISH probes for human TOP2A mRNA were confirmed to specifically stain human prostate cancer cells (PC3, LNCaP) and to not stain non-expressing mouse cell lines (3T3, RAW 264.7) (FIGS. 30A-30D). The probe sequences are provided in Table 3. FIGS. 26A-26B show two sets of experiments for which microchip amplification and mRNA FISH were performed on consecutive tissue sections. For microchip amplification, FIG. 26A panel 1 and FIG. 26B panel 1 show baseline subtracted fluorescence images at three different time points of the real-time amplification, demonstrating an increase in fluorescence over time. FIG. 26A panel 2 and FIG. 26B panel 2 show the spatial threshold time analysis, demonstrating the variation in threshold times across the tissue sections for the two sets. FIG. 26A panel 3 and FIG. 26B panel 3 show confocal fluorescence micrographs of nuclei (blue) and TOP2A mRNA FISH (red), showing spatial heterogeneity in TOP2A mRNA expression. These micrographs were then pixelated at the same spatial resolution as the spatial threshold time maps and displayed in FIG. 26A panel 4 and FIG. 26B panel 4. A substantial correlation in the general spatial pattern is apparent between the results through the two TOP2A mRNA measurement methods. However, because higher mRNA expression levels yield faster amplification, mRNA FISH fluorescence intensity is negatively correlated with threshold time. Spearman correlation coefficient values between the pixelated maps of mRNA FISH and spatial thresholds were −0.56 (p=8.7881e−55) and −0.57 (p=3.9886e−54) for the data sets in FIGS. 26A and 26B, respectively. These correlations were substantially stronger than those comparing pixelated maps of nuclear stains and spatial thresholds, with correlation values of −0.38 (p=9.0580e−24) and −0.37 (p=9.9159e−22), respectively.

The methods and devices described herein can be tuned to perform quantitative spatially-mapped nucleic acid microchip analysis of any tissue sample type on a simple hot plate and fluorescence microscope. It can also be integrated into a completely portable setup using a smartphone and in-built heater making the technique accessible even to labs without a microscope[12]. These methods and devices allow analysis of small-to-large tissue regions without any cross-talk between individual tissue pixels. The tissue pixelation and bulk picoliter reagent loading techniques perform sample partitioning of solid-tissue samples and liquid-reagent samples respectively, in easy-to-perform steps that take only 1-2 minutes. This is remarkable considering that commercial solutions for spotting arrays of nanodroplets cannot spot picoliters of volume in close spacing, have large dead volumes (non-usable reagent pool) and suffer from long sample loading times (loading 5000 wells would take several hours)[28,29]. Our technique can be scaled to fill larger arrays with millions of wells using the same principle in a matter of minutes. Both the size of our chip and wells can be tuned to meet sample size and spatial resolution requirements and we demonstrate this by showing on-chip amplification for 300 and 500 µm wells apart from the 100 µm wells. We expect the same should be possible for lower well sizes that go down to a single cell per well, in which case we can make the wells deeper to get similar reaction volumes as for the 100 um wells to keep the same reaction kinetics. The described methods and devices, which can be easily translated into routine analysis in resource-starved settings to highly sophisticated measurements, has many important clinical and biological applications such as understanding tumor evolution and heterogeneity, predicting patient outcomes, post-operative characterization of surgical margins and detecting point mutations across the tissue[30].

Cells and Xenografts. LNCaP prostate cancer cells were obtained from and verified by the American Type Culture Collection (ATCC). The cells were cultured per the recommended standard in a 37° C. humidified incubator with 5% CO2 atmosphere.

LNCaP subcutaneous Xenografts were grown in immunocompromised nude mice (Jackson Laboratory). LNCAP cells were first incubated and grown to confluence. Then, these confluent cells were suspended in 10% matrigel at a concentration of $2 \times 10^7$ cells/60 µL and 60 µL of this matrigel-cell solution was injected subcutaneously into both flanks of the animal. The mice were then monitored daily for the presence of tumors. As soon as tumors were visible, volume measurements were taken using digital calipers twice a week, and tumor volumes were calculated using the formula Volume=(Length*Width^2)/2. Once tumors reached 50,000 mm^3 in volume, the mice were sacrificed by overdosing with isofluorane anesthesia, after which the tumors were immediately excised and divided to be placed in optimal cutting temperature compound (OCT), or 4% PFA.

Primer Sequences: All primer sequences for the RT-LAMP and RT-PCR reactions were synthesized by Integrated DNA Technology (IDT) and are listed in Table 2. Primerexplorerv4 was used for designing the RT-LAMP primers for TOP2A mRNA. The cDNA sequence for TOP2A was obtained from NCBI database using NCBI Reference Sequence: NM_001067.3.

Off-chip reactions. RT-LAMP assay was designed to target the Topoisomerase II alpha (TOP2A) mRNA. The RT-LAMP assay comprised of the following components: 1× final concentration of the isothermal amplification buffer (New England Biolabs), 1.4 mmol/L each of deoxy-ribonucleoside triphosphates (dNTPs), 10 mmol/L of MgSO4 (New England Biolabs), and 0.4 mol/L of Betaine (Sigma-Aldrich). These components were prepared in bulk and stored at −20° C. between experiments. In addition to the buffer components, 1 µL of primer mix consisting of 0.2 µM of F3 and B3, 1.6 µM FIP and BIP, and 0.8 µM of LoopF and LoopB, 0.64 U/μL Bst 2.0 WarmStart DNA Polymerase (New England Biolabs), 0.08 U/μL AMV reverse transcriptase (New England Biolabs), and 1× EvaGreen (Biotium), a double-stranded DNA (dsDNA) intercalating dye, was included in the reaction. 10 μL template of the appropriate concentration and 1.92 μL of DEPC-treated water (Invitrogen) was added to make the final reaction volume 25 μL.

The RT-PCR reaction was carried out using the RNA UltraSense™ One-Step Quantitative RT-PCR System (Thermofisher) according the manufacturer's instructions. A 50 μL reaction mix contained 2.5 μl of RNA UltraSense™ Enzyme Mix, 10 μl of RNA UltraSense™ 5× Reaction Mix™, 1 μl of 10 μM Forward primer, 1 μl 10 10 μM backward primer, 1 μl of SYBR Green dye (Thermofisher), and 34.5 μl of template of appropriate starting concentration.

Template for the RT-LAMP reactions included either RNA extracted from LNCaP cells or LNCaP prostate xenograft tissues, or whole LNCaP cells spiked in the reaction mix. All RNA extractions were performed using the RNeasy Mini Kit (Qiagen) according to the manufacturer's instructions. All RT-LAMP and RT-PCR reactions consisted of non-template negative controls, the amplification of which indicated a contaminated test.

All the off-chip LAMP tests were carried out in 0.2 mL PCR reaction tubes in an Eppendorf Mastercycler® realplex Real-Time PCR System. The tubes were incubated at 60° C. for 60 minutes in the thermocycler, and fluorescent data was recorded every 1 minute. The off-chip PCR tests were conducted on the same thermocycler but with the following recipe: RT incubation at 50° C. for 50 minutes, 2 minutes DNA denaturation at 95° C., and 50 cycles of thermocycling from 95° C. (15 seconds) to 60° C. (30 seconds). Fluorescence data was recorded after each cycles of the reaction.

Chip Fabrication and Chip Silanization. Undoped silicon wafers (University Wafers) were piranha cleaned for 10 minutes and a 160 nm of silicon oxide was thermally grown in a furnace at 1150° C. for 90 minutes. A 2 μm layer of positive photoresist AZ1518 (AZ Electronic Materials) was spin-coated on the unpolished side of the wafer and was soft-bake on a hot plate at 110° C. for 8 minutes. The same process was repeated on the polished size of the wafer. The photoresist on the shiny side was patterned using an EVG 620 aligner with a high resolution transparency mask (Fine-Line Imaging). The wafer was then developed in AZ400K (AZ Electronics) to remove the exposed regions for 1 minute. The unprotected silicon oxide was etched in 10:1 buffered oxide etchant (VWR) to reveal the underlying bare silicon. This was followed by stripping the wafer of photoresist in a Remover PG (MicroChem) at 70° C. for 30 minutes. The wafer was then anisotrpically etched in a TMAH bath (1:1 TMAH:DI) for 100 mins at 80 C to etch inverted square pyramidal wells with sharp well edges. To passivate the chip, a 125 nm of silicon oxide was thermally grown in a furnace at 1150° C. for 90 minutes.

To render a positive charge on well surfaces for tissue adhesion, silicon chips were silanized with functional groups using (3-Aminopropyl)triethoxysilane (APTES). The chips were dipped in a glass jar containing 0.2% APTES for 60 seconds. The chips were then dipped 5 times in a separate vessel containing distilled water. This step was repeated three more times with the water being replaced between each step. The silanized chips were stored in a desiccator, and were used within 15 days of silanization.

Tissue Pixelation, Fixation, and Proteinase K digestion: The frozen tissue was cryosectioned at a thickness of 7 μm onto the center of the microchip and stored at −20° C. Once ready for use, the tissue was taken out of the −20° C. freezer and dried immediately to minimize RNase activity within the tissue. A short heating step at 105° C. for 5 seconds was incorporated to ensure that the tissue is stabilized on the chip. A clean block of PDMS was then placed on top of the tissue and the whole PDMS-chip conjugate was centrifuged at 3000 rpm for 1 minute to press the tissue into the wells in a process known as tissue pixelation. The block of PDMS was discarded, and a second heating step at 105° C. for 7 seconds was carried out to ensure that the tissue is firmly adhered and stable on the chip.

A standard acetone fixation protocol was followed to fix the tissue onto the chip. The chip was placed on a small glass petri dish filled with acetone and incubated at −20° C. for 8-9 minutes. After the incubation step, the chip underwent a series of wash steps. First, half of the acetone was discarded from the petri dish and an equal amount of cold PBS (Fisher Scientific) was poured into the petri dish to replace the acetone. The petri dish was shaken for 30 seconds and the step was repeated. The chip was then placed on a petri dish containing cold PBS and shaken for 2 minutes. This was followed by a rinse with DEPC-treated water at room temperature for one minute. The chip was then air-dried for 1 minute.

The chip was placed on a petri dish with Proteinase K at a concentration of 7.5 μg/mL and incubated at 45° C. for 30 minutes. Once the digestion was complete, the Proteinase K was denatured by heating the chip at 95° C. for 90 seconds. The chip was washed with PBS for 10 seconds and DEPC-treated water for 30 seconds to remove the residual Proteinase K.

Bulk Loading and On-chip RT-LAMP reactions: A 25 μL reaction mix was prepared for a single on-chip test, and 10 μL of the reaction mix was pipetted onto the tissue/wells, and immediately coated with a layer of mineral oil. The chip was then placed in a petri dish covered with mineral oil and degassed for 5 minutes to remove any air bubbles. After degassing, the chip was dipped in mineral oil, and an air pressure is applied at an angle to shear off and remove excess reagents from top of the wells. The chip was then placed on a copper bowl and placed on a hotplate under a fluorescent microscope to perform the on-chip RT-LAMP reactions.

The on-chip reactions were carried on a commercial hotplate at 65° C. for 60 minutes and imaged every 2 minutes under an Olympus BX51 fluorescence microscope with 3.6 s exposure settings and 16× gain. TRITC filter was used for imaging the evagreen fluorescent dye.

Amplification Data Analysis: The off-chip amplification and standard curves were plotted using a MATLAB script. The threshold time for each curve was taken as the time required for each curve to reach 20% of the maximum intensity. For on-chip reactions, the raw fluorescent intensity on-chip was extracted from each well and was plotted against time to generate the raw fluorescence curves. Each raw amplification curve was fitted to a sigmoidal curve using a four-point parameter modeling (FIGS. 26A-26B). The following equation was used for the analysis:

$$f = y_0 + \frac{a}{1 + e^{-\left(\frac{x-x_0}{b}\right)}}$$

Where f=fluorescence intensity, $y_0$=background fluorescence at time=0 minutes, a=difference between the initial and final fluorescent intensity, x=time point of analysis, $x_0$=inflection point of the curve, b=slope of the curve. The threshold time was obtained at the point where the fluorescent intensity=$y_0$+0.2*a. The positive and negative wells were differentiated on the basis of the $R^2$ value of the sigmoidal fit and the parameters a and $x_0$. The threshold time was taken as the point of inflection. Negative wells had a combination of low R2 value, low a value, or a very high threshold time ($x_0$>50 mins).

TOP2A mRNA FISH Probe Design: FISH probes targeting human TOP2A mRNA (NM_001067.3, 3490 bp to 5753 bp) were designed using Stellaris® Probe Designer (version 4.2, LGC Biosearch Technologies, US). Probe sequences with 85% or greater homology with mouse TOP2A mRNA complementary sequences were excluded. The resulting set of 36 mRNA FISH probes with 3' Quasar 670 dye label was synthesized by LGC Biosearch Technologies. Probe sequences are listed in Table 3.

Validation of TOP2A mRNA FISH on Cell Lines: Probe specificity was validated on TOP2A-positive human cell lines (LNCaP and PC-3, generous gifts from Dr. Stephen J. Murphy, Mayo Clinic) and mouse cell lines as negative controls (3T3 and RAW 264.7, purchased from ATCC) following previously published procedures[6] and protocols provided by the probe supplier. Briefly, 1×10⁵ cells were seeded on 18 mm round #1 coverglass in each well of a 12-well cell culture plate. After adhering, cells were washed with phosphate buffered saline and fixed with 4% paraformaldehyde for 10 minutes at room temperature. Cells were then permeabilized with 70% (v/v) ethanol for 24 hours at 4° C. Ethanol was aspirated and Wash Buffer A (LGC Biosearch Technologies) was added. After incubated for 5 minutes at room temperature the coverglass was transferred face-down onto Parafilm with 100 μL of Hybridization Buffer (LGC Biosearch Technologies) containing probes. After incubation for 16 hours in the dark at 37° C. in a sealed humidified chamber, the coverglass was washed with Wash Buffer A in the dark at 37° C. for 30 minutes. Nuclei were counterstained with Hoechst 33342 (Thermo Fisher, US) for 30 minutes. The coverglass was then washed with Wash Buffer B (LGC Biosearch Technologies) for 5 minutes before mounting on slides containing Vectashield Mounting Medium, and sealed using nail polish. FISH probes and nuclei were imaged using a Leica SP8 UV/Visible Laser Confocal Microscope (Leica, Germany) with a 63× oil-immersion objective.

TOP2A mRNA FISH on Prostate Tumor Tissue: Experimental procedures for FISH staining were reported previously[32] and provided by the probe supplier. Tumor tissue sections were stored at −80° C. and equilibrated to room temperature before use. The tissue-mounted slides were immersed in 4% paraformaldehyde fixation buffer for 10 minutes at room temperature and then treated in the same way as cell lines for mRNA FISH, with the exception that a 20× oil objective was used for image collection.

mRNA FISH and microchip amplification correlation analysis: A pixelated mRNA FISH image with the same resolution as the spatial threshold map was generated by taking the mean fluorescence intensity of the neighbouring pixels. For the correlation analysis, the non-amplifying pixels were assigned a value of 100 as their threshold time. The spearman correlation coefficient and the associated p-values between the two images were obtained using the corr function in matlab.

TABLE 2

The RT-PCR and RT-LAMP primers were synthesized by Integrated DNA Technologies (IDT), and are listed below.

| | | SEQ ID NO. |
|---|---|---|
| TOP 2A RT-LAMP primers | F3: GTC GTG TCA GAC CTT GAA | 1 |
| | B3: TAG TTC CTT TTG GGG CAG | 2 |
| | FIP: TCT GGG AAA TGT GTA GCA GGA GGC TGA TGA TGT TAA GGG CA | 3 |
| | BIP: AAC CCA GTT CCT AAA AAG AAT GTG AGT GGA GGT GGA AGA CTG A | 4 |
| | Loop F: GGC TTG AAG ACA GTG GTA CAC | 5 |
| | Loop B: CAG TGA AGA AGA CAG CAG CAA | 6 |
| TOP2A RT-PCR primers | Forward: TGG CTG CCT CTG AGT CTG AA | 7 |
| | Reverse: AGT CTT CTG CAA TCC AGT CCT CTT | 8 |

Bayesian inference-base method: Metrics were identified by the examination of spectra, S, by a trained spectroscopist from regions delineated by a trained pathologist. From the universal set of metrics, M={$m_1, m_2, \ldots m_n$}, an evaluation of pairwise error and incremental increase in classification accuracy for every class, C={$c_1, c_2, \ldots, c_i$}, resulted in a subset of 2 metrics. These were further reduced to a set of 18 by leaving out one metric at a time and evaluating the resulting classification accuracy on validation array data. The classification process reported here consists of evaluating the maximum a posteriori probability for every class $c_i$, $p_i(c_i|M)$, for every metric profile from every spectrum from the image M(x,y) to formulate a decision rule $$p(c_j|M) > p(c_i|M), i=1,2,\ldots,n_c, i \neq j \qquad (1)$$

Classification evaluation: As the threshold acceptance value determines an operating point for the algorithm, a systematic variation of the acceptance threshold can be used to carry out validation and statistical analyses of the classification results following methods in D C Fernandez, R Bhargava, S M Hewitt, I W Levin Nature Biotechnology 23, 469-474 (2005).

TABLE 3 mRNA FISH probes for TOP2A mRNA

| | Sequence | SEQ ID NO. |
|---|---|---|
| 1 | TGTTACGGAGTCACTCTTTT | 9 |
| 2 | AGTTGAAGGTTGGTCCAGAA | 10 |

TABLE 3-continued mRNA FISH probes for TOP2A mRNA

| | Sequence | SEQ ID NO. |
|---|---|---|
| 3 | ACCAAAGGGCATATCAAGA | 11 |
| 4 | CCAAGTCTTCTTTCCACAAA | 12 |
| 5 | CTTCAACAGCCTCCAATTCT | 13 |
| 6 | TGTTCATCTTGTTTTTCCTT | 14 |
| 7 | ATGGTTATTCGTGGAATGAC | 15 |
| 8 | TTTTAGGCCTTCTAGTTCCA | 16 |
| 9 | TTGGCTTAAATGCCAATGTA | 17 |
| 10 | GATTCTGAATCAGACCAGGG | 18 |
| 11 | AATTACTTTCGTCACTGCTC | 19 |
| 12 | TGTTTCTCGTGGAGGGACAT | 20 |
| 13 | TAGGTGGACTAGCATCTGAT | 21 |
| 14 | CTTCAAGGTCTGACACGACA | 22 |
| 15 | GGCTTGAAGACAGTGGTACA | 23 |
| 16 | TCTGGGAAATGTGTAGCAGG | 24 |
| 17 | ACTGGGTTTGTAATTTCAGT | 25 |
| 18 | AGTGGAGGTGGAAGACTGAC | 26 |
| 19 | CAAAGCTGGATCCCTTTTAG | 27 |
| 20 | GCTTTTGAGAGACACCAGAA | 28 |
| 21 | ATTCTTGGTTTTGGCAGGAT | 29 |
| 22 | GGATTTCTTGCTTGTGACTG | 30 |
| 23 | ATGGAAGTCATCACTCTCCC | 31 |
| 24 | CCACAGCTGAGTCAAAGTCC | 32 |
| 25 | TTAAAACCAGTCTTGGGCTT | 33 |
| 26 | TTGGGCTTTACTTCACTTTG | 34 |
| 27 | CCATGAGATGGTCACTATTT | 35 |
| 28 | GCTGAAGTGATCAGATAGCT | 36 |
| 29 | TGCTCTATCTCATATCTACT | 37 |
| 30 | GAGTATCTGTACTAGAACCA | 38 |
| 31 | TTGGCACATAAGAGGCTGAG | 39 |
| 32 | TGAGCAATTTCTCATTGCTT | 40 |
| 33 | GGCCTCTGATGATTTGAGAA | 41 |
| 34 | AAATTGGTTTCTCTCTTTGG | 42 |
| 35 | CTTGGATCAAATGTTGTCCC | 43 |
| 36 | ATTGCTGAGCATGGTTATCA | 44 |

REFERENCES

1. Espina, V. et al. Laser-capture microdissection. *Nat. Protoc.* 1, 586-603 (2006).
2. Armani, M., Tangrea, M. A. & Smela, E. Quantifying mRNA levels across tissue sections with 2D-RT-qPCR. 3383-3393 (2011). doi:10.1007/s00216-011-5062-8
3. Bagasra, O. Protocols for the in situ PCR-amplification and detection of mRNA and DNA sequences. *Nat. Protoc.* 2, 2782-95 (2007).
4. Moffitt, J. R. et al. High-performance multiplexed fluorescence in situ hybridization in culture and tissue with matrix imprinting and clearing. *Proc. Natl. Acad. Sci.* 113, 201617699 (2016).
5. Femino, A. M., Fay, F. S., Fogarty, K. & Singer, R. H. Visualization of Single RNA Transcripts in Situ. *Science (80-.).* 280, (1998).
6. Raj, A., van den Bogaard, P., Rifkin, S. A., van Oudenaarden, A. & Tyagi, S. Imaging individual mRNA molecules using multiple singly labeled probes. *Nat. Methods* 5, 877-9 (2008).
7. Lyubimova, A. et al. Single-molecule mRNA detection and counting in mammalian tissue. *Nat. Protoc.* 8, 1743-58 (2013).
8. Morton, M. L. et al. Identification of mRNAs and lincRNAs associated with lung cancer progression using next-generation RNA sequencing from laser micro-dissected archival FFPE tissue specimens. *Lung Cancer* 85, 31-39 (2014).
9. Ståhl, P. L. et al. Visualization and analysis of gene expression in tissue sections by spatial transcriptomics. *Science (80-.).* 353, (2016).
10. Achim, K. et al. High-throughput spatial mapping of single-cell RNA-seq data to tissue of origin. *Nat. Biotechnol.* 33, 503-509 (2015).
11. Satija, R., Farrell, J. A., Gennert, D., Schier, A. F. & Regev, A. Spatial reconstruction of single-cell gene expression data. *Nat. Biotechnol.* 33, 495-502 (2015).
12. Damhorst, G. L. et al. Smartphone-imaged HIV-1 reverse transcription loop-mediated isothermal amplification (RT-LAMP) on a chip from whole blood. *Engineering* 1, 324-335 (2015).
13. Notomi, T. et al. Loop-mediated isothermal amplification of DNA. *Nucleic Acids Res.* 28, E63 (2000).
14. Siegel, R. L., Miller, K. D. & Jemal, A. Cancer statistics, 2015. *CA. Cancer J. Clin.* 65, 5-29 (2015).
15. Collins, A. T., Berry, P. A., Hyde, C., Stower, M. J. & Maitland, N. J. Prospective Identification of Tumorigenic Prostate Cancer Stem Cells. 10946-10952 (2005). doi:10.1158/0008-5472.CAN-05-2018
16. Feldman, B. J. & Feldman, D. The development of androgen-independent prostate cancer. *Nat. Rev. Cancer* 1, 34-45 (2001).
17. Pienta, K. J. & Bradley, D. Mechanisms Underlying the Development of Androgen-Independent Prostate Cancer. *Clin. Cancer Res.* 12, (2006).
18. Tomlins, S. A. et al. Integrative molecular concept modeling of prostate cancer progression. *Nat. Genet.* 39, 41-51 (2007).
19. Koivisto, P. et al. Androgen Receptor Gene Amplification: A Possible Molecular Mechanism for Androgen Deprivation Therapy Failure in Prostate Cancer. *Cancer Res.* 57, (1997).
20. Cheville, J. C. et al. Gene Panel Model Predictive of Outcome in Men at High-Risk of Systemic Progression and Death From Prostate Cancer After Radical Retropubic Prostatectomy. 26, (2016).
21. Cheville, J., Karnes, R. & Therneau, T. Gene panel model predictive of outcome in men at high-risk of systemic progression and death from prostate cancer after radical retropubic prostatectomy. *J. Clin.* (2008).

22. Goldsworthy, S. M., Stockton, P. S., Trempus, C. S., Foley, J. F. & Maronpot, R. R. Effects of fixation on RNA extraction and amplification from laser capture microdissected tissue. *Mol. Carcinog.* 25, 86-91 (1999).
23. Wang, H. et al. Histological staining methods preparatory to laser capture microdissection significantly affect the integrity of the cellular RNA. *BMC Genomics* 7, 97 (2006).
24. Fend, F. et al. Immuno-LCM : Laser Capture Microdissection of Immunostained Frozen Sections for mRNA Analysis. *Am. J. Pathol.* 154, 61-66 (1999).
25. Fernandez, D. C., Bhargava, R., Hewitt, S. M. & Levin, I. W. Infrared spectroscopic imaging for histopathologic recognition. *Nat. Biotechnol.* 23, 469-474 (2005).
26. Bhargava, R. Towards a practical Fourier transform infrared chemical imaging protocol for cancer histopathology. *Anal. Bioanal. Chem.* 389, 1155-1169 (2007).
27. Bhargava, R., Fernandez, D. C., Hewitt, S. M. & Levin, I. W. High throughput assessment of cells and tissues: Bayesian classification of spectral metrics from infrared vibrational spectroscopic imaging data. *Biochim. Biophys. Acta-Biomembr.* 1758, 830-845 (2006).
28. Super small amount fixed-quantity dispenser NANO MASTER SMP-III|Musashi engineering. Available at: http://www.musashi-engineering.co.jp.e.cn.hp.transer.com/products/100_3-1-2-2.html. (Accessed: 3 Apr. 2017)
29. NanoQuot™ Microplate Dispenser. Available at: http://www.biotek.com/about/news.html?id=8672. (Accessed: 23 Dec. 2016)
30. Itonaga, M. et al. Novel Methodology for Rapid Detection of KRAS Mutation Using PNA-LNA Mediated Loop-Mediated Isothermal Amplification. *PLoS One* 11, e0151654 (2016).
31. Itzkovitz, S., Lyubimova, A. & Blat, I. Single-molecule transcript counting of stem-cell markers in the mouse intestine. *Nat. cell . . .* (2012).

EXAMPLE 3

Device for Generating a Pixelized Tissue Sample

Figure 31A:
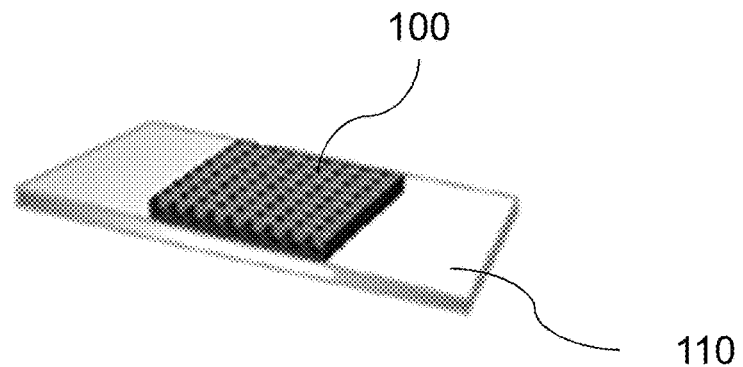
FIGS. 31A-31B. Illustrate an embodiment of a device for the pixelation of a tissue sample.
Figure 31B:
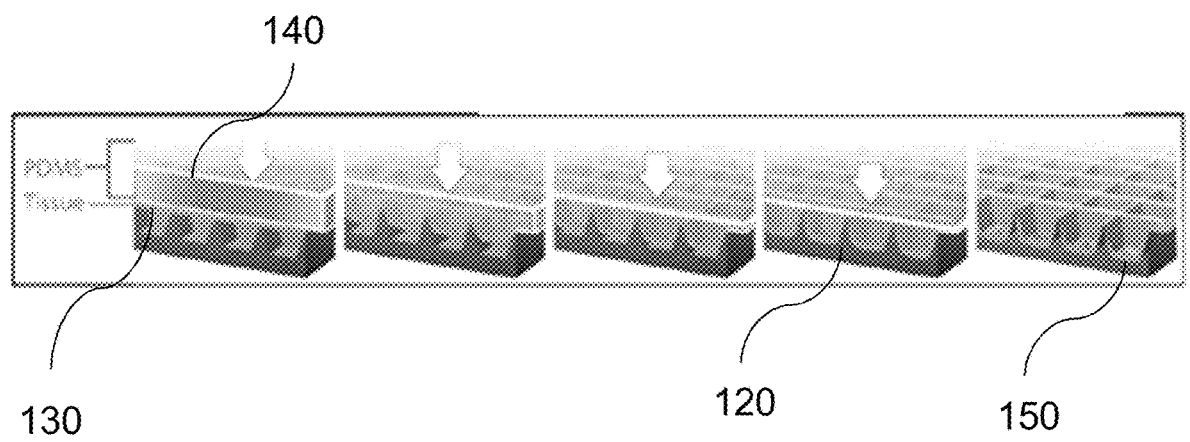

In an embodiment, described herein is a device for pixelating a tissue sample. An exemplary device is provided in FIGS. 22A-K and 31A-B. The device includes a plurality of wells 100 supported by or embedded in a substrate 110 for receiving a tissue sample, including a cryogenic histogram. A shearing surface 120 positioned between the wells has a sharp edge to sever a tissue sample 120 when force is applied to it. A deformable substrate 140 configured to fit over the plurality of wells 100 and placed on top of the tissue sample may be used to force tissue sample into the wells and ensure the tissue sample 130 is severed such that a portion (e.g., "island") enters each of the plurality of wells 100. When force, such as that provided by a centrifuge, is applied, as indicated by the arrow in FIG. 31B, the tissue sample severs such that a portion is forced into each of the wells generating a tissue sample island 150 in each well and thereby creating a pixelized tissue sample. Upon relaxation or removal of the force, the tissue sample remains in the well, and the deformable substrate relaxes away from the well. As desired, the deformable substrate may be removed, with the pixilated tissue ready for further action, including processing, amplification and imaging, as shown in the right-most panel of FIG. 31B.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, such as compositions, physical dimensions or temperatures, all individual members of the group and all combinations and subcombinations possible of the group are intended to be individually included in the disclosure. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The methods, chips and kit now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the methods, chips and kits described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

We claim:

1. A device for generating a pixelized tissue sample comprising:
   a substrate;
   a plurality of wells supported by or embedded in said substrate; and
   a shearing surface positioned between adjacent wells, wherein the shearing surface has a sharp edge configured to sever a tissue sample under an applied centrifugal force into a plurality of tissue sample islands, with each well containing a unique tissue sample island so as to maintain spatial information of a tissue sample during use.

2. The device of claim 1, wherein said substrate is silicon, a glass, a metal, an insulator or a dielectric.

3. The device of claim 1, wherein said shearing surface is a sharp edge of an inverted pyramidal well.

4. The device of claim 1, wherein each of said wells comprises a target-specific primer set and an enzyme for nucleic acid amplification.

5. The device of claim 1 further comprising a deformable substrate configured to force a tissue sample into each of said plurality of wells and shear the tissue between the shearing surface and the deformable substrate.

6. The device of claim 1, wherein the substrate comprises undoped silicon.

7. The device of claim 1 comprising enzymes and/or primers disposed on at least one surface of the plurality of wells.

8. The device of claim 1 comprising one or more positively charged functional groups disposed on one or more surfaces of the wells.

9. The device of claim 1 comprising a silanized layer disposed on one or more surfaces of the wells.

10. The device of claim 1, wherein each of said wells has a volume of less than or equal to 1000 pL.

11. The device of claim 1, wherein each of said wells has a cross-sectional dimension of less than or equal to 1 mm.

12. The device of claim 1, wherein each of said wells has a maximum depth of less than or equal to 1 mm.

13. The device of claim 5, wherein said deformable substrate comprises a polymer.

14. The device of claim 13, wherein said polymer comprises polymethylsiloxane (PDMS), SU-8, polyethylene glycol (PEG), a photoresist, a PEG-based polymer or any combination thereof.

15. The device of claim 1, wherein the plurality of wells comprises greater than 500 wells.

16. A system for generating a pixelized tissue sample, the system comprising:
   the device of claim 1; and
   a centrifuge configured to receive the device and a tissue sample and shear the tissue sample at the shearing surface.

* * * * *